(12) United States Patent
Puthigae et al.

(10) Patent No.: US 8,227,665 B2
(45) Date of Patent: Jul. 24, 2012

(54) POLYNUCLEOTIDES AND METHODS FOR IMPROVING PLANTS

(75) Inventors: Sathish Puthigae, Auckland (NZ); Jonathan Robert Phillips, Bonn (DE); Claudia Jeannette Smith-Espinoza, Bonn (DE); Catherine Jane Bryant, Papatoetoe (NZ); Kieran Michael Elborough, Franklin (NZ); Margaret Biswas, Auckland (NZ)

(73) Assignee: Fonterra Co-Operative Group Limited, Auckland (NZ)

( * ) Notice: Subject to any disclaimer, the term of this patent is extended or adjusted under 35 U.S.C. 154(b) by 578 days.

(21) Appl. No.: 12/324,664

(22) Filed: Nov. 26, 2008

(65) Prior Publication Data
US 2009/0229009 A1    Sep. 10, 2009

Related U.S. Application Data

(60) Provisional application No. 60/990,590, filed on Nov. 27, 2007.

(51) Int. Cl.
*A01H 5/00* (2006.01)
*C12N 15/82* (2006.01)

(52) U.S. Cl. ........ 800/290; 800/295; 435/419; 536/24.5

(58) Field of Classification Search .............. 800/278, 800/284
See application file for complete search history.

(56) References Cited

U.S. PATENT DOCUMENTS

| | | |
|---|---|---|
| 6,350,934 B1 | 2/2002 | Zwick et al. |
| 7,728,191 B2 | 6/2010 | Kuroda |
| 2006/0123505 A1* | 6/2006 | Kikuchi et al. .............. 800/278 |
| 2011/0093962 A1* | 4/2011 | Heidbrink et al. .............. 800/13 |

OTHER PUBLICATIONS

Klahre et al (PNAS, Sep. 3, 2002, vol. 99 No. 19 11981-11986.*
Lehner et al (Functional Genomics, 3: 68-83).*

* cited by examiner

*Primary Examiner* — Anne Grunberg
*Assistant Examiner* — Lee A Visone
(74) *Attorney, Agent, or Firm* — Knobbe, Martens, Olson & Bear, LLP

(57) ABSTRACT

The invention provides methods and compositions for producing plant with altered biomass, the methods comprising the step of altering the expression and/or activity of the polypeptide comprising the sequence of SEQ ID NO:1, or a variant thereof, in a plant cell or plant. The invention also provides a polypeptide comprising the sequence of SEQ ID NO:1, and fragments of variants thereof the sequence. The invention also provides polynucleotides encoding such polypeptide sequences. The invention also provides constructs, cells and plants comprising such polynucleotides.

15 Claims, 22 Drawing Sheets

FIGURE 1

```
                                                                Score      E
Sequences producing significant alignments:                    (bits)   Value dbj|AK098904.1|  Oryza sativa (japonica cultivar-group) cDNA...  1798    0.0
dbj|AK065041.1|  Oryza sativa (japonica cultivar-group) cDNA...  1798    0.0
dbj|AK065992.1|  Oryza sativa (japonica cultivar-group) cDNA...  1792    0.0
dbj|AK065747.1|  Oryza sativa (japonica cultivar-group) cDNA...  1531    0.0
dbj|AK062069.1|  Oryza sativa (japonica cultivar-group) cDNA...  1183    0.0
emb|AL731876.3|CNS08C8G  Oryza sativa chromosome 12, . BAC O...   506   e-140
gb|AY059105.1|   Arabidopsis thaliana unknown protein (At3g26... 235    4e-59
gb|AY035031.1|   Arabidopsis thaliana unknown protein (At3g26... 235    4e-59
ref|NM_202633.1| Arabidopsis thaliana regulator of chromoso...   235    4e-59
ref|NM_113515.2| Arabidopsis thaliana regulator of chromoso...   235    4e-59
emb|BX822376.1|CNS0A7VQ  Arabidopsis thaliana Full-length cD...  231    6e-58
dbj|AB023041.1|  Arabidopsis thaliana genomic DNA, chromosom...  196    2e-47
ref|XM_466543.1| Oryza sativa (japonica cultivar-group),  mRNA   125    4e-26
dbj|AK102225.1|  Oryza sativa (japonica cultivar-group) cDNA...  125    4e-26
```

| | | | | | | | | | | | | | | | | | | | | | | | |
|---|---|---|---|---|---|---|---|---|---|---|---|---|---|---|---|---|---|---|---|---|---|---|---|
| BAB01075.1 | L | L | G | P | L | E | N | V | P | V | V | Q | I | A | A | G | Y | C | Y | L | L | A | L | A | C | Q | P | N | G | M | S | V | Y | S | V | G | C | G | L | G | G | K | L | G | H | G | S | R | T | D | 344 |
| AAL15211.1 | L | L | G | P | L | E | N | V | P | V | V | Q | I | A | A | G | Y | C | Y | L | L | A | L | A | C | Q | P | N | G | M | S | V | Y | S | V | G | C | G | L | G | G | K | L | G | H | G | S | R | T | D | 244 |
| AKO65992.1 | L | A | G | P | L | E | N | I | P | V | V | Q | I | A | A | A | G | Y | C | Y | L | L | A | L | A | C | Q | P | S | G | M | S | V | Y | S | V | G | C | G | L | G | G | K | L | G | H | G | S | R | T | D | 347 |
| AKC85747.1 | L | A | G | P | L | E | N | I | P | V | V | Q | I | A | A | A | G | Y | C | Y | L | L | A | L | A | C | Q | P | S | G | V | S | V | Y | S | V | G | C | G | L | G | G | K | L | G | H | G | S | R | T | D | 347 |

(figure continues — multiple sequence alignment)

```
Lp_ORF54_RCC1_1    GAAMSFGSNNSGQLGHDRLEEE---------------WRPRPRRS-LQGIR---IIQAAA------
Lp_ORF54_RCC1_2    GRVYAFGKDSFGEVEYGNQGSR----------------VVTTPQLVES-LKDIY---IVQAAI------
Lp_ORF54_RCC1_3    GCKVTFSWGGDMKLGHQTEPND----------------VQPHLLAGPLEDIP---VVQIAA------
Lp_ORF54_RCC1_4    MSVVLSVGCGLGGKLGHGSRSDE---------------KYPRLIEQ-FQTLNIQPVVAA-------
Lp_ORF54_RCC1_5    GRVCTWGWGRYGCLGHGNEECE----------------SVPKVVEI-LSSVK--AVHVAT------
Lp_ORF54_RCC1_6    GDVYSFGCGESSSLGHNTA--EGNNRHSNVLSPELVTS-SQRTDERVVHVSLTNSIYW--
Lp_ORF54_RCC1_7    AKLYAFGAGDKGQLGTELVEHR----------------SERGTPEQVDIDLN---------------
NP_974362_RCC1_1   GFVYTFGYNNSGQLGHGHTEDF----------------ARTQP--VRS-LQGVR---ITQAAA------
NP_974362_RCC1_2   GKVYACGKESFGEAEYGGQGTK----------------PVTTPQLVTS-LKNIF---VVQAAI------
NP_974362_RCC1_3   GKVYTFSWGNDGRLGHQTEAAD----------------VEPRPLLGPLENVP---VVQIAA------
NP_974362_RCC1_4   MSVYSVGCGLGGKLGHGSR-DE----------------KYPRVIEQ-FQILNLQPRVAA-------
NP_974362_RCC1_5   GRVCTWGWGRYGCLGHGNEECE----------------KVPKVVEG-LSHVK--AVHVAT------
NP_974362_RCC1_6   GDVYSFGCGESASLGHHPSFDEQGMRHANVLSPIVVTS-LKQVNERMVQISLTNSIYW--
NP_974362_RCC1_7   GKLFAFGAGDSGQLGTELGKNQ----------------KERCVPEKVDIDLS---------------
NP_966789_RCC1_1   GEVYTFGYNNSGQLGHGHTEDE----------------ARIQP--VRS-LQGVR---IIQAAA------
NP_966789_RCC1_2   GKVYACGKESFGEAEYGGQGTK----------------PVTTPQLVTS-LKNIF---VVQAAI------
NP_566789_RCC1_3   GKVYTFSWGNDGRLGHQTEAAD----------------VEPRPLLGPLENVP---VVQIAA------
NP_566789_RCC1_4   MSVYSVGCGLGGKLGHGSR-DE----------------KYPRVIEQ-FQILNLQPRVAA-------
NP_566789_RCC1_5   GRVCTWGWGRYGCLGHGNEECE----------------SVPKVVEG-LSHVK--AVHVAT------
NP_566789_RCC1_6   GDVYSFGCGESASLGHHPSFDEQGNRHANVLSPIVVTS-LKQVNERMVQISLTNSIYW--
NP_566789_RCC1_7   GKLFAFGAGDQGQLGTELGKNQ----------------KERCVPEKVDIDLS---------------
XP_466543_RCC1_1   GDAYSFGANCWGQLGLGDTEDR----------------FKPCLIRS-LQSIK---ITQAAV------
XP_466543_RCC1_2   GSVYAFGKGSFVWEELSDAADH----------------ITTPKIVES-LKGVF---VVQAAI------
XP_466543_RCC1_3   GQVYTISWGRTEWLGHSSDPSD----------------VEPRLLSGPLEGVL---VAQISA------
XP_466543_RCC1_4   MSVYSVGCGLGGKLGHGCKNNK----------------GTPKLIEH-FLTLSFNPVSVAA------
XP_466543_RCC1_5   GRVCTWGWGHTGCLGHGDEEYR----------------VLPIVVQG-LSNVK--AVHVST------
XP_466543_RCC1_6   GDTYSFGSAESLNIGFQ--EDEEAADDADFSTPSLVES-LKVLNDKAVQISTTNSSYWLN
XP_466543_RCC1_7   GKLYAFGGGIKGQLGVKLSEGQ----------------ERAQNPERVPIDLC---------------
AK098904_RCC1_1    GAVYTFGSNSSGQLGHGSLEEE----------------WRPRIIPSDLQGIR---IIQAAA------
AK098904_RCC1_2    GRVYAFGKDSFGEVEYAAQGSR----------------VVTTPQLVES-LKDIY---IVQAAI------
AK098904_RCC1_3    GHVYTFSWGNDMKLGHQTEPND----------------VQPHLLAGPLENIP---VVQIAI------
AK098904_RCC1_4    MSVYSVGCGLGGKLGHGSR-DE----------------KYPRLIEQ-FQALNIQPVVAA-------
```

FIG. 3-2

| | | |
|---|---|---|
| AK098904_RCC1_5 | GRVCTWGWGRYGCLGHGNEECE------ | ------SVPKVVES-LVNVR--AVHVAT------ |
| AK098904_RCC1_6 | GDVYSFGCGESSSLGHNTITEGN-NRFTNVLSPELVTS-LKRTNERVAQISLTNSIYW--- | |
| AK098904_RCC1_7 | GKLYAFGAGDKGQLGTELVAQE------ | ------SERGTPERVEIDLS------ |
| AK065041_RCC1_1 | GAVYTFGSNSSGQLGHGSLEEE------ | ------WRPRIIRS-LQGIR--I-QAAA------ |
| AK065041_RCC1_2 | GRVYAFGKDSFGEVEYAAQGSR------ | ------VVTTPQIVES-LKDIY--IVQAAI------ |
| AK065041_RCC1_3 | GHVYTFSWGNDMKLGHQTEPND------ | ------VQPHLLAGPLENIP--VVQIAA------ |
| AK065041_RCC1_4 | MSVYSVGCG-GGKLGHGSRTDE------ | ------KYPRLIEQ-FQALNIQP\\\\VAA------ |
| AK065041_RCC1_5 | GRVCTWGWGRYGCLGHGNEECE------ | ------SVPKVVES-LVNVR--AVHVAT------ |
| AK065041_RCC1_6 | GDVYSFGCGESSSLGHNTITEGN-NRFTNVLSPELVTS-LKRTNERVAQISLTNSIYW--- | |
| AK065041_RCC1_7 | GKLYAFGAGDKGQLGTELVAQE------ | ------SERGTPERVEIDLS------ |
| AK065992_RCC1_1 | GAVYTFGSNSSGQLGHGSLEEE------ | ------WRPRIIRS-LQGIR--I-QAAA------ |
| AK065992_RCC1_2 | GRVYAFGKDSFGEVEYAAQGSR------ | ------VVTTPQIVES-LKDIY--IVQAAI------ |
| AK065992_RCC1_3 | GHVYTFSWGNDMKLGHQTEPND------ | ------VQPHLLAGPLENIP--VVQIAI------ |
| AK065992_RCC1_4 | MSVYSVGCG-GGKLGHGSRTDE------ | ------KYPRLIEQ-FQALNIQPVVVAA------ |
| AK065992_RCC1_5 | GRVCTWGWGRYGCLGHGNEECE------ | ------SVPKVVES-LVNVR--AVHVAT------ |
| AK065992_RCC1_6 | GDVYSFGCGEESSLGHNTITEGN-NRFTNVLSPELVTS-LKRTRERVAQISLTNSIYW--- | |
| AK065992_RCC1_7 | GKLYAFGAGDKGQLGTELVAQE------ | ------SERGTPERVEIDLS------ |
| AK065747_RCC1_1 | GAVYTFGSNSSGQLGHGSLEEE------ | ------WRPRIIRS-LQGIR--I-QAAA------ |
| AK065747_RCC1_2 | GRVYAFGKDSFGEVEYAAQESR------ | ------VVTTPQIVES-LKDIY--IVQAAI------ |
| AK065747_RCC1_3 | GHVYTFSWGNDMKLGHQTEPND------ | ------VQPHLLAGPLENIP--VVQIAA------ |
| AK065747_RCC1_4 | VSVYSVGCG-GGKLGHGSRTDE------ | ------KYPRLIEQ-FQALNIQP\\\\VAA------ |
| AK065747_RCC1_5 | GRVCTWGWGRYGCLGHGNEECE------ | ------SVPKVVES-LVNVR--AVHVAT------ |
| AK065747_RCC1_6 | GDVYSFGCGESSSLGHNTITEGN-NRFTNVLSPELVTS-LKRTNERVAQISLTNSIYW--- | |
| AK065747_RCC1_7 | GKLYAFGAGDKGQLGTELVAQE------ | ------SERGTPERVEIDLS------ |
| AK062069_RCC1_2 | GRVYAFGKDSFGQVEYAAQGSR------ | ------VVTTPQIVES-LKDIY--IVQAAI------ |
| AK062069_RCC1_3 | GHVYTFSWGNDMKLGHQTEPND------ | ------VQPHLLAGPLENIP--VVQIAA------ |
| AK062069_RCC1_4 | MSVYSVGCG-GGKLGHGSRTDE------ | ------KYPRLLEQ-FQALNIQP\\\\VAA------ |
| AK062069_RCC1_5 | GRVCTWGWGRYGCLGHGNEECE------ | ------SVPKVVES-LVNVR--AVHVAT------ |
| AK062069_RCC1_6 | GDVYSEGCGESSCLGHNTTEGN-NRFTNVLSPELVTS-LKRTNERVAQISLTNSIYW--- | |
| AK062069_RCC1_7 | GKLYAFGAGDKGQLGTELVAQE------ | ------SERGTPERVEIDLS------ |

FIG. 3-3

| | |
|---|---|
| Lp_ORF54_RCC1_1 | ---GAGRTMLVSDA--- |
| Lp_ORF54_RCC1_2 | ---GNFFTAVLSRE--- |
| Lp_ORF54_RCC1_3 | ---GYCYLLLACQPSG |
| Lp_ORF54_RCC1_4 | ---GAWHAAVVGKD--- |
| Lp_ORF54_RCC1_5 | ---GDYTTFVVSHK--- |
| Lp_ORF54_RCC1_6 | ----NAHTFALTES--- |
| Lp_ORF54_RCC1_7 | |
| NP_974362_RCC1_1 | ---GAARTMLISDD--- |
| NP_974362_RCC1_2 | ---GNYFTAVISRE--- |
| NP_974362_RCC1_3 | ---GYCYLLALACQPNG |
| NP_974362_RCC1_4 | ---GAWHAAVVGQD--- |
| NP_974362_RCC1_5 | ---GDYTTEVVSDD--- |
| NP_974362_RCC1_6 | ----NAHTFALTES--- |
| NP_974362_RCC1_7 | |
| NP_566789_RCC1_1 | ---GAARTMLISDD--- |
| NP_566789_RCC1_2 | ---GNYFTAVLSRE--- |
| NP_566789_RCC1_3 | ---GYCYLLALACQPNG |
| NP_566789_RCC1_4 | ---GAWHAAVVGQD--- |
| NP_566789_RCC1_5 | ---GDYTTFVVSDD--- |
| NP_566789_RCC1_6 | ----NAHTFALTES--- |
| NP_566789_RCC1_7 | |
| XP_466543_RCC1_1 | ---GSRQTMLVSDT--- |
| XP_466543_RCC1_2 | ---GGYFSAFLSRE--- |
| XP_466543_RCC1_3 | ---GNCYLIMLAYQPTG |
| XP_466543_RCC1_4 | ---GTWHAAALGDD--- |
| XP_466543_RCC1_5 | ---GEYTTFVVSDN--- |
| XP_466543_RCC1_6 | SEMGYPHTFALMES--- |
| XP_466543_RCC1_7 | |
| AK098904_RCC1_1 | ---GAGRTMLVSDA--- |
| AK098904_RCC1_2 | ---GNFFTAVLSRE--- |
| AK098904_RCC1_3 | ---GYCYLLALACQPSG |

| | |
|---|---|
| AK098904_RCC1_4 | ---GAWHAAVVGKD--- |
| AK098904_RCC1_5 | ---GDYTTFVVSDK--- |
| AK098904_RCC1_6 | ---GNAHTFALTDS--- |
| AK098904_RCC1_7 | --- |
| AK065041_RCC1_1 | ---GAGRTMLVSDA--- |
| AK065041_RCC1_2 | ---GNFFTAVLSRE--- |
| AK065041_RCC1_3 | ---GYCYLLALACQPSG |
| AK065041_RCC1_4 | ---GAWHAAVVGKD--- |
| AK065041_RCC1_5 | ---GDYTTFVVSDK--- |
| AK065041_RCC1_6 | ---NAHTFALTDS--- |
| AK065041_RCC1_7 | --- |
| AK065992_RCC1_1 | ---GAGRTMLVSDA--- |
| AK065992_RCC1_2 | ---GNFFTAVLSRE--- |
| AK065992_RCC1_3 | ---GYCYLLALACQPSG |
| AK065992_RCC1_4 | ---GAWHAAVVGKD--- |
| AK065992_RCC1_5 | ---GDYTTFVVSDK--- |
| AK065992_RCC1_6 | ---NAHTFALTDS--- |
| AK065992_RCC1_7 | --- |
| AK065747_RCC1_1 | ---GAGRTMLVSDA--- |
| AK065747_RCC1_2 | ---GNFFTAVLSRE--- |
| AK065747_RCC1_3 | ---GYCYLLALACQPSG |
| AK065747_RCC1_4 | ---GAWHAAVVGKD--- |
| AK065747_RCC1_5 | ---GDYTTFVVSDK--- |
| AK065747_RCC1_6 | ---NAHTFALTDS--- |
| AK065747_RCC1_7 | --- |
| AK062069_RCC1_2 | ---GNFFTAVLSRE--- |
| AK062069_RCC1_3 | ---GYCYLLALACQPSG |
| AK062069_RCC1_4 | ---GAWHAAVVGKD--- |
| AK062069_RCC1_5 | ---GDYTTFVVSDK--- |
| AK062069_RCC1_6 | ---NAHTFALTDS--- |
| AK062069_RCC1_7 | --- |

FIG. 3-4

| FIG. 3 | |
|---|---|
| FIG. 3-1 | |
| FIG. 3-2 | |
| FIG. 3-3 | |
| FIG. 3-4 | |

FIG. 7-1

```
AK065992    ----MDATTSSGASSSLPLHLIIDDALALVSPLQQSFQRSQRHCFGGSAPGEFPLAANPS    56
AK065747    ----MDATTSSGASSSLPLHLIIDDALALVSPLQQSFQRSQRHCFGGSAPGEFPLAANPS    56
AK065041    ----MDATTSSGASSSLPLHLIIDDALALVSPLQQSFQRSQRHCFGGSAPGEFPLAANPS    56
AK098904    ----MDATTSSGASSSLPLHLIIDDALALVSPLQQSFQRSQRHCFGGSAPGEFPLAANPS    56
AK062069.1  ------------------------------------------------------------
ORF54       ----MDATTSSGASSSLPLHLIVDDTLSLVSPLQQSYQRSQRHCLGDSAPGEFPLAANPS    56
XP466543    MQCPMDAAAS-GTSPVMQFHGIVDEPPSHSSPLHTALERSQRHCYGHETPGEFPLAVSPS    59

AK065992    IVLHVLTSCNLEPDDLAHLEATCSFFRKPANFPPDFQLSMSELAALDMCQKRAIFKPMTQ    116
AK065747    IVLHVLTSCNLEPDDLAHLEATCSFFRKPANFPPDFQLSMSELAALDMCQKRAIFKPMTQ    116
AK065041    IVLHVLTSCNLEPDDLAHLEATCSFFRKPANFPPDFQLSMSELAALDMCQKRAIFKPMTQ    116
AK098904    IVLHVLTSCNLEPDDLAHLEATCSFFRKPANFPPDFQLSMSELAALDMCQKRAIFKPMTQ    116
AK062069.1  ------------------------------------------------------------
ORF54       IVLHVLTSCNLEPEDLAHLEATCKFFRKPANFPPDFLLSMSELAAFDMCQNRAIFKPMGT    116
XP466543    IVLHVLSTCELDPKDLAALEATCTFFSKPANFEPNFALSLPEVAAFDMCHKRPMVKLMAQ    119

AK065992    QEREMFKQRCGGSWKLVLRFIMAGEACCRREKSQAIAGPGHSIAVTTSGAVYTFGSNSSG    176
AK065747    QEREMFKQRCGGSWKLVLRFIMAGEACCRREKSQAIAGPGHSIAVTTSGAVYTFGSNSSG    176
AK065041    QEREMFKQRCGGSWKLVLRFIMAGEACCRREKSQAIAGPGHSIAVTTSGAVYTFGSNSSG    176
AK098904    QEREMFKQRCGGSWKLVLRFIMAGEACCRREKSQAIAGPGHSIAVTTSGAVYTFGSNSSG    176
AK062069.1  ------------------------------------------------------------
ORF54       QEKEMFKQRCGGTWKLVLRFIT-GEACCRREKSQAIAGPGHSVAVTASGAAYSFGSNNSG    176
XP466543    QEREQLKQRCGGSWKLVFKYIVARE----RNYSRIVAGPGHSIVVTTKGDAYSFGANCWG    175
```

```
AK659992    QLGHGSLEEEWRPRIIRSLQGIRIIQAAAGAGRTMLVSDAGRVYAFGKDSFGEVEYAAQG  236
AK657747    QLGHGSLEEEWRPRIIRSLQGIRIIQAAAGAGRTMLVSDAGRVYAFGKDSFGEVEYAAQG  236
AK650041    QLGHGSLEEEWRPRIIRSLQGIRIIQAAAGAGRTMLVSDAGRVYAFGKDSFGEVEYAAQG  236
AK098904    QLGHGSLEEEWRPRIIRSLQGIRIIQAAAGAGRTMLVSDAGRVYAFGKDSFGEVEYAAQG  236
AK062069.1  ----------------------IQAAAGAGRTMLVSDAGRVYAFGKDSFGEVEYAAQG    36
ORF54       QLGHDRLEEEWRPRIIRSLQGIRIIQAAAGAGRTMLVSDAGRVYAFGKDSFGEVEYGNQG  236
XP465543    QLGLGDTEDRFKPCLIRSLQSIKITQAAVGSRQTMLVSDTGSVYAFGKGSFVWEELS-DA  234
                 .   *:  : ****:.  : : ***.*: :******.*   :***.**. ** .  .

AK659992    SRVVTTPQLVESLKDIYIVQAAIGNFFTAVLSREGHVYTFSWGNDMKIGHQTEPNDVQPH  296
AK657747    SRVVTTPQLVESLKDIYIVQAAIGNFFTAVLSREGHVYTFSWGNDMKIGHQTEPNDVQPH  296
AK650041    SRVVTTPQLVESLKDIYIVQAAIGNFFTAVLSREGHVYTFSWGNDMKIGHQTEPNDVQPH  296
AK098904    SRVVTTPQLVESLKDIYIVQAAIGNFFTAVLSREGHVYTFSWGNDMKIGHQTEPNDVQPH  296
AK062069.1  SRVVTTPQLVESLKDIYIVQAAIGNFFTAVLSREGHVYTFSWGNDMKIGHQTEPNDVQPH   96
ORF54       SRVVTTPQLVESLKDIYIVQAAIGNFFTAVLSREGCVYTFSWGGDMKIGHQTEPNDVQPH  296
XP465543    ADHITTPKIVESLKGVFVVQAIGGYFSAFLSREGQVYTISWGRTERIGHSSDPSDVEPR  294
              . ***::****** ::  **   *:*::****  ***:**:  :: ** : :*** *

AK659992    LLAGPLENIPVVQIAAGYCYLLALACQPSGMSVYSVGCGLGGKLGHGSRTDEKYPRLIEQ  356
AK657747    LLAGPLENIPVVQIAAGYCYLLALACQPSGMSVYSVGCGLGGKLGHGSRTDEKYPRLIEQ  356
AK650041    LLAGPLENIPVVQIAAGYCYLLALACQPSGMSVYSVGCGLGGKLGHGSRTDEKYPRLIEQ  356
AK098904    LLAGPLENIPVVQIAAGYCYLLALACQPSGMSVYSVGCGLGGKLGHGSRTDEKYPRLIEQ  356
AK062069.1  LLAGPLENIPVVQIAAGYCYLLALACQPSGMSVYSVGCGLGGKLGHGSRTDEKYPRLIEQ  156
ORF54       LLAGPLEDIPVVQIAAGYCYLLALACQPSGMSVYSVGCGLGGKLGHGSRTDEKYPRLIEQ  356
XP465543    LLSGPLEGV-VAQISAGNCYLLMLAYQPTGMSVYSVGCGLGGKLGHGCKNNKGTPKLIEH  354
            **:****.:  .*::**  ***:** **:****************  .:: . *:***:
```

FIG. 7-2

```
AK065992    FQALNIQPVVVAAGAWHAAVVGKDGRVCTWGWGRYGCLGHGNEECESVPKVVESLVNVRA  416
AK065747    FQALNIQPVVVAAGAWHAAVVGKDGRVCTWGWGRYGCLGHGNEECESVPKVVESLVNVRA  416
AK065041    FQALNIQPVVVAAGAWHAAVVGKDGRVCTWGWGRYGCLGHGNEECESVPKVVESLVNVRA  416
AK098904    FQALNIQPVVVAAGAWHAAVVGKDGRVCTWGWGRYGCLGHGNEECESVPKVVESLVNVRA  416
AK062069.1  FQALNIQPVVVAAGAWHAAVVGKDGRVCTWGWGRYGCLGHGNEECESVPKVVESLVNVRA  216
ORF54       FQTLNIQPVVVAAGAWHAAVVGKDGRVCTWGWGRYGCLGHGNEECESVPKVVETLSSVKA  416
XP466543    FLTLSFNPVSVAAGTWHAAALGDDGRVCTWGWHTGCLGHGDEEYRVLPTVVQGLSNVKA   414
              *  ::  :*.  *****    ::*.*****  ***** **  :   *  ::  ***

AK065992    VHVATGDYTTFVVSDKGDVYSFGCGESSSLGHNTITEGNNRHTNVLSPELVTSLKRINER  476
AK065747    VHVATGDYTTFVVSDKGDVYSFGCGESSSLGHNTITEGNNRHTNVLSPELVTSLKRINER  476
AK065041    VHVATGDYTTFVVSDKGDVYSFGCGESSSLGHNTITEGNNRHTNVLSPELVTSLKRINER  476
AK098904    VHVATGDYTTFVVSDKGDVYSFGCGESSSLGHNTITEGNNRHTNVLSPELVTSLKRINER  476
AK062069.1  VHVATGDYTTFVVSDKGDVYSFGCGESSSLGHNTITEGNNRHTNVLSPELVTSLKRINER  276
ORF54       VHVATGDYTTFVVSHKGDVYSFGCGESSSLGHNTAIEGNNRHSNVLSPELVTSSQRIDER  476
XP466543    VHVSTGEYTTFVVSDNGDTYSFGSAESLNIGFQEDEEAAD-DADFSTPSLVESLKVLNDK  473
              ***. **:*****.:**.****.. **.*.*   *:.** . **: *.::  :..:

AK065992    VAQISLTNSIVWN-----AHTFALTDSGKLYAFGAGDKGQLGTELVAQESERGTPERVE   530
AK065747    VAQISLTNSIVWN-----AHTFALTDSGKLYAFGAGDKGQLGTELVAQESERGTPERVE   530
AK065041    VAQISLTNSIVWN-----AHTFALTDSGKLYAFGAGDKGQLGTELVAQESERGTPERVE   530
AK098904    VAQISLTNSIVWN-----AHTFALTDSGKLYAFGAGDKGQLGTELVAQESERGTPERVE   530
AK062069.1  VAQISLTNSIVWN-----AHTFALTDSGKLYAFGAGDKGQLGTELVAQESERGTPERVE   330
ORF54       VVHVSLTNSIVWN-----AHTFALTESAKLYAFGAGDKGQLGTELVEHRSERGTPEQVD   530
XP466543    AVQISTTNSSVWLNSEMGYPHTEALMESGKLYAFGGGIKGQLGVKLSEGGQERAQNPERVP 533
              . :*  ** :*         ** *  * ********. .:***: : *   *  * *
```

FIG. 7-3

```
AK065992    IDLS 534
AK065747    IDLS 534
AK065041    IDLS 534
AK098904    IDLS 534
AK062069.1  IDLS 334
ORF54       IDIN 534
XP465543    IDIC 537
            * * *
```

```
BAB01_075    MDATSGT---PSLQYINLPEQSVSTTSPPVSPFQRPKRHCFGDTTPGEFPLAANPSIVLH    57
AAL15211     ------------------------------------------------------------
ORF54        MDATTSSGASSSLPIHLIVDDTLS-VSPLQQSYQRSQRHCLGDSAPGEFPLAANPSIVLH    60
                                                         *  **********

BAB01_075    VLTECRLDPRDLANLEATCSFFSQPANFAPDINLS-SELAALDMCNKRVIFKPMNEEERQ   117
AAL15211     -----------------------------------MCNKRVIFKPMNEEERQ          17
ORF54        VLTSTNLEPEDLAHLEATCKFFRKPANFPPDFLLSMSELAAFDMCQNRAIFKPMGTQEKE   120
             ***   * *  **  *****.** .****.   *  ****.***.:****:..:*:.

BAB01_075    EMKRRCGGSWKLVLRFLLAGEACCRREKSQAVAGPGHSVAVTSKGEVYTFGYNNSGQLGH   177
AAL15211     EMKRRCGGSWKLVLRFLLAGEACCRREKSQAVAGPGHSVAVTSKGEVYTFGYNNSGQLGH    77
ORF54        MFKQRCGGTWKLVLRFITLGEACCRREKSQAIAGPGHSVAV-ASGAAYSFGSNNSGQLGH   180
              :*:****.******: :************:*********  *..  :** *******

BAB01_075    GHTEDEARIQPVRSLQGVRIIQAAAGAARTMLISDDGKVYACGKESFGEAEYGGQTKPV   237
AAL15211     GHTEDEARIQPVRSLQGVRIIQAAAGAARTMLISDDGKVYACGKESFGEAEYGGQTKPV   137
ORF54        DRLEEWRPRPLRSLQGIRIIQAAAGAGRTMLVSDAGRVYAFGKDSFGEVEYGNQGSRVV   240
               ..  .   : ****:*********.****:**.*:***.**:****.***.*. .*

BAB01_075    TTPQLVTSLKNIFVVQAAIGNYFTAVLSREGKVYTFSWGNDGRLGIIGTEAADVEPRPLLG   297
AAL15211     TTPQLVTSLKNIFVVQAAIGNYFTAVLSREGKVYTFSWGNDGRLGHIGTEAADVEPRPLLG   197
ORF54        TTPQLVESLKDIYIVQAAIGNFFTAVLSREGCVYTFSWGGDMKLGHQTEPNDVQPHLLAG   300
             ******.***:*::*******:********* ******.*  **:  **...*:*  *.*
```

FIG. 8-2

| | | |
|---|---|---|
| BAB01075 | PLENVPVVQIAAGYCYLLALACQPNGMSVYSVGCGLGGKLGHGSRTDEKYPRVIEQFQIL | 357 |
| AAL15211 | PLENVPVVQIAAGYCYLLAGACQPNGMSVYSVGCGLGGKLGHGSRTDEKYPRVIEQFQIL | 257 |
| ORF54 | PLEDIPVVQIAAGYCYLLLLACQPSGMSVYSVGCGLGGKLGHGSRSDEKYPRLIEQFQTG | 360 |
| | * *::****** * *.**** * **::*:***.  | |

| | | |
|---|---|---|
| BAB01075 | NLQPRVVAAGAWHAAAVVGQDGRVCTWGWGRYGCLGHNEECESVPKVVEGLSHVKAVHVA | 417 |
| AAL15211 | NLQPRVVAAGAWHAAAVVGQDGRVCTWGWGRYGCLGHNEECESVPKVVEGLSHVKAVHVA | 317 |
| ORF54 | NIQPVVVAAGAWHAAVVGKDGRVCTWGWGRYGCLGHNEECESVPKVVETLSSVKAVHTA | 420 |
| | *:**:*:******.:*.***********************:.****. * | |

| | | |
|---|---|---|
| BAB01075 | TGDYITFVVSDDGDVYSFGCGESASLGHHPSFDEQGNRHANVLSPTVVTSLKQVNERMVQ | 477 |
| AAL15211 | TGDYITFVVSDWGDVYSFGCGESASLGHHPSFDEQGNRHANVLSPTVVTSLKQVNERMVQ | 377 |
| ORF54 | TGDYITFVVSHKGDVYSFGCGESSSLGHNTAIEGN-NRHSNVLSPELVTSSQRTDERVVH | 479 |
| | ********  .*****::*.: :: *::* **:* *::***.: | |

| | | |
|---|---|---|
| BAB01075 | ISLTNSIYWNAHTFALTESGKLFAFGAGDQQQLGTELRKNQKERCVPEKVDIDLS | 532 |
| AAL15211 | ISLTNSIYWNAHTFALTESGKLFAFGAGDQGQLGTELGKNQKERCVPEKVDIDLS | 432 |
| ORF54 | VSLTNSIYWNAHTFALTESAKEYAFGAGDKGQLGTELVEHRSERGTPEQVDIDLN | 534 |
| | :******************.*::******. ****** ::::**.. *:****: | |

POLYNUCLEOTIDES AND METHODS FOR IMPROVING PLANTS

CROSS-REFERENCE TO RELATED APPLICATIONS

This application claims priority to U.S. Provisional Application No. 60/990,590, filed Nov. 27, 2007. The priority application is incorporated herein by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled Sequence-Listing-DAIRY94003AUS.txt, created Nov. 26, 2008, which is 76.6 Kb in size. The information in the electronic format of the Sequence Listing is incorporated herein by reference in its entirety.

BACKGROUND OF THE INVENTION

1. Field of the Invention

The present invention relates to compositions and methods for producing plants with increased biomass.

2. Description of the Related Art

As the population of the world increases, a major goal of agricultural research is to improve the biomass yield of crop and forage plant species.

Such improvements have until recently depended on selective breeding of plants for desirable characteristics. However for many plants the heterogeneous genetic complements produced in off-spring do not result in the same desirable traits as those of their parents, thus limiting the effectiveness of selective breeding approaches.

Advances in molecular biology now make it possible to genetically manipulate the germplasm of both plants and animals. Genetic engineering of plants involves the isolation and manipulation of genetic material and the subsequent introduction of such material into a plant. This technology has led to the development of plants that are capable of expressing pharmaceuticals and other chemicals, plants with increased pest resistance, increased stress tolerance, and plants that express other beneficial traits.

Whilst it is known in the art that certain growth factors may be applied to increase plant size, the application of such growth factors is both costly and time consuming. Thus, there exists a need for plants with increased biomass relative to their cultivated counterparts.

It is an object of the invention to provide improved compositions and/or methods for developing plant varieties with altered biomass or at least to provide the public with a useful choice.

SUMMARY OF THE INVENTION

In a first aspect the invention provides a method for producing a plant with altered biomass, the method comprising transformation of a plant with a:
  a) a polynucleotide including a sequence encoding of a polypeptide with the amino acid sequence of SEQ ID NO:1 or a variant of the polypeptide; or
  b) a polynucleotide comprising a fragment, of at least 15 nucleotides in length, of the polynucleotide of a); or
  c) a polynucleotide comprising a compliment, of at least 15 nucleotides in length, of the polynucleotide of a); or
  d) a polynucleotide comprising a sequence, of at least 15 nucleotides in length, capable of hybridising to the polynucleotide of a) under stringent conditions.

Preferably the polynucleotide is included as part of a genetic construct.

In one embodiment the variant has at least 70% sequence identity to a polypeptide with the amino acid sequence of SEQ ID NO: 1.

In a further embodiment the variant comprises the amino acid sequence of SEQ ID NO: 20.

In a further embodiment the variant is derived from a plant species and comprises the amino acid sequence of SEQ ID NO: 20.

In a further embodiment the variant is derived from a dicotyledonous plant species and comprises the amino acid sequence of SEQ ID NO: 21.

Preferably the variant is capable of modulating biomass in a plant

In a further embodiment the polynucleotide of a) encodes a polypeptide with the amino acid sequence of SEQ ID NO: 1.

Preferably expression of the polynucleotide in the plant results in down-regulation of an endogenous polynucleotide/polypeptide capable of modulating biomass production in the plant.

Preferably the reduced expression is effected by antisense suppression, sense suppression or RNA interference.

Preferably the plant produced has increased biomass relative to a suitable control plant.

In a further aspect the invention provides a method for producing a plant with increased biomass, the method comprising transformation of a plant with a polynucleotide with sufficient sequence similarity to an endogenous nucleic acid encoding a polypeptide with the sequence of SEQ ID NO:1 or a variant thereof, such that expression of the polynucleotide results in inhibition of expression of the endogenous nucleic acid.

Preferably the polynucleotide is included as part of a genetic construct.

In one embodiment the variant has at least 70% sequence identity to a polypeptide with the amino acid sequence of SEQ ID NO: 1.

In a further embodiment the variant comprises the amino acid sequence of SEQ ID NO: 20.

In a further embodiment the variant is derived from a plant species and comprises the amino acid sequence of SEQ ID NO: 20.

In a further embodiment the variant is derived from a dicotyledonous plant species and comprises the amino acid sequence of SEQ ID NO: 21.

Preferably the variant is capable of modulating biomass in a plant.

In a further embodiment the polypeptide has the sequence of SEQ ID NO:1

In a further aspect the invention provides a method of producing a plant with altered biomass, the method comprising transformation of a plant cell or plant with a:
  a) a polynucleotide comprising the nucleotide sequence of SEQ ID NO:10, or a variant thereof; or
  b) a polynucleotide comprising a fragment, of at least 15 nucleotides in length, of the polynucleotide of a); or
  c) a polynucleotide comprising a complement, of at least 15 nucleotides in length, of the polynucleotide of a); or
  d) a polynucleotide comprising a sequence, of at least 15 nucleotides in length, capable of hybridising to the polynucleotide of a) under stringent conditions.

Preferably the polynucleotide is included as part of a genetic construct.

Preferably the variant encodes a polypeptide capable of modulating biomass in a plant In one embodiment the polynucleotide of a) comprises the sequence of SEQ ID NO: 10. Preferably expression of the polynucleotide in the plant results in down-regulation of an endogenous polynucleotide/polypeptide capable of modulating biomass production in the plant.

Preferably the down-regulation is effected by antisense suppression, sense suppression or RNA interference.

Preferably the plant produced by the method of the invention has increased biomass relative to a suitable control plant.

In a further aspect the invention provides a method for producing a plant with increased biomass the method comprising transformation of a plant with a polynucleotide with sufficient sequence similarity to an endogenous nucleic acid with the sequence of SEQ ID NO:10 or a variant thereof, such that in expression of the polynucleotide results in inhibition of expression of the endogenous nucleic acid.

Preferably the polynucleotide is included as part of a genetic construct.

In one embodiment the variant has at least 70% sequence identity with the full-length coding sequence of SEQ ID NO:10.

In a further embodiment the variant encodes a polypeptide comprising the amino acid sequence of SEQ ID NO: 20.

In a further embodiment the variant is derived from a plant species and encodes a polypeptide comprising the amino acid sequence of SEQ ID NO: 20.

In a further embodiment the variant is derived from a dicotyledonous plant species and encodes a polypeptide comprising the amino acid sequence of SEQ ID NO: 21.

Preferably the variant encodes a polypeptide capable of modulating biomass in a plant In a further embodiment the endogenous nucleic acid comprises the full-length coding sequence of SEQ ID NO:10.

In a further aspect the invention provides a method for producing a plant cell or plant with altered biomass, the method comprising reducing the expression or activity of a polypeptide including the amino acid sequence of SEQ ID NO: 1 or variant thereof.

In one embodiment the variant has at least 70% sequence identity to a polypeptide with the amino acid sequence of SEQ ID NO: 1.

In a further embodiment the variant comprises the amino acid sequence of SEQ ID NO: 20.

In a further embodiment the variant is derived from a plant species and comprises the amino acid sequence of SEQ ID NO: 20.

In a further embodiment the variant is derived from a dicotyledonous plant species and comprises the amino acid sequence of SEQ ID NO: 21.

In a further embodiment the polypeptide has the sequence of SEQ ID NO:1

In a further aspect the invention provides a method of producing a plant with altered biomass the method comprising the step of reducing the expression or activity in a plant cell or plant of a polypeptide comprising the sequence of SEQ ID NO: 20.

In one embodiment the polypeptide comprises the sequence of SEQ ID NO: 21.

In a further embodiment the polypeptide comprises the sequence of with at least 70% identity to the sequence of SEQ ID NO: 1.

In a further embodiment the polypeptide comprises the sequence of SEQ ID NO: 1.

In a further embodiment the a polynucleotide capable of hybridising under stringent conditions to an endogenous nucleic acid encoding the polypeptide is introduced into the plant cell or plant to effect reduced expression of the polypeptide.

In a further embodiment the endogenous nucleic acid comprises a sequence with at least 70% identity to the full-length coding sequence of SEQ ID NO: 10.

In a further embodiment the endogenous nucleic acid comprises the full-length coding sequence of SEQ ID NO: 10.

In a further embodiment the polynucleotide comprises at least 15 contiguous nucleotides of a sequence with at least 70% identity to the sequence of SEQ ID NO: 10.

In a further embodiment the polynucleotide comprises at least 15 contiguous nucleotides of SEQ ID NO: 10.

In a further aspect the invention provides a plant cell or plant produced by a method of the invention.

Preferably the plant produced by the method of the invention has increased biomass production relative to a suitable control plant.

Preferably the plant produced by the method of the invention has an increased number of tillers relative to a suitable control plant.

In a further aspect the invention provides an isolated polynucleotide having at least 71% sequence identity to a nucleotide sequence that encodes a polypeptide comprising the amino acid sequence of SEQ ID NO: 1.

Preferably the polynucleotide encodes a polypeptide capable of modulating biomass in a plant In one embodiment the polypeptide comprises the amino acid sequence of SEQ ID NO:1

In a further embodiment the nucleotide sequence comprises the sequence of SEQ ID NO:10.

In a further embodiment said nucleotide sequence comprises the full-length coding sequence of SEQ ID NO:10.

In a further aspect the invention provides an isolated polynucleotide that encodes a polypeptide comprising an amino acid sequence SEQ ID NO: 1.

In one embodiment the polynucleotide comprises the sequence of SEQ ID NO:10.

In a further embodiment the polynucleotide comprises the full-length coding sequence of SEQ ID NO:10.

In a further aspect the invention provides an isolated polynucleotide comprising the full-length coding sequence of SEQ ID NO: 10 or a variant thereof, wherein the variant is derived from ryegrass or fescue, and encodes a polypeptide capable of modulating biomass in a plant.

In one embodiment the variant has at least 70% sequence identity to the full-length coding sequence of SEQ ID NO:10.

In one embodiment the isolated polynucleotide comprises the sequence of SEQ ID NO:10.

In a further aspect the invention provides an isolated polypeptide having at least 90% sequence identity to the amino acid sequence of SEQ ID NO: 1, wherein the polypeptide is capable of modulating biomass in a plant.

In one embodiment the isolated polypeptide the amino acid sequence of SEQ ID NO: 1.

In a further aspect the invention provides an isolated polynucleotide encoding a polypeptide of the invention.

In a further aspect the invention provides an isolated polynucleotide comprising:
  a) a polynucleotide comprising a fragment, of at least 15 nucleotides in length, of a polynucleotide of the invention; or
  b) a polynucleotide comprising a complement, of at least 15 nucleotides in length, of the polynucleotide of the invention; or c) a polynucleotide comprising a sequence, of at least 15 nucleotides in length, capable of hybridising to the polynucleotide of the invention.

In a further aspect the invention provides a genetic construct which comprises a polynucleotide of the invention.

In one embodiment the genetic construct is an expression construct.

In a further aspect the invention provides a vector comprising an expression construct or genetic construct of the invention.

In a further aspect the invention provides a host cell genetically modified to express a polynucleotide of the invention, or a polypeptide of the invention.

In a further aspect the invention provides a host cell comprising an expression construct or genetic construct of the invention.

In a further aspect the invention provides a plant cell genetically modified to express a polynucleotide of the invention, or a polypeptide of the invention.

In a further aspect the invention provides a plant cell which comprises an expression construct of the invention or the genetic construct of the invention.

Preferably the expression construct is capable of expressing the polynucleotide, resulting in inhibition of expression of an endogenous polynucleotide/polypeptide which is capable of modulating biomass production in the plant.

In a further aspect the invention provides a plant which comprises a plant cell of the invention.

In a further aspect the invention provides a method for selecting a plant with altered biomass, the method comprising testing of a plant for altered expression of a polynucleotide of the invention.

In a further aspect the invention provides a method for selecting a plant with altered biomass, the method comprising testing of a plant for altered expression of a polypeptide of the invention.

In a further aspect the invention provides a plant cell or plant produced by the method of the invention.

In a further aspect the invention provides a plant selected by the method of the invention.

In a further aspect the invention provides an antibody raised against a polypeptide of the invention.

The polynucleotides and polynucleotide variants, of the invention may be derived from any species and/or may be produced recombinantly or synthetically.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonous plant species.

In a further embodiment the polynucleotide or variant, is derived from a monocotyledonous plant species.

The polypeptide and polypeptide variants, of the invention may be derived from any species and/or may be produced recombinantly or synthetically.

In one embodiment the polypeptide or variant, is derived from a plant species.

In a further embodiment the polypeptide or variant, is derived from a gymnosperm plant species.

In a further embodiment the polypeptide or variant, is derived from an angiosperm plant species.

In a further embodiment the polypeptide or variant, is derived from a from dicotyledonous plant species.

In a further embodiment the polypeptide or variant, is derived from a monocotyledonous plant species.

The plant cell or plant may be derived from any plant species.

In a further embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred dicotyledonous genera include: *Amygdalus, Anacardium, Arachis, Brassica, Cajanus, Cannabis, Carthamus, Carya, Ceiba, Cicer, Cocos, Coriandrum, Coronilla, Cossypium, Crotalaria, Dolichos, Elaeis, lycine, Gossypium, Helianthis, Lathyrus, Lens., Lespedeza, Linum, Lotus, Lupinis, Macadaia, Medicago, Melilotus, Mucuna, Olea, Onobrychis, Ornithopus, Papaver, Phaseolis, Phoenix, Pistacia, Pisum, Prunus, Pueraria, Ribes, Ricinis, Sesamum, Theobroma, Trifolium, Trigonella, Vicia* and *Vigna*.

Preferred dicotyledonous species include: *Amygdalus communis, Anacardium occidentale, Arachis hypogaea, Arachis hypogea, Brassica napus Rape, Brassica. nigra. Brassica campestris, Cajanus cajan, Cajanus indicus. Cannabis sativa, Carthamus tinctorius, Carya illinoinensis, Ceiba pentandra, Cicer arietinum, Cocos nucifera, Coriandrum sativum, Coronilli varia, Cossypium hirsutum, Crotalaria juncea, Dolichos lablab, Elaeis guineensis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus corniculatus, Lipinus albus, Medicago arborea, Medicago falcate, Medicago hispida, Medicago officinalis, Medicago. sativa Alfalfa, Medicago tribuloides, Macadamia integrifolia. Medicago arabica, Melilotus albus, Mucuna pruriens, Olea europaea, Onobrychis viciifolia, Ornithopus sativus, Phaseolus aureus, Prunus cerasifera, Prunus cerasus, Phaseolus coccineus, Prunus domestica, Phaseolus lunatus, Prunus. maheleb, Phaseolus mungo, Prunus. persica, Prunus. pseudocerasus, Phaseolis vulgaris. Papaver somniferum. Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communic, Sesamum indicum, Trifolium augustifolium. Trifolium diffusum, Trifolium hybridum. Trifolium incarnatum, Trifolium ingrescens, Trifolium pratense, Trifolium repens, Trifolium resupinatum, Trifolium subterraneum, Theobroma cacao, Trifolium alexandrinum, Trigonella foenumgraecum, Vicia angustifolia, Vicia atropurpurea, Vivia calcarata, Vicia dasycarpa, Vicia ervillia, Vaccinium oxycoccos, Vicia pannonica, Vigna sesquipedalis, Vigna sinensis, Vicia villosa, Vicia faba, Vicia sative* and *Vigna angularis*.

Preferred monocotyledonous genera include: *Agropyron, Allium, Alopecuris, Andropogon, Arrhenatherum, Asparagus, Avena, Bambusa, Bothrichloa, Bouteloua, Bromus, Calamovilfa, Cenchrus, Chloris, Cymbopogon, Cynodon, Dactylis, Dichanthium, Digitaria, Eleusine, Eragrostis, Fagopyrum, Festuca, Helianthus, Hordeum, Lolium, Miscanthis, Miscanthus×giganteus, Oryza, Panicum, Paspalum, Pennisetum, Phalaris, Phleum, Poa, Saccharum, Secale, Setaria, Sorgahastum, Sorghum, Triticum, Vanilla, X Triticosecale Triticale* and *Zea*.

Preferred monocotyledonous species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium. fistulosum, Allium. sativum, Alopecurus pratensis, Andropogon gerardi, Andropogon Gerardii, Andropogon scoparious, Arrhenatherum elatius, Asparagus officinalis, Avena nuda, Avena sativa, Bambusa vulgaris, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Cenchriis ciliaris, Chloris gayana, Cymbopogon nardus, Cynodon dactylon, Dactylis glomerata, Dichanthium annulatum, Dichanthium aristatum, Dichanthium sericeum, Digitaria decumbens, Digitaria smutsii, Eleusine coracan, Elymus angustus, Elymus junceus, Eragrostis curvula, Eragrostis tef, Fagopyrum esculentum, Fagopyrum taricum, Festuca arundinacea, Festuca ovina, Festuca pratensis, Festuca rubra, Helianthus annus sunflower, Hordeum distichum, Hordeum vulgare, Lolium multiflorum, Lolium perenn, Miscanthis sinensis, Miscanthus×giganteus, Oryza sativa, Panicum italicium, Panicum maximum, Panicum miliaceum, Panicum purpurascens, Panicum virgatum, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa. nemoralis, Saccharum officinarum, Saccharum robustum, Saccharum sinense, Saccharum spontaneum, Secale cereale, Setaria sphacelata, Sorgahastum nutans, Sorghastrum nutans, Sorghum dochna, Sorghum halepense, Sorghum sudanense, Sorghum vulgare, Sorghum vulgare, Triticum aestivum, Triticum dicoccum, Triticum durum, Triticum monococcum, Vanilla fragrans, X Triticosecale* and *Zea mays*.

Preferred plants are forage plant species from a group comprising but not limited to the following genera: *Lolium, Festuca, Dactylis, Bromus, Trifolium, Medicago, Phleum, Phalaris, Holcus, Lotus, Plantago* and *Cichorium*.

Particularly preferred plants are from the genera *Lolium* and *Trifolium*. Particularly preferred species are *Lolium perenne* and *Trifolium repens*.

Particularly preferred monocotyledonous plant species are: *Lolium perenne* and *Oryza sativa*.

The term "plant" is intended to include a whole plant, any part of a plant, propagules and progeny of a plant.

The term 'propagule' means any part of a plant that may be used in reproduction or propagation, either sexual or asexual, including seeds and cuttings.

DETAILED DESCRIPTION OF THE PREFERRED EMBODIMENT

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques.

The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides and polypeptides of the invention being "derived from" a particular genera or species, means that the polynucleotide or polypeptide has the same sequence as a polynucleotide or polypeptide found naturally in that genera or species. The polynucleotide or polypeptide which is derived from a genera or species may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polynucleotides possess biological activities that are the same or similar to those of the inventive polypeptides or polynucleotides. The term "variant" with reference to polypeptides and polynucleotides encompasses all forms of polypeptides and polynucleotides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, preferably at least 50 nucleotide positions, more preferably at least 100 nucleotide positions, and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Use of BLASTN as described above is preferred for use in the determination of sequence identity for polynucleotide variants according to the present invention.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1 \times 10^{-10}$ more preferably less than $1 \times 10^{-20}$, more preferably less than $1 \times 10^{-30}$, more preferably less than $1 \times 10^{-40}$, more preferably less than $1 \times 10^{-50}$ more preferably less than $1 \times 10^{-60}$ more preferably less than $1 \times 10^{-70}$, more preferably less than $1 \times 10^{-80}$ more preferably less than $1 \times 10^{-90}$ and most preferably less than $1 \times 10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press;

Ausubel et al., 1987, Current Protocols in Molecular Biology, Greene Publishing,). Tm for polynucleotide molecules greater than about 100 bases can be calculated by the formula Tm=81.5+0.41% (G+C-log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp://ftp.ncbi.nih.gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least %, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/). The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$ more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g., (5')GATCTA.......TAGATC(3')

(3')CTAGAT.......ATCTAG(5')

Read-through transcription will produce a transcript that undergoes complementary base-pairing to form a hairpin structure provided that there is a 3-5 bp spacer between the repeated regions.

A "transgenic plant" refers to a plant which contains new genetic material as a result of genetic manipulation or transformation. The new genetic material may be derived from a plant of the same species as the resulting transgenic plant or from a different species.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The term "biomass" refers to the size and/or mass and/or number of vegetative organs of the plant at a particular age or developmental stage. Thus a plant with increased biomass has increased size and/or mass and/or number of vegetative organs than a suitable control plant of the same age or at an equivalent developmental stage. Conversely, a plant with decreased biomass has decreased size and/or mass and/or number of vegetative organs than a suitable control. Altered biomass may also involve an alteration in rate of growth and/or rate of formation of vegetative organs during some or all periods of the life cycle of a plant relative to a suitable control. Thus altered biomass may result in an advance or delay in the time taken for such a plant to reach a certain developmental stage.

Suitable control plants may include non-transformed plants of the same species and variety, or plants of the same species or variety transformed with a control construct.

The invention provides methods for producing and selecting plants with altered biomass relative to suitable control plants, including plants with both increased and decreased biomass and plants produced by such methods.

The invention provides a polynucleotide (SEQ ID NO:10) encoding a polypeptide (SEQ ID NO:1) which modulates biomass in plants. The invention provides polynucleotide variants of SEQ ID NO:10 (SEQ ID NOs: 11 to 18) which encode polypeptide variants of SEQ ID NO:1 (SEQ ID NO:2 to 9). The applicants have also identified a consensus polypeptide sequence motif present in SEQ ID NO:1 and all of the polypeptide variants of SEQ ID NO:1, as shown in SEQ ID NO:20, and a further consensus motif (SEQ ID NO: 21) present in SEQ ID NO:1 (ORF54) and all polypeptide variants thereof that are derived from dicotyledonous plants.

Methods for Isolating Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention, or polynucleotides useful in methods of the invention, include use of all, or portions of, the polynucleotides set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full-length polynucleotide sequence. Such methods include PCR-based methods, 5' RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser). Typically, the polynucleotide sequence of a primer, useful to amplify variant polynucleotide molecules by PCR, may be based on a sequence encoding a conserved region of the corresponding amino acid sequence.

Alternatively library screening methods will be known to those skilled in the art (Sambrook et al., Molecular Cloning: A Laboratory Manual, 2nd Ed. Cold Spring Harbor Press, 1987) may be employed. When identifying variants of the probe sequence hybridisation and/or wash stringency conditions will typically be reduced relative to when exact sequence matches are sought.

Polypeptide variants of the invention may be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification,*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Host cells of the invention may also be useful in methods for production of an enzymatic product generated by an expressed polypeptide of the invention. Such methods may involve culturing the host cells of the invention in a medium suitable for expression of a recombinant polypeptide of the invention, optionally in the presence of additional enzymatic substrate for the expressed polypeptide of the invention. The enzymatic product produced may then be separated from the host cells or medium by a variety of art standard methods.

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Production of plants altered in biomass may be achieved through methods of the invention. Such methods may involve the transformation of plant cells and plants, with a construct of the invention designed to alter expression of a polynucleotide or polypeptide capable of modulating biomass production in such plant cells and plants. Such methods also include the transformation of plant cells and plants with a combination of the construct of the invention and one or more other constructs designed to alter expression of one or more polypeptides or polypeptides capable of modulating biomass production in such plant cells and plants.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants.

Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

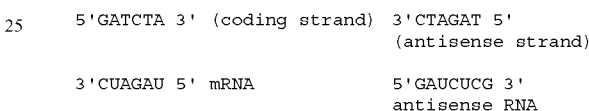

Genetic constructs designed for gene silencing may also include an inverted repeat. An 'inverted repeat' is a sequence that is repeated where the second half of the repeat is in the complementary strand, e.g.,

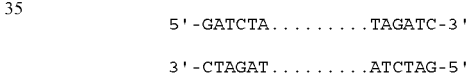

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides useful for effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al, 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257).

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); alfalfa (Weeks et al., (2008) Transgenic Research 17: 587-597; Samac et al., (2006) Methods Mol Biol, Vol 343, *Agrobacterium* Protocols. 2nd edition. Totowa, N. J.: Humana Press. p 301-311.); and cereals (U.S. Pat. No. 6,074,877). Other species are contemplated and suitable methods and protocols are available in the scientific literature for use by those skilled in the art.

Several further methods known in the art may be employed to alter expression of a nucleotide and/or alter expression or activity of a polypeptide of the invention, or used in a method of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phage-display (Dyax Corporation).

Such interacting peptides may be expressed in or applied to a plant to affect activity of a polypeptide of the invention. Plantibodies (Stoger et al., Current Opinion in Biotechnology Volume 13, Issue 2, 1 Apr. 2002, Pages 161-166; Sudarshana et al., Methods Mol. Biol. 2007; 354:183-95.) may also be used to modulate expression or activity of a polypeptide in a plant. Use of each of the above approaches, including the silencing methods discussed, in alteration of expression of a nucleotide and/or expression or activity of a polypeptide of the invention is specifically contemplated.

Methods for Selecting Plants

Methods are also provided for selecting plants with altered biomass. Such methods involve testing of plants for altered for the expression of a polynucleotide or polypeptide of the invention. Such methods may be applied at a young age or early developmental stage when the altered biomass may not necessarily be visible, to accelerate breeding programs directed toward improving biomass.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered biomass. The polypeptides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate biomass in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered biomass.

Plants

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

It may be desirable to either increase or decrease biomass in a particular plant species. Increased biomass would be advantageous for example in human food, forage and forestry crops as well as in ornamental plants. Decreased biomass may also be desirable in certain of the above cases, for example in the miniaturization of ornamental plants.

Biomass in a plant may also be altered through methods of the invention. Such methods may involve the transformation of plant cells and plants, with a construct of the invention designed to alter expression of a polynucleotide or polypeptide which modulates biomass in such plant cells and plants. Such methods also include the transformation of plant cells and plants with a combination of the construct of the invention and one or more other constructs designed to alter expression of one or more polynucleotides or polypeptides which modulates biomass in plants.

Exemplary methods for assessing growth rate and biomass in plants of the invention are provided in Boyes D C et al., 2001, Plant Cell. 13(7):1499-510; Lancashire P. D et al., 1991, Ann. Appl. Biol. 119: 560-601, and in Example 1 below.

BRIEF DESCRIPTION OF THE DRAWINGS

The present invention will be better understood with reference to the accompanying drawings in which:

FIG. 1 shows the summary output of a BLAST-P search of the NR-PLANT database (release date 1 Jan. 2005) in which the ORF54 polypeptide (SEQ ID NO:1) was used as a seed sequence.

FIG. 2 shows PrettyPlot alignment of polypeptides (SEQ ID NO: 1 to 9), including ORF54 and variants thereof FIG. 3 shows a "T-COFFEE" alignment of the seven repeat elements, termed RCC repeats, found in the polypeptide sequences (SEQ ID NO: 1 to 9) as used by the applicants to identify a consensus region (SEQ ID NO: 10) present in each repeat of all the sequences.

FIG. 7 shows an alignment of the ORF54 polypeptide and variants thereof from monocotyledonous species. Highlighting shows the position a consensus sequence motif (SEQ ID NO: 20) completely conserved in all of the sequences.

FIG. 8 shows an alignment of the ORF54 polypeptide and variants thereof from dicotyledonous species. Highlighting shows the position a consensus sequence motif (SEQ ID NO: 21) completely conserved in all of the sequences.

EXAMPLES

The invention will now be illustrated with reference to the following non-limiting examples.

Example 1

Increased Biomass by Down Regulation of a Polynucleotide of the Invention in Transgenic Plants

ORF54

A polynucleotide sequence designated ORF54 (SEQ ID NO: 10), encoding the polypeptide of SEQ ID NO: 1, was identified in a ViaLactia Biosciences Ltd proprietary ryegrass (*Lolium perenne*) GeneThresher (Orion Genomics) genomic library.

ORF54 Variants

The polypeptide sequence of ORF54 (SEQ ID NO:1) was used as a seed sequence to perform a BLASTP search against the NR-Plant database (release date 2005 Jan. 1) to identify variants of ORF54. A cut-off value of less than or equal to 1e-140 was identified as distinguishing ORF54 variants based upon the applicant's assessment of the associated score value and annotations in the public data base. The BLASTP output summary is shown in FIG. 1.

The selected variant sequences were aligned using the EMBOSS tool EMMA (Thompson et al 1994), which is an interface to the popular multiple alignment program ClustalW. Aligned sequences were visualised using another EMBOSS tool called prettyplot as shown in FIG. 2.

The polypeptide sequences of ORF54 variants are listed as SEQ ID NO:2 to 9 in the sequence listing. The corresponding polynucleotide sequences are listed as SEQ ID NO:11 to 18 respectively.

Analysis of the polypeptide sequences revealed the presence of seven repeats per polypeptide sequence and the repeat sequences are termed RCC repeats. The repeat sequences from all polypeptides (SEQ ID NO:1-9) above were aligned using the T-COFFEE alignment programme Version_1.37 (Notredame et. al 2000, Higgins) and the outcome is presented in FIG. 3.

A polypeptide motif based on, and present in, all of the RCC repeats from ORF54 and each of the ORF54 variants was identified and is represented in FIG. 3.

A Vector Comprising ORF54

Figure 4:
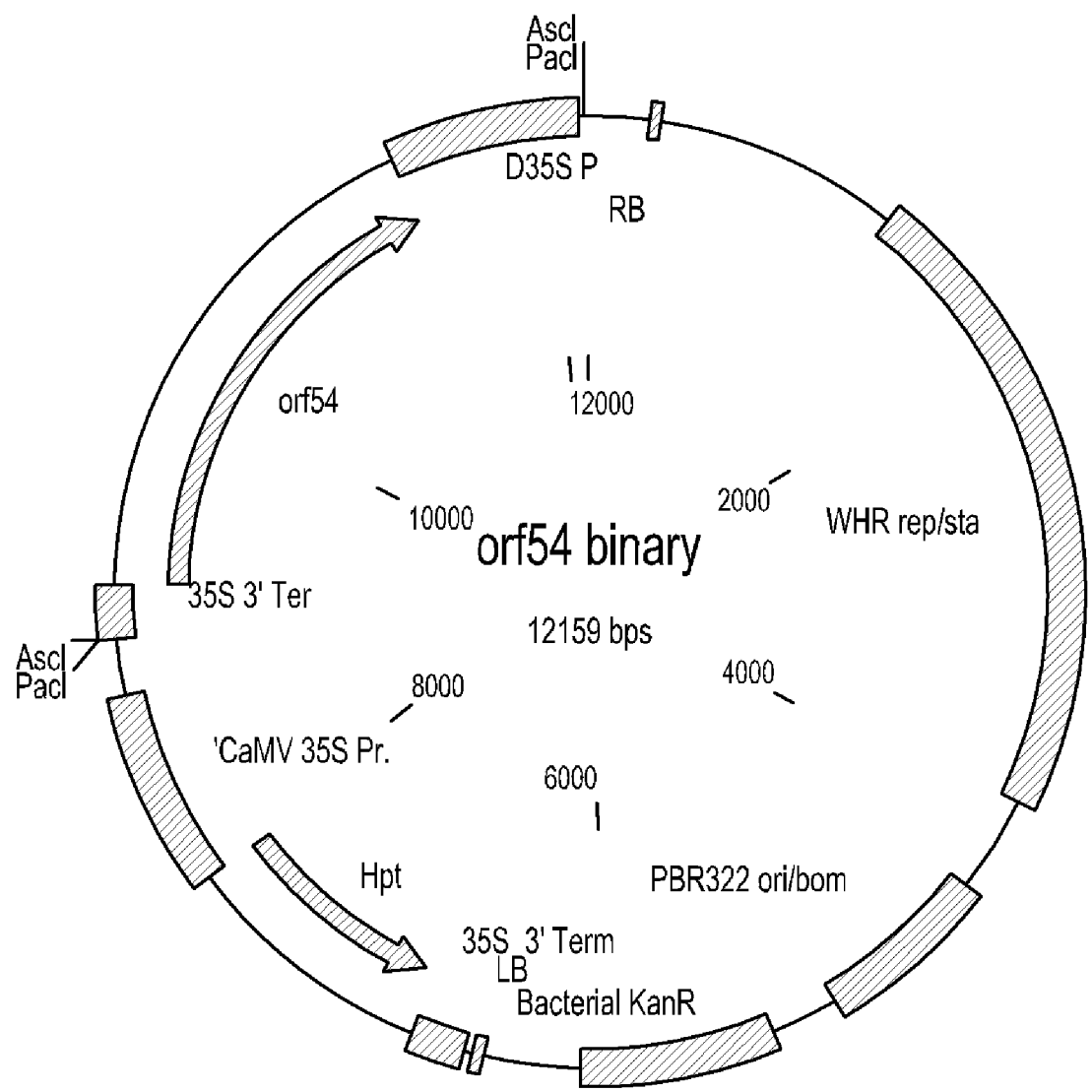
FIG. 4 shows a map of a vector, for plant transformation, comprising ORF54 cloned in antisense orientation relative to the CaMV 35S promoter. The sequence of the vector is represented in SEQ ID NO:20.

The ORF54 polynucleotide sequence (SEQ ID NO:10) was cloned in the anti-sense orientation upstream of the double 35S promoter in order to down-regulate expression of the ORF54 homologue in rice. The vector comprising ORF54 was produced by standard molecular biology techniques. A map of the binary vector is shown in FIG. 4. The sequence of the vector is represented in SEQ ID NO:19.

Plant Transformation—Rice

The purified binary vector (SEQ ID NO:19) was introduced into *Agrobacterium* strain EHA105 by electroporation (den Dulk-Ras A and Hooykaas P J.) and the suspension was incubated at 26° C. for 30 minutes. A small aliquot was plated on AB minimal medium (Schmidt-Eisenlohr et. al 1999) containing Kanamycin at 100 mg/L. Plates were incubated at 26° C. for 3 days and single colonies were tested for presence of the plasmid using construct specific primers and transformation confirmed.

*Agrobacterium* cultures were grown in AG minimal medium containing 100 mg/L kanamycin at 26° C. with shaking (200 rpm). The *Agrobacterium* suspensions were pelleted at 5,000 rpm for 5 minutes, washed once in basal MS medium containing 1% glucose and 3% sucrose, pH 5.2, and re-suspended in same medium containing 200 μM acetosyringone to $OD_{600}$ 0.6-0.8.

Figure 5:
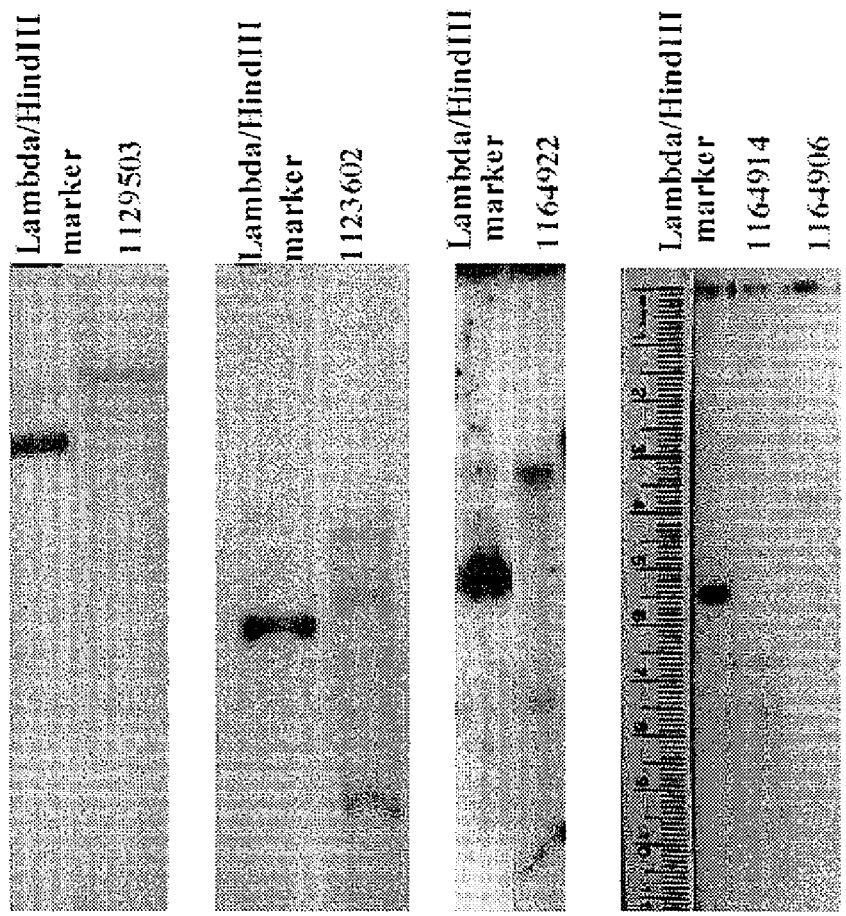
FIG. 5 shows a DNA gel-blot analysis on genomic DNA from ORF54 T0 transgenic plants digested with HindIII and probed with a fragment of ORF54 coding sequence to determine gene copy number and to identify independent transformation events.

*A. tumefaciens* containing the binary vector ORF54 were used to co-cultivate at least 1,000 immature rice (*Oryza sativa*) cv. Nipponbare embryos. Immature seeds from rice were washed in sterile water and then surface sterilized with sodium hypochlorite containing 1.25% active chlorine with 10 μL Tween® 20 for 20 minutes. After sterilization, the seeds were washed several times with sterile water and blotted dry on sterile filter paper (3M). The seeds were de-husked manually using sterile pair of forceps and the embryo dissected out with sterile knife. The isolated embryos were immersed in *Agrobacterium* suspension for 30 minutes with continuous shaking at 100 rpm in a 10 mL culture tube. The excess liquid was drained off and the embryos blotted on to sterile filter paper before placing them on to co-cultivation medium containing MS medium (Murashige and Skoog, 1964) supplemented with 3% sucrose, 1% glucose, 2 mg/L 2,4-D, 0.1 mg/L BA, 400 μM acetosyringone, pH 5.2 for 4 days in dark. After co-cultivation, the calli forming embryos were sub-cultured once every two weeks on selection medium consisting of MS medium supplemented with 3% sucrose, 1% glucose, 2 mg/L 2,4-D (2,4-dichlorophenoxy acetic acid), 0.1 mg/L BA (benzyl adenine) and containing 50 mg/L hygromycin and 300 mg/L Timentin™ (ticarcillin+clavulanic acid) till at-least 30 healthy calli showing green spots indicative of healthy shoot emergence was achieved. Calli containing the green spots were transferred to selection medium lacking 2,4-D to regenerate a minimum of 10 transformed plants. Regenerated plants were rooted and then transplanted to six inch pots containing soil and plants grown in greenhouse. DNA gel-blot analysis was carried out (FIG. 5) by digesting genomic DNA from transgenic plants with HindIII and probing with a fragment of ORF54 coding sequence to determine gene copy number and to identify five independent transformation events. T1 seeds were harvested from the transformed plants (T0).

T1 Plant Phenotyping

Thirty seeds from Southern positive T0 plants were sown in individual cups containing cocopeat and twenty healthy plants out of them were transplanted in the green house. These plants were arranged using a CRD using the random numbers from a random table.

T1 plant phenotyping was carried out in two separate experiments. The first experiment involved progeny lines from T0 events 1129503 and 123602 and Nipponbare (a wild-type control), and the second experiment involved progeny lines from T0 events 1164906, 1164914 and 1164922 and Nipponbare (a wild-type control.)

Phenotypic Analysis of T1 Lines

Figure 5A:
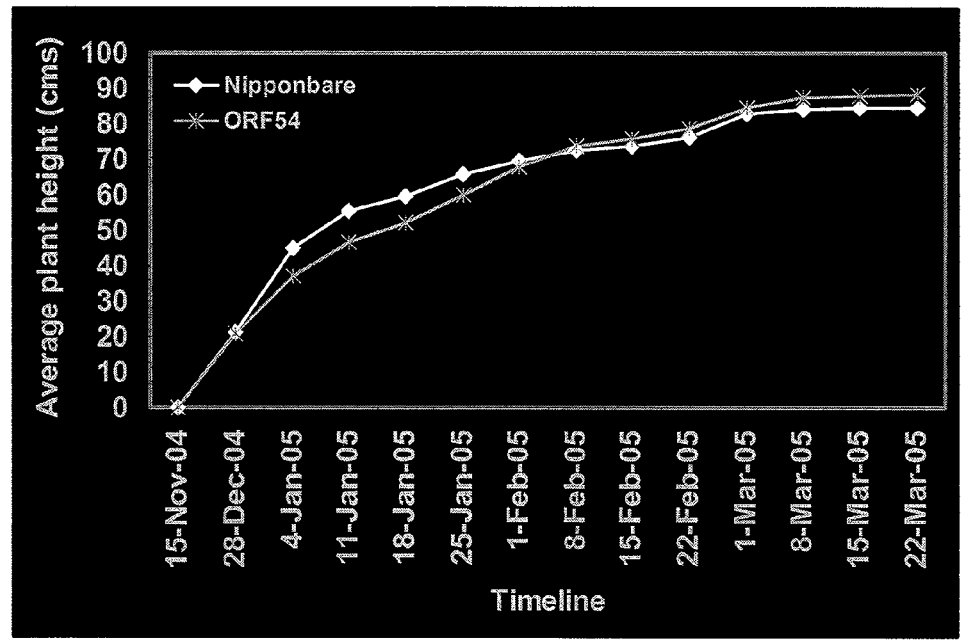
FIG. 5a-5e show growth parameters observed for these ORF54 T1 plant lines compared to the best performing wild type control (Nipponbare) in two separate experiments. Where FIG. 5a Plant height measurements from Experiment 1, FIG. 5b Plant tiller number from Experiment 1, FIG. 5c Tiller number in ORF54 lines that exceeded the tillering capacity in the best performing wild-type control (Nipponbare), FIG. 5d Plant height measurements from Experiment 2 and FIG. 5e Plant tiller number from Experiment 2.
Figure 5B:
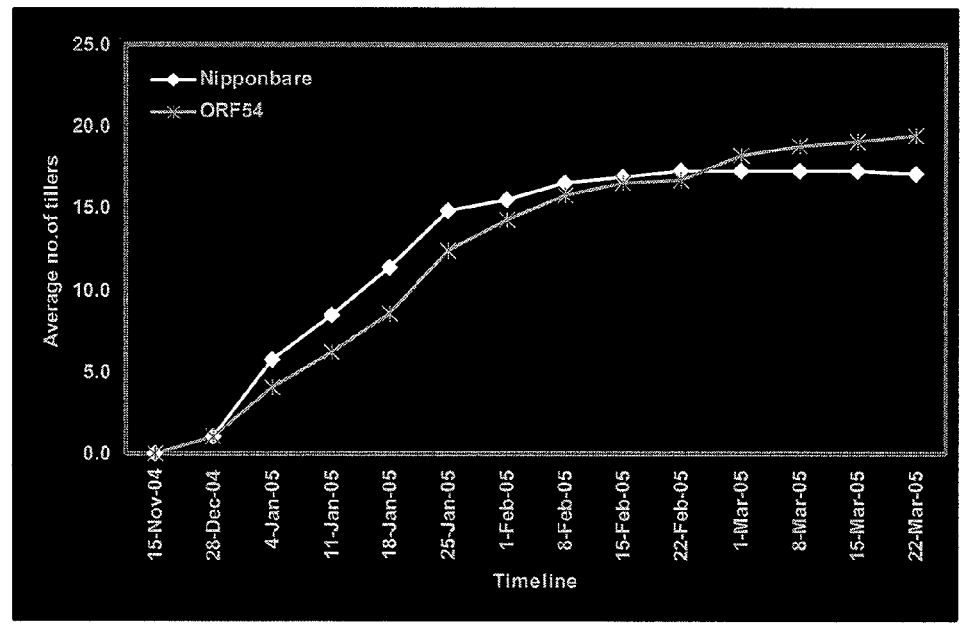
Figure 5C:
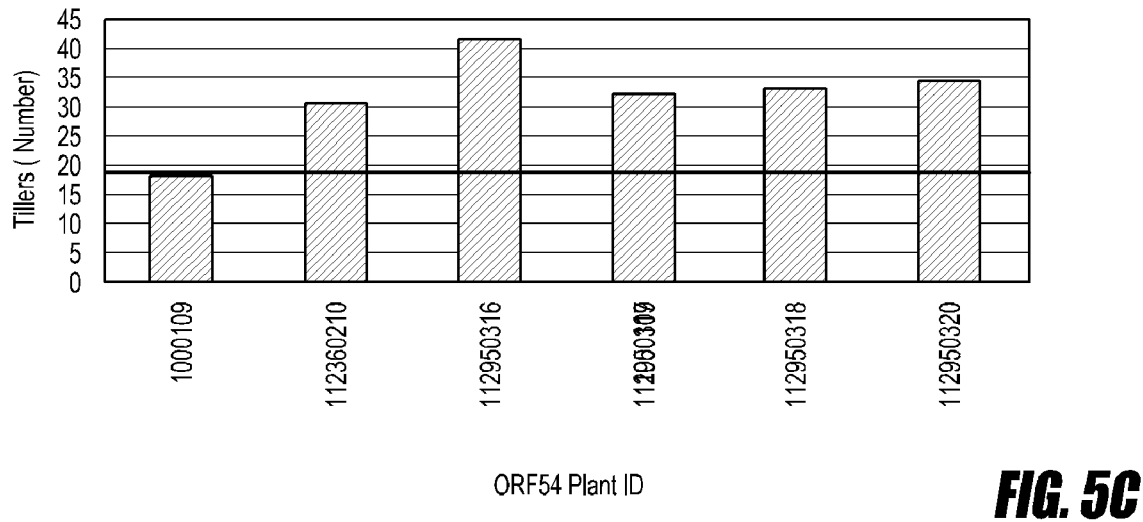
Figure 5D:
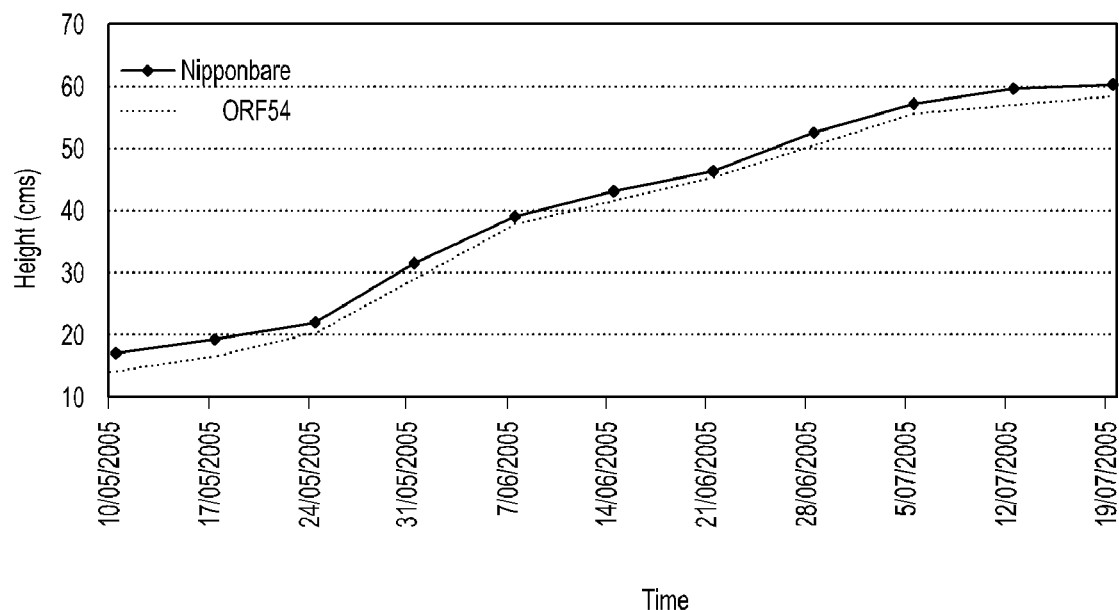
Figure 5E:
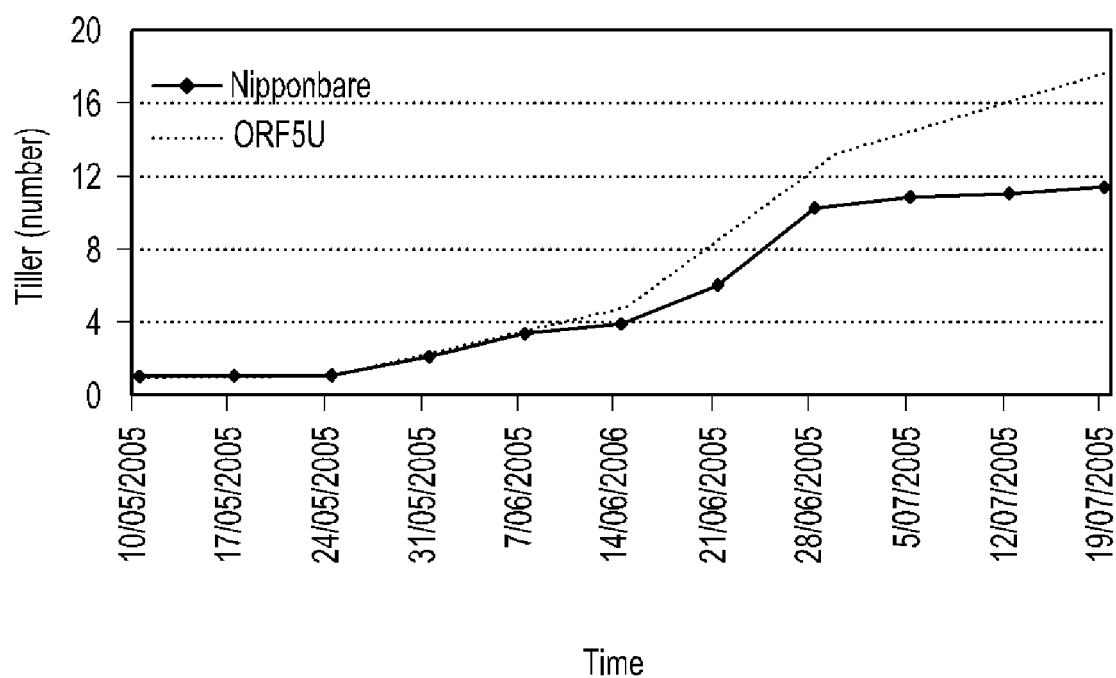
Figure 6A:
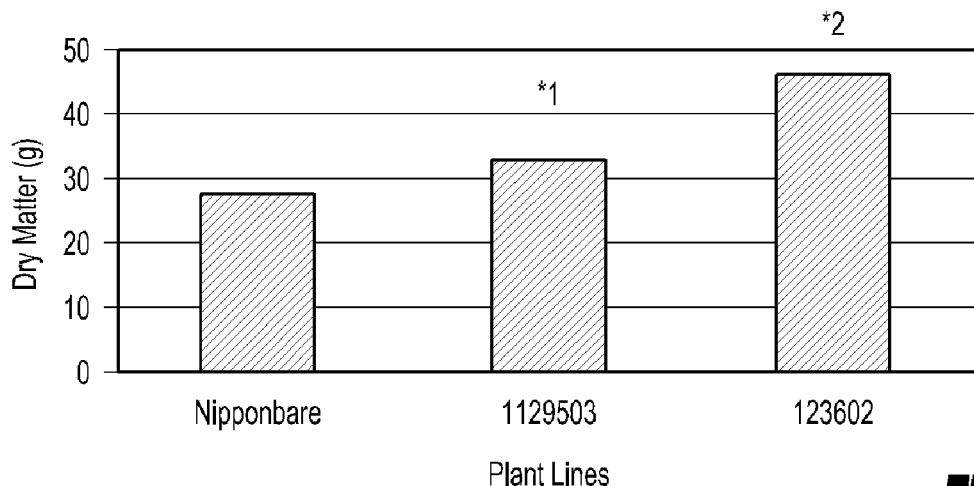
FIG. 6a shows shoot biomass analysis between ORF54 plants and wild-type control (Nipponbare). Student's t-test: *1 Mean differences between sample and Nipponbare is highly significant (p–0.01). *2 Mean differences between sample and Nipponbare is very highly significant (p=0.001).
Figure 6B:
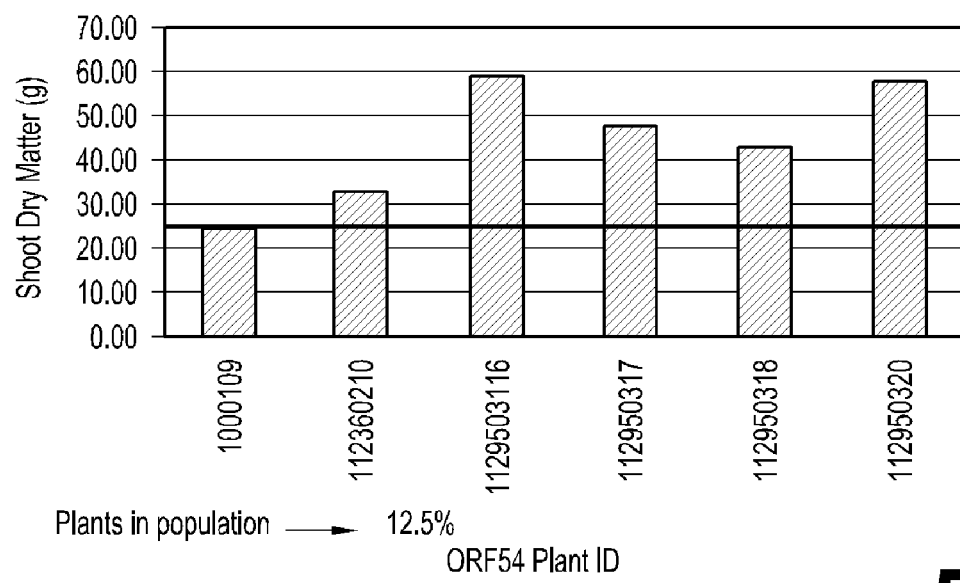
FIG. 6b shows dry matter yield in ORF54 lines that exceeded the dry matter yielding capacity in the best performing wild-type control (Nipponbare).

Plants height and tiller numbers were measured once every week post-transplanting until seed set was achieved. FIGS. 5a, b, c, d and e depict the growth parameters observed for these plants in two separate experiments. Transgenic ORF54 plants (T1) do not appear to be too different from the wildtype control (Nipponbare) in terms of plant height (FIGS. 5a and d). However tillering capacity of ORF54 plants (T1) appear to be higher than in the wild-type control (Nipponbare) (FIGS. 5b and e). A closer analysis revealed that 12.5% of the ORF54 T1 plants had out-performed the best tillering wild-type control plant (FIG. 5c) with tiller numbers more than doubling. As a result, the biomass as measured by dry matter production in ORF54 plants (T1) also increased (FIG. 6a). On an average, the increase in biomass amounts to roughly 66% as compared to the wild-type control (Nipponbare). Once again 12.5% of the ORF54 T1 plant population was seen to produce more dry matter than the highest dry matter yielding wild-type control (Nipponbare) (FIG. 6b). In conclusion down-regulation of ORF54 gene expression, or that of variants of ORF54, in planta by anti-sense or similar technology leads to an increase plant biomass.

Plant Transformation—Ryegrass

Perennial ryegrass (*Lolium perenne* L. cv. Impact) was transformed essentially as described in Bajaj et. al. (Plant Cell Reports, 2006, 25: 651-659). Embryogenic callus derived from mersitematic regions of the tillers of selected ryegrass lines and *Agrobacterium tumefaciens* strain EHA101 carrying a modified binary vector (ORF54, FIG. 4) was used for transformation experiments. Embryogenic calli were immersed with overnight-grown *Agrobacterium* cultures for 30 minutes with continuous shaking. Calli resistant to hygromycin were selected after sub-culturing them on co-cultivation medium for 4 weeks. After selection, the resistant calli were sub-cultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup. Eighteen independent transgenic lines (1V1, 1V3, 1V5, 1V8, 1V10, 1V11, 1V20, 2V2, 2V4, 2V5, 2V7, 2V8, 2V9, 3V5, 3V7, 3V10, 3V11, 3V12) and their non-transgenic control plants (T40, T41 and T101, respectively) have been analyzed in a climate-controlled environmental laboratory, where they were assessed for biomass production under fully water condition.

Screening for Increased Biomass in Growth Chamber

A plant growth system was built using 500 mm long; 90 mm diameter plastic storm-water pipes. The pipes were placed on a mobile tray and supported at the sides by ropes and metal frame. The tubes were plugged at the bottom with rockwool and progressively filled with washed mortar sand using water to achieve uniform packing. At the center of the open end of each tube a clump of perennial ryegrass (5 tillers) was planted. Plants from each event were replicate-planted in three tubes. The plants were arranged at random, one in each of the three replicates, and grown at 70% relative humidity; 16/8 hours day/night cycle and under 650 $\mu mol \cdot m^{-2} \cdot s^{-1}$ light intensity. The plants were irrigated daily once in the morning with 50 mL Hoagland's solution (Hoagland and Arnon, 1938) and again in the afternoon with 50 mL plain water. The plants were acclimated initially for twenty days and then the plants were trimmed back to 15 cm height. All plants were allowed to recover from trimming for the next fourteen days. Plant tiller numbers were recorded after seven and 14 days, respectively from the timed day. After fourteen days, plants were trimmed down to 15 cm height. The harvested samples were dried down at 60° C. for three days and then dry weight recorded. The plants were allowed to grow under fully watered conditions for another fourteen days. Again, the plants were trimmed back to 15 cm height and then the dry weight of the trimmed sample recorded after drying the samples at 60° C. for three days. The plants were allowed to grow for another 13 days and the final data on biomass production (dry matter) recorded by harvesting the plants above 15 cm and drying the samples at 60° C. for three days.

Figure 9:
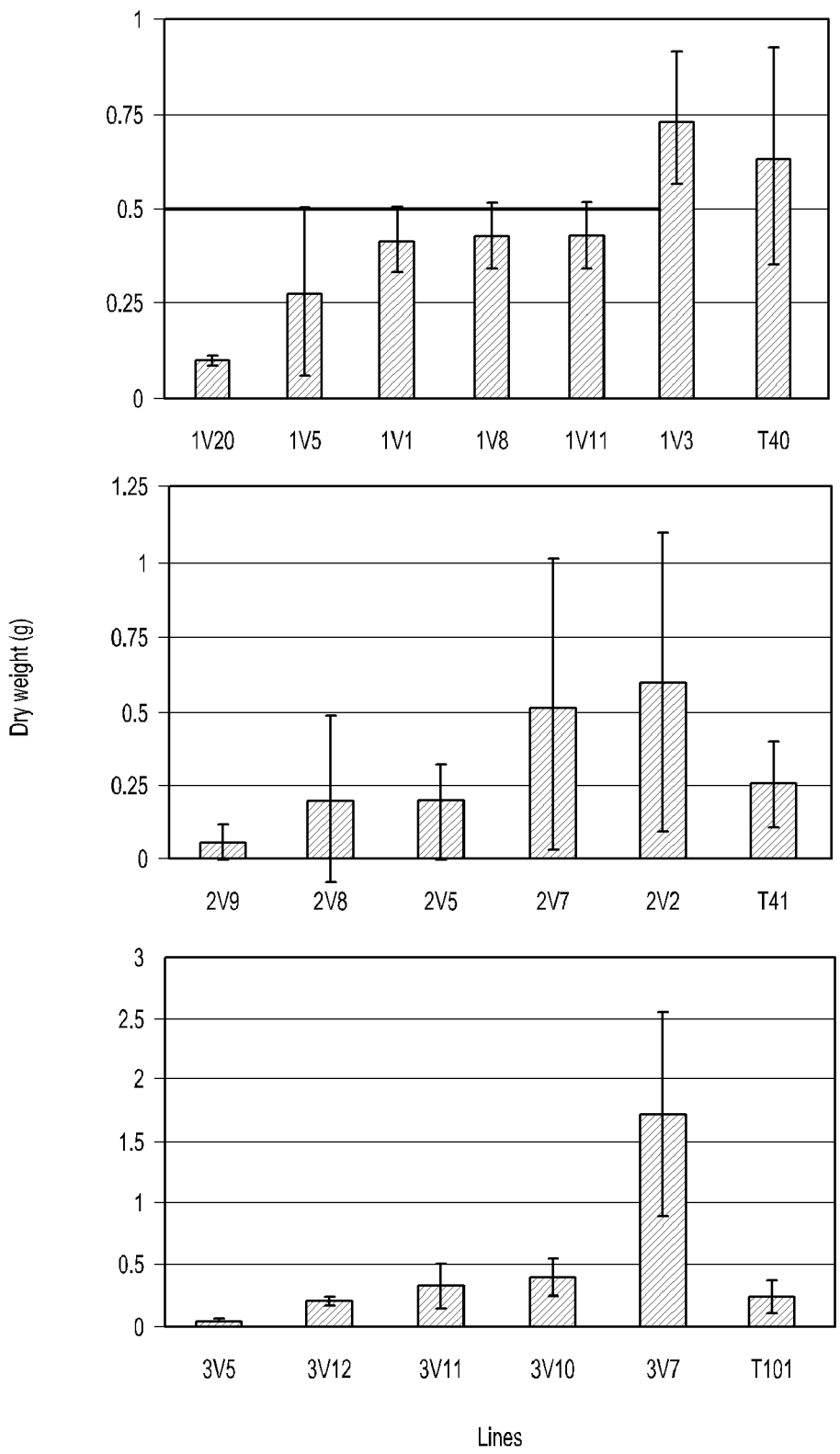
FIG. 9 shows altered biomass (dry weight in grams) in the transgenic ryegrass lines (1V20, 1V5, 1V1, 1V8, 1V11, 1V3, 2V9, 2V8, 2V5, 2V7, 2V2, 3V5, 3V12, 3V11, 3V10 and 3V7) over the non-transgenic control lines (T40, T41 and T101) bars over the columns represent standard deviation.

More than one-fourth of the transgenic events tested produced more biomass than wild type plants in each of the harvest. When cumulative growth was determined over a period of three harvests, one of the transgenic line, 3V7, produced more than 470% biomass; while in four other lines, 2V2; 2V7; and 3V10 the biomass increase ranged from over 35% to 95% (see FIG. 9).

The above examples illustrate practice of the invention. It will be appreciated by those skilled in the art that numerous variations and modifications may be made without departing from the spirit and scope of the invention.

REFERENCES

Adams et al. 1991, *Science* 252:1651-1656.
Chen H, Nelson R S, Sherwood J L. (1994) Biotechniques; 16 (4): 664-8, 670.
Chen et al. 2002, *Nucleic Acids Res.* 31:101-105
den Dulk-Ras A, Hooykaas P J. (1995) Methods Mol. Biol.; 55: 63-72.
Lee et al. 2003, *PNAS* 99:12257-12262
Lee and Lee, 2003 *Plant Physiol.* 132: 517-529
Murashige T, Skoog F (1962) Physiol Plant 15: 473-497
Notredame C., Higgins, D. and Heringa, J. (2000) J. Mol. Biol., 302, 205-217.

Richmond and Somerville 2000, *Current Opinion in Plant Biology.* 3:108-116

Ruan et al. 2004, *Trends in Biotechnology* 22: 23-30.

Schmidt-Eisenlohr H, Domke N, Angerer C, Wanner G, Zambryski P C, Baron C. (1999) J. Bacteriol.; 181 (24): 7485-92.

Sun et al. 2004, *BMC Genomics* 5: 1.1-1.4

Thompson, J. D., Higgins, D. G. and Gibson, T. J. (1994) CABIOS, 10, 19-29.

Velculescu et al. 1995, *Science* 270: 484-487

The above examples illustrate practice of the invention. It will be appreciated by those skilled in the art that numerous variations and modifications may be made without departing from the spirit and scope of the invention.

Summary of Sequences

| SEQ ID NO: | TYPE | SPECIES | REFERENCE | FULL-LENGTH CODING SEQUENCE (NUCLEOTIDES) |
| --- | --- | --- | --- | --- |
| 1 | Polypeptide | *Lolium perenne* | ORF54 | N/A |
| 2 | Polypeptide | *Oryza sativa* | AK098904.1 | N/A |
| 3 | Polypeptide | *Oryza sativa* | AK065041.1 | N/A |
| 4 | Polypeptide | *Oryza sativa* | AK065992.1 | N/A |
| 5 | Polypeptide | *Oryza sativa* | AK065747.1 | N/A |
| 6 | Polypeptide | *Oryza sativa* | AK062069.1 | N/A |
| 7 | Polypeptide | *Oryza sativa* | XP466543.1 | N/A |
| 8 | Polypeptide | *Arabidopsis thaliana* | BAB01075.1 | N/A |
| 9 | Polypeptide | *Arabidopsis thaliana* | AAL15211.1/ AAK59536.1 | N/A |
| 10 | Polynucleotide | *Lolium perenne* | ORF54 | Start 302; End 1904 |
| 11 | Polynucleotide | *Oryza sativa* | AK098904.1 | Start 326; End 1928 |
| 12 | Polynucleotide | *Oryza sativa* | AK065041.1 | Start 326; End 1928 |
| 13 | Polynucleotide | *Oryza sativa* | AK065992.1 | Start 136; End 1738 |
| 14 | Polynucleotide | *Oryza sativa* | AK065747.1 | Start 486; End 2161 |
| 15 | Polynucleotide | *Oryza sativa* | AK062069.1 | Start 2; End 1004 |
| 16 | Polynucleotide | *Oryza sativa* | XP466543.1 | Start 184; End 1795 |
| 17 | Polynucleotide | *Arabidopsis thaliana* | BAB01075.1 | Start 1; End 1597 |
| 18 | Polynucleotide | *Arabidopsis thaliana* | AAL15211.1/ AAK59536.1 | Start 1; End 1297 |
| 19 | Polynucleotide | Vector |  | N/A |
| 20 | Polypeptide | Consensus, all plants |  | N/A |
| 21 | Polypeptide | Consensus, dicotyledonous plants |  | N/A |

What is claimed is:

1. A method for producing a plant with increased biomass, the method comprising transformation of a plant cell or plant with:
   a) a polynucleotide comprising a nucleic acid sequence encoding a polypeptide with at least 95% identity to the amino acid sequence of SEQ ID NO: 1; or
   b) a polynucleotide comprising a fragment, of at least 20 nucleotides in length, of the nucleic acid sequence polynucleotide of a); or
   c) a polynucleotide comprising a complement, of at least 20 nucleotides in length, of the nucleic acid sequence of a);
   wherein the expression of the polynucleotide in the plant cell or plant results in the down-regulation of an endogenous polypeptide comprising the amino acid sequence of SEQ ID NO: 20.

2. The method of claim 1, wherein the polynucleotide in a) comprises a nucleic acid sequence encoding the amino acid sequence of SEQ ID NO: 1.

3. The method of claim 1, wherein the plant cell or plant is transformed with a polynucleotide comprising a nucleic acid sequence encoding a polypeptide with the amino acid sequence of SEQ ID NO: 1.

4. The method of claim 1, wherein the polynucleotide in a) comprises the sequence of SEQ ID NO: 10.

5. The method of claim 1, wherein the endogenous polypeptide comprises the sequence of SEQ ID NO: 1.

6. A plant produced by the method of claim 1 wherein the expression of an endogenous polypeptide comprising the amino acid sequence of SEQ ID NO: 20 is down-regulated in said plant relative to a non-transformed control plant and wherein said plant has increased biomass relative to a non-transformed control plant.

7. A plant produced by the method of claim 1, wherein said plant has an increased number of tillers relative to a non-transformed control plant.

8. An isolated polynucleotide comprising a nucleic acid that encodes a polypeptide with at least 95% identity to the amino acid sequence of SEQ ID NO: 1, wherein said polypeptide has the same activity as a polypeptide with the amino acid sequence of SEQ ID NO: 1.

9. The isolated polynucleotide of claim 8, wherein the polynucleotide comprises the nucleotide sequence of SEQ ID NO: 10.

10. A plant genetically modified to express:
    a) a polynucleotide comprising a fragment, of at least 20 nucleotides in length, of the polynucleotide of claim 8; or
    b) a polynucleotide comprising a complement, of at least 20 nucleotides in length, of the polynucleotide of claim 8;
    wherein the expression of the polynucleotide in the plant results in the down-regulation of an endogenous polypeptide comprising the amino acid sequence of SEQ ID NO: 20; and increased biomass production relative to a non-transformed control plant.

11. A plant comprising a genetic construct, which comprises:
    a) a polynucleotide comprising a fragment, of at least 20 nucleotides in length, of the polynucleotide of claim 8; or
    b) a polynucleotide comprising a complement, of at least 20 nucleotides in length, of the polynucleotide of claim 8;
    wherein the construct results in the down-regulation of an endogenous polypeptide comprising the amino acid sequence of SEQ ID NO: 20; and increased biomass relative to a non-transformed control plant.

12. A plant comprising the isolated polynucleotide of claim 8.

13. A plant genetically modified to express the polynucleotide of claim 8.

14. The plant of claim 10, wherein said plant has an increased number of tillers relative to a non-transformed control plant.

15. The plant of claim 1, wherein said plant has an increased number of tillers relative to a non-transformed control plant.

* * * * *

UNITED STATES PATENT AND TRADEMARK OFFICE
CERTIFICATE OF CORRECTION

PATENT NO. : 8,227,665 B2
APPLICATION NO. : 12/324664
DATED : July 24, 2012
INVENTOR(S) : Puthigae et al.

It is certified that error appears in the above-identified patent and that said Letters Patent is hereby corrected as shown below:

In column 2 at line 18, Change "plant" to --plant.--.

In column 2 at line 53, Change "NO:1) to --NO:1.--.

In column 3 at line 2, Change "plant" to --plant.--.

In column 3 at line 33, Change "plant" to --plant.--.

In column 3 at line 53, Change "NO:1) to --NO:1.--.

In column 3 at line 66, Change "the a" to --the--.

In column 4 at line 28, Change "plant" to --plant.--.

In column 4 at line 31, Change "NO:1) to --NO:1.--.

In column 6 at line 16, Change "Cossypium," to --Gossypium,--.

In column 6 at line 17, Change "Helianithis," to --Helianthus,--.

In column 6 at line 17, Change "Lens.," to --Lens,--.

In column 6 at line 17-18, Change "Lupinis, Macadaia," to --Lupinus, Macadamia,--.

In column 6 at line 19, Change "Phaseolis," to --Phaseolus,--.

In column 6 at line 20, Change "Ricinis," to --Ricinus,--.

In column 6 at line 24, Change "Brassica.nigra." to --Brassica nigra,--.

In column 6 at line 25, Change "indicus." to --indicus,--.

In column 6 at line 28, Change "Coronilli" to --Coronilla--.

In column 6 at line 28, Change "Cossypium," to --Gossypium,--.

In column 6 at line 32, Change "annus," to --annuus,--.

In column 6 at line 17-18, Change "Lipinis" to --Lupinus--.

In column 6 at line 38, Change "Medicago." to --Medicago--.

In column 6 at line 39, Change "integrifolia." to --integrifolia,--.

In column 6 at line 43, Change "Prunus.maheleb," to --Prunus mahaleb,--.

Signed and Sealed this
Twenty-sixth Day of March, 2013

Teresa Stanek Rea
*Acting Director of the United States Patent and Trademark Office*

CERTIFICATE OF CORRECTION (continued)
U.S. Pat. No. 8,227,665 B2

In column 6 at line 44, After "mungo," change "Prunus." to --Prunus--.

In column 6 at line 44, After "persica," change "Prunus." to --Prunus--.

In column 6 at line 44-45, Change "Phaseolis vulgaris." to --Phaseolus vulgaris,--.

In column 6 at line 45, Change "somniferum." to --somniferum,--.

In column 6 at line 48-49, Change "communic," to --communis,--.

In column 6 at line 49, Change "augustifolium." to --angustifolium,--.

In column 6 at line 50, Change "hybridum." to --hybridum,--.

In column 6 at line 54, Change "Vivia" to --Vicia--.

In column 6 at line 55, Change "ervillia," to --ervilia,--.

In column 6 at line 57, Change "sative" to --sativa--.

In column 6 at line 59, Change "Alopecuris," to --Alopecurus,--.

In column 6 at line 60, Change "Bothrichloa," to --Bothriochloa,--.

In column 6 at line 64, Change "Miscanthus×giganteus," to --Miscanthus x giganteus,--

In column 6 at line 66, Change "Sorgahastum," to --Sorghastrum,--.

In column 7 at line 6, After "schoenoprasum," change "Allium." to --Allium--.

In column 7 at line 6, After "fistulosum," change "Allium." to --Allium--.

In column 7 at line 8, Change "scoparious," to --scoparius,--.

In column 7 at line 10, After "vulgaris," change "Bothrichloa," to --Bothriochloa,--.

In column 7 at line 10, After "barbinodis," change "Bothrichloa" to --Bothriochloa--.

In column 7 at line 11, Change "Bothrichloa," to --Bothriochloa,--.

In column 7 at line 11-12, Change "curipendula," to --curtipendula,--.

In column 7 at line 13, Change "longifilia," to --longifolia,--.

In column 7 at line 14, Change "Cenchriis" to --Cenchrus--.

In column 7 at line 17, Change "coracan," to --coracana,--.

In column 7 at line 21, Change "annus" to --annuus--.

In column 7 at line 21, Change "sunflower," to --(sunflower),--.

In column 7 at line 22-23, Change "perenn, Miscanthis" to --perenne, Miscanthus--.

In column 7 at line 23, Change "Miscanthus×giganteus," to --Miscanthus x giganteus,--.

In column 7 at line 24, Change "italicium," to --italicum,--.

In column 7 at line 28-29, Change "bertolinii," to --bertolini,--.

In column 7 at line 29, Change "Poa." to --Poa--.

In column 10 at line 44, Change "$1\times 10^{-50}$" to --$1\times 10^{-50}$,--.

In column 10 at line 45, Change "$1\times 10^{-60}$" to --$1\times 10^{-60}$,--.

In column 10 at line 46, Change "$1\times 10^{-80}$" to --$1\times 10^{-80}$,--.

CERTIFICATE OF CORRECTION (continued)
U.S. Pat. No. 8,227,665 B2

In column 12 at line 54, Change "$1\times10^{-50}$" to --$1\times10^{-50}$,--.

In column 17 at line 64, Change "Purification,)." to --Purification).--.

In column 18 at line 66, Change "Manual." to --Manual,--.

In column 19 at line 2, Change "Manual." to --Manual,--.

In column 19 at line 59, Change "phophotransferase" to --phosphotransferase--.

In column 20 at line 61, Change "al," to --al.,--.

In column 21 at line 30, Change "311.);" to --311);--.

In column 22 at line 18-19, Change "Harbour" to --Harbor--.

In column 23 at line 2, Change "thereof" to --thereof.--.

In column 23 at line 17, Change "FIG." to --FIGS.--.

In column 25 at line 56, Change "mersitematic" to --meristematic--.

In column 26 at line 63, Change "12262" to --12262.--.

In column 26 at line 64, Change "529" to --529.--.

In column 26 at line 65, Change "497" to --497.--.

In column 27 at line 2, Change "116" to --116.--.

In column 27 at line 7, Change "1.1-1.4" to --1.1-1.4.--.

In column 28 at line 3, Change "487" to --487.--.

In column 79 at line 19-20, In Claim 1, after "sequence" delete "polynucleotide".

In column 79 at line 30, In Claim 2, after "encoding" insert --a polypeptide with--.

In column 79 at line 49, In Claim 8, after "acid" insert --sequence--.

In column 80 at line 47, In Claim 15, change "1," to --11,--.

SEQUENCE LISTING

```
<160> NUMBER OF SEQ ID NOS: 21

<210> SEQ ID NO 1
<211> LENGTH: 534
<212> TYPE: PRT
<213> ORGANISM: Lolium perenne

<400> SEQUENCE: 1

Met Asp Ala Thr Thr Ser Ser Gly Ala Ser Ser Ser Leu Pro Leu His
1               5                  10                  15

Leu Ile Val Asp Asp Thr Leu Ser Leu Val Ser Pro Leu Gln Gln Ser
            20                  25                  30

Tyr Gln Arg Ser Gln Arg His Cys Leu Gly Asp Ser Ala Pro Gly Glu
        35                  40                  45

Phe Pro Leu Ala Ala Asn Pro Ser Ile Val Leu His Val Leu Thr Ser
    50                  55                  60

Cys Asn Leu Glu Pro Glu Asp Leu Ala His Leu Glu Ala Thr Cys Lys
65                  70                  75                  80

Phe Phe Arg Lys Pro Ala Asn Phe Pro Pro Asp Phe Leu Leu Ser Met
                85                  90                  95

Ser Glu Leu Ala Ala Phe Asp Met Cys Gln Asn Arg Ala Ile Phe Lys
            100                 105                 110

Pro Met Gly Thr Gln Glu Lys Glu Met Phe Lys Gln Arg Cys Gly Gly
        115                 120                 125
```

```
Thr Trp Lys Leu Val Leu Arg Phe Ile Thr Leu Gly Glu Ala Cys Cys
130                 135                 140

Arg Arg Glu Lys Ser Gln Ala Ile Ala Gly Pro Gly His Ser Val Ala
145                 150                 155                 160

Val Thr Ala Ser Gly Ala Ala Tyr Ser Phe Gly Ser Asn Asn Ser Gly
                165                 170                 175

Gln Leu Gly His Asp Arg Leu Glu Glu Glu Trp Arg Pro Arg Pro Ile
                180                 185                 190

Arg Ser Leu Gln Gly Ile Arg Ile Ile Gln Ala Ala Gly Ala Gly
            195                 200                 205

Arg Thr Met Leu Val Ser Asp Ala Gly Arg Val Tyr Ala Phe Gly Lys
        210                 215                 220

Asp Ser Phe Gly Glu Val Glu Tyr Gly Asn Gln Gly Ser Arg Val Val
225                 230                 235                 240

Thr Thr Pro Gln Leu Val Glu Ser Leu Lys Asp Ile Tyr Ile Val Gln
                245                 250                 255

Ala Ala Ile Gly Asn Phe Phe Thr Ala Val Leu Ser Arg Glu Gly Cys
                260                 265                 270

Val Tyr Thr Phe Ser Trp Gly Gly Asp Met Lys Leu Gly His Gln Thr
            275                 280                 285

Glu Pro Asn Asp Val Gln Pro His Leu Leu Ala Gly Pro Leu Glu Asp
        290                 295                 300

Ile Pro Val Val Gln Ile Ala Ala Gly Tyr Cys Tyr Leu Leu Leu Leu
305                 310                 315                 320

Ala Cys Gln Pro Ser Gly Met Ser Val Tyr Ser Val Gly Cys Gly Leu
                325                 330                 335

Gly Gly Lys Leu Gly His Gly Ser Arg Ser Asp Glu Lys Tyr Pro Arg
                340                 345                 350

Leu Ile Glu Gln Phe Gln Thr Leu Asn Ile Gln Pro Val Val Val Ala
            355                 360                 365

Ala Gly Ala Trp His Ala Ala Val Gly Lys Asp Gly Arg Val Cys
        370                 375                 380

Thr Trp Gly Trp Gly Arg Tyr Gly Cys Leu Gly His Gly Asn Glu Glu
385                 390                 395                 400

Cys Glu Ser Val Pro Lys Val Val Glu Thr Leu Ser Ser Val Lys Ala
                405                 410                 415

Val His Val Ala Thr Gly Asp Tyr Thr Thr Phe Val Val Ser His Lys
                420                 425                 430

Gly Asp Val Tyr Ser Phe Gly Cys Gly Glu Ser Ser Leu Gly His
                435                 440                 445

Asn Thr Ala Ile Glu Gly Asn Asn Arg His Ser Asn Val Leu Ser Pro
        450                 455                 460

Glu Leu Val Thr Ser Ser Gln Arg Thr Asp Glu Arg Val Val His Val
465                 470                 475                 480

Ser Leu Thr Asn Ser Ile Tyr Trp Asn Ala His Thr Phe Ala Leu Thr
                485                 490                 495

Glu Ser Ala Lys Leu Tyr Ala Phe Gly Ala Gly Asp Lys Gly Gln Leu
                500                 505                 510

Gly Thr Glu Leu Val Glu His Arg Ser Glu Arg Gly Thr Pro Glu Gln
            515                 520                 525

Val Asp Ile Asp Leu Asn
        530
```

<210> SEQ ID NO 2
<211> LENGTH: 534
<212> TYPE: PRT
<213> ORGANISM: Oryza sativa

<400> SEQUENCE: 2

```
Met Asp Ala Thr Thr Ser Ser Gly Ala Ser Ser Leu Pro Leu His
1               5                   10                  15

Leu Ile Ile Asp Asp Ala Leu Ala Leu Val Ser Pro Leu Gln Gln Ser
            20                  25                  30

Phe Gln Arg Ser Gln Arg His Cys Phe Gly Gly Ser Ala Pro Gly Glu
            35                  40                  45

Phe Pro Leu Ala Ala Asn Pro Ser Ile Val Leu His Val Leu Thr Ser
50                  55                  60

Cys Asn Leu Glu Pro Asp Asp Leu Ala His Leu Glu Ala Thr Cys Ser
65                  70                  75                  80

Phe Phe Arg Lys Pro Ala Asn Phe Pro Pro Asp Phe Gln Leu Ser Met
                85                  90                  95

Ser Glu Leu Ala Ala Leu Asp Met Cys Gln Lys Arg Ala Ile Phe Lys
            100                 105                 110

Pro Met Thr Gln Gln Glu Arg Glu Met Phe Lys Gln Arg Cys Gly Gly
            115                 120                 125

Ser Trp Lys Leu Val Leu Arg Phe Ile Met Ala Gly Glu Ala Cys Cys
130                 135                 140

Arg Arg Glu Lys Ser Gln Ala Ile Ala Gly Pro Gly His Ser Ile Ala
145                 150                 155                 160

Val Thr Thr Ser Gly Ala Val Tyr Thr Phe Gly Ser Asn Ser Ser Gly
                165                 170                 175

Gln Leu Gly His Gly Ser Leu Glu Glu Glu Trp Arg Pro Arg Ile Ile
            180                 185                 190

Arg Ser Leu Gln Gly Ile Arg Ile Ile Gln Ala Ala Gly Ala Gly
            195                 200                 205

Arg Thr Met Leu Val Ser Asp Ala Gly Arg Val Tyr Ala Phe Gly Lys
210                 215                 220

Asp Ser Phe Gly Glu Val Glu Tyr Ala Ala Gln Gly Ser Arg Val Val
225                 230                 235                 240

Thr Thr Pro Gln Leu Val Glu Ser Leu Lys Asp Ile Tyr Ile Val Gln
                245                 250                 255

Ala Ala Ile Gly Asn Phe Phe Thr Ala Val Leu Ser Arg Glu Gly His
            260                 265                 270

Val Tyr Thr Phe Ser Trp Gly Asn Asp Met Lys Leu Gly His Gln Thr
            275                 280                 285

Glu Pro Asn Asp Val Gln Pro His Leu Leu Ala Gly Pro Leu Glu Asn
290                 295                 300

Ile Pro Val Val Gln Ile Ala Ala Gly Tyr Cys Tyr Leu Leu Ala Leu
305                 310                 315                 320

Ala Cys Gln Pro Ser Gly Met Ser Val Tyr Ser Val Gly Cys Gly Leu
                325                 330                 335

Gly Gly Lys Leu Gly His Gly Ser Arg Thr Asp Glu Lys Tyr Pro Arg
            340                 345                 350

Leu Ile Glu Gln Phe Gln Ala Leu Asn Ile Gln Pro Val Val Val Ala
            355                 360                 365

Ala Gly Ala Trp His Ala Ala Val Val Gly Lys Asp Gly Arg Val Cys
370                 375                 380
```

-continued

```
Thr Trp Gly Trp Gly Arg Tyr Gly Cys Leu Gly His Gly Asn Glu Glu
385                 390                 395                 400

Cys Glu Ser Val Pro Lys Val Val Glu Ser Leu Val Asn Val Arg Ala
                405                 410                 415

Val His Val Ala Thr Gly Asp Tyr Thr Thr Phe Val Val Ser Asp Lys
            420                 425                 430

Gly Asp Val Tyr Ser Phe Gly Cys Gly Glu Ser Ser Leu Gly His
        435                 440                 445

Asn Thr Ile Thr Glu Gly Asn Asn Arg His Thr Asn Val Leu Ser Pro
    450                 455                 460

Glu Leu Val Thr Ser Leu Lys Arg Thr Asn Glu Arg Val Ala Gln Ile
465                 470                 475                 480

Ser Leu Thr Asn Ser Ile Tyr Trp Asn Ala His Thr Phe Ala Leu Thr
                485                 490                 495

Asp Ser Gly Lys Leu Tyr Ala Phe Gly Ala Gly Asp Lys Gly Gln Leu
            500                 505                 510

Gly Thr Glu Leu Val Ala Gln Glu Ser Glu Arg Gly Thr Pro Glu Arg
        515                 520                 525

Val Glu Ile Asp Leu Ser
    530

<210> SEQ ID NO 3
<211> LENGTH: 534
<212> TYPE: PRT
<213> ORGANISM: Oryza sativa

<400> SEQUENCE: 3

Met Asp Ala Thr Thr Ser Ser Gly Ala Ser Ser Leu Pro Leu His
1               5                   10                  15

Leu Ile Ile Asp Asp Ala Leu Ala Leu Val Ser Pro Leu Gln Gln Ser
                20                  25                  30

Phe Gln Arg Ser Gln Arg His Cys Phe Gly Gly Ser Ala Pro Gly Glu
            35                  40                  45

Phe Pro Leu Ala Ala Asn Pro Ser Ile Val Leu His Val Leu Thr Ser
        50                  55                  60

Cys Asn Leu Glu Pro Asp Asp Leu Ala His Leu Glu Ala Thr Cys Ser
65                  70                  75                  80

Phe Phe Arg Lys Pro Ala Asn Phe Pro Pro Asp Phe Gln Leu Ser Met
                85                  90                  95

Ser Glu Leu Ala Ala Leu Asp Met Cys Gln Lys Arg Ala Ile Phe Lys
            100                 105                 110

Pro Met Thr Gln Gln Glu Arg Glu Met Phe Lys Gln Arg Cys Gly Gly
        115                 120                 125

Ser Trp Lys Leu Val Leu Arg Phe Ile Met Ala Gly Glu Ala Cys Cys
130                 135                 140

Arg Arg Glu Lys Ser Gln Ala Ile Ala Gly Pro Gly His Ser Ile Ala
145                 150                 155                 160

Val Thr Thr Ser Gly Ala Val Tyr Thr Phe Gly Ser Asn Ser Ser Gly
                165                 170                 175

Gln Leu Gly His Gly Ser Leu Glu Glu Glu Trp Arg Pro Arg Ile Ile
            180                 185                 190

Arg Ser Leu Gln Gly Ile Arg Ile Gln Ala Ala Gly Ala Gly
        195                 200                 205

Arg Thr Met Leu Val Ser Asp Ala Gly Arg Val Tyr Ala Phe Gly Lys
210                 215                 220
```

-continued

Asp Ser Phe Gly Glu Val Glu Tyr Ala Ala Gln Gly Ser Arg Val Val
225                 230                 235                 240

Thr Thr Pro Gln Leu Val Glu Ser Leu Lys Asp Ile Tyr Ile Val Gln
            245                 250                 255

Ala Ala Ile Gly Asn Phe Phe Thr Ala Val Leu Ser Arg Glu Gly His
            260                 265                 270

Val Tyr Thr Phe Ser Trp Gly Asn Asp Met Lys Leu Gly His Gln Thr
        275                 280                 285

Glu Pro Asn Asp Val Gln Pro His Leu Leu Ala Gly Pro Leu Glu Asn
290                 295                 300

Ile Pro Val Val Gln Ile Ala Ala Gly Tyr Cys Tyr Leu Leu Ala Leu
305                 310                 315                 320

Ala Cys Gln Pro Ser Gly Met Ser Val Tyr Ser Val Gly Cys Gly Leu
            325                 330                 335

Gly Gly Lys Leu Gly His Gly Ser Arg Thr Asp Glu Lys Tyr Pro Arg
            340                 345                 350

Leu Ile Glu Gln Phe Gln Ala Leu Asn Ile Gln Pro Val Val Ala
        355                 360                 365

Ala Gly Ala Trp His Ala Ala Val Val Gly Lys Asp Gly Arg Val Cys
    370                 375                 380

Thr Trp Gly Trp Gly Arg Tyr Gly Cys Leu Gly His Gly Asn Glu Glu
385                 390                 395                 400

Cys Glu Ser Val Pro Lys Val Val Glu Ser Leu Val Asn Val Arg Ala
            405                 410                 415

Val His Val Ala Thr Gly Asp Tyr Thr Thr Phe Val Val Ser Asp Lys
        420                 425                 430

Gly Asp Val Tyr Ser Phe Gly Cys Gly Glu Ser Ser Ser Leu Gly His
        435                 440                 445

Asn Thr Ile Thr Glu Gly Asn Asn Arg His Thr Asn Val Leu Ser Pro
450                 455                 460

Glu Leu Val Thr Ser Leu Lys Arg Thr Asn Glu Arg Val Ala Gln Ile
465                 470                 475                 480

Ser Leu Thr Asn Ser Ile Tyr Trp Asn Ala His Thr Phe Ala Leu Thr
            485                 490                 495

Asp Ser Gly Lys Leu Tyr Ala Phe Gly Ala Gly Asp Lys Gly Gln Leu
        500                 505                 510

Gly Thr Glu Leu Val Ala Gln Glu Ser Glu Arg Gly Thr Pro Glu Arg
        515                 520                 525

Val Glu Ile Asp Leu Ser
        530

<210> SEQ ID NO 4
<211> LENGTH: 534
<212> TYPE: PRT
<213> ORGANISM: Oryza sativa

<400> SEQUENCE: 4

Met Asp Ala Thr Thr Ser Ser Gly Ala Ser Ser Leu Pro Leu His
1               5                   10                  15

Leu Ile Ile Asp Asp Ala Leu Ala Leu Val Ser Pro Leu Gln Gln Ser
            20                  25                  30

Phe Gln Arg Ser Gln Arg His Cys Phe Gly Gly Ser Ala Pro Gly Glu
        35                  40                  45

Phe Pro Leu Ala Ala Asn Pro Ser Ile Val Leu His Val Leu Thr Ser
    50                  55                  60

-continued

Cys Asn Leu Glu Pro Asp Asp Leu Ala His Leu Glu Ala Thr Cys Ser
65                  70                  75                  80

Phe Phe Arg Lys Pro Ala Asn Phe Pro Pro Asp Phe Gln Leu Ser Met
                85                  90                  95

Ser Glu Leu Ala Ala Leu Asp Met Cys Gln Lys Arg Ala Ile Phe Lys
            100                 105                 110

Pro Met Thr Gln Gln Glu Arg Glu Met Phe Lys Gln Arg Cys Gly Gly
        115                 120                 125

Ser Trp Lys Leu Val Leu Arg Phe Ile Met Ala Gly Glu Ala Cys Cys
    130                 135                 140

Arg Arg Glu Lys Ser Gln Ala Ile Ala Gly Pro Gly His Ser Ile Ala
145                 150                 155                 160

Val Thr Thr Ser Gly Ala Val Tyr Thr Phe Gly Ser Asn Ser Ser Gly
                165                 170                 175

Gln Leu Gly His Gly Ser Leu Glu Glu Glu Trp Arg Pro Arg Ile Ile
            180                 185                 190

Arg Ser Leu Gln Gly Ile Arg Ile Ile Gln Ala Ala Gly Ala Gly
        195                 200                 205

Arg Thr Met Leu Val Ser Asp Ala Gly Arg Val Tyr Ala Phe Gly Lys
210                 215                 220

Asp Ser Phe Gly Glu Val Glu Tyr Ala Ala Gln Gly Ser Arg Val Val
225                 230                 235                 240

Thr Thr Pro Gln Leu Val Glu Ser Leu Lys Asp Ile Tyr Ile Val Gln
                245                 250                 255

Ala Ala Ile Gly Asn Phe Phe Thr Ala Val Leu Ser Arg Glu Gly His
            260                 265                 270

Val Tyr Thr Phe Ser Trp Gly Asn Asp Met Lys Leu Gly His Gln Thr
        275                 280                 285

Glu Pro Asn Asp Val Gln Pro His Leu Leu Ala Gly Pro Leu Glu Asn
    290                 295                 300

Ile Pro Val Val Gln Ile Ala Ala Gly Tyr Cys Tyr Leu Leu Ala Leu
305                 310                 315                 320

Ala Cys Gln Pro Ser Gly Met Ser Val Tyr Ser Val Gly Cys Gly Leu
                325                 330                 335

Gly Gly Lys Leu Gly His Gly Ser Arg Thr Asp Glu Lys Tyr Pro Arg
            340                 345                 350

Leu Ile Glu Gln Phe Gln Ala Leu Asn Ile Gln Pro Val Val Val Ala
        355                 360                 365

Ala Gly Ala Trp His Ala Ala Val Val Gly Lys Asp Gly Arg Val Cys
    370                 375                 380

Thr Trp Gly Trp Gly Arg Tyr Gly Cys Leu Gly His Gly Asn Glu Glu
385                 390                 395                 400

Cys Glu Ser Val Pro Lys Val Val Glu Ser Leu Val Asn Val Arg Ala
                405                 410                 415

Val His Val Ala Thr Gly Asp Tyr Thr Thr Phe Val Val Ser Asp Lys
            420                 425                 430

Gly Asp Val Tyr Ser Phe Gly Cys Gly Glu Ser Ser Leu Gly His
        435                 440                 445

Asn Thr Ile Thr Glu Gly Asn Asn Arg His Thr Asn Val Leu Ser Pro
    450                 455                 460

Glu Leu Val Thr Ser Leu Lys Arg Thr Asn Glu Arg Val Ala Gln Ile
465                 470                 475                 480

Ser Leu Thr Asn Ser Ile Tyr Trp Asn Ala His Thr Phe Ala Leu Thr
                485                 490                 495

```
Asp Ser Gly Lys Leu Tyr Ala Phe Gly Ala Asp Lys Gly Gln Leu
            500                 505                 510

Gly Thr Glu Leu Val Ala Gln Glu Ser Glu Arg Gly Thr Pro Glu Arg
            515                 520                 525

Val Glu Ile Asp Leu Ser
            530

<210> SEQ ID NO 5
<211> LENGTH: 534
<212> TYPE: PRT
<213> ORGANISM: Oryza sativa

<400> SEQUENCE: 5

Met Asp Ala Thr Thr Ser Ser Gly Ala Ser Ser Leu Pro Leu His
1               5                   10                  15

Leu Ile Ile Asp Asp Ala Leu Ala Leu Val Ser Pro Leu Gln Gln Ser
                20                  25                  30

Phe Gln Arg Ser Gln Arg His Cys Phe Gly Gly Ser Ala Pro Gly Glu
            35                  40                  45

Phe Pro Leu Ala Ala Asn Pro Ser Ile Val Leu His Val Leu Thr Ser
        50                  55                  60

Cys Asn Leu Glu Pro Asp Asp Leu Ala His Leu Glu Ala Thr Cys Ser
65                  70                  75                  80

Phe Phe Arg Lys Pro Ala Asn Phe Pro Pro Asp Phe Gln Leu Ser Met
                85                  90                  95

Ser Glu Leu Ala Ala Leu Asp Met Cys Gln Lys Arg Ala Ile Phe Lys
            100                 105                 110

Pro Met Thr Gln Gln Glu Arg Glu Met Phe Lys Gln Arg Cys Gly Gly
        115                 120                 125

Ser Trp Lys Leu Val Leu Arg Phe Ile Met Ala Gly Glu Ala Cys Cys
    130                 135                 140

Arg Arg Glu Lys Ser Gln Ala Ile Ala Gly Pro Gly His Ser Ile Ala
145                 150                 155                 160

Val Thr Thr Ser Gly Ala Val Tyr Thr Phe Gly Ser Asn Ser Ser Gly
                165                 170                 175

Gln Leu Gly His Gly Ser Leu Glu Glu Glu Trp Arg Pro Arg Ile Ile
            180                 185                 190

Arg Ser Leu Gln Gly Ile Arg Ile Gln Ala Ala Gly Ala Gly
        195                 200                 205

Arg Thr Met Leu Val Ser Asp Ala Gly Arg Val Tyr Ala Phe Gly Lys
    210                 215                 220

Asp Ser Phe Gly Glu Val Glu Tyr Ala Ala Gln Gly Ser Arg Val Val
225                 230                 235                 240

Thr Thr Pro Gln Leu Val Glu Ser Leu Lys Asp Ile Tyr Ile Val Gln
                245                 250                 255

Ala Ala Ile Gly Asn Phe Phe Thr Ala Val Leu Ser Arg Glu Gly His
            260                 265                 270

Val Tyr Thr Phe Ser Trp Gly Asn Asp Met Lys Leu Gly His Gln Thr
        275                 280                 285

Glu Pro Asn Asp Val Gln Pro His Leu Leu Ala Gly Pro Leu Glu Asn
    290                 295                 300

Ile Pro Val Val Gln Ile Ala Ala Gly Tyr Cys Tyr Leu Leu Ala Leu
305                 310                 315                 320

Ala Cys Gln Pro Ser Gly Val Ser Val Tyr Ser Val Gly Cys Gly Leu
                325                 330                 335
```

-continued

```
Gly Gly Lys Leu Gly His Gly Ser Arg Thr Asp Lys Tyr Pro Arg
            340                 345                 350

Leu Ile Glu Gln Phe Gln Ala Leu Asn Ile Gln Pro Val Val Ala
            355                 360                 365

Ala Gly Ala Trp His Ala Val Val Gly Lys Asp Gly Arg Val Cys
            370                 375                 380

Thr Trp Gly Trp Gly Arg Tyr Gly Cys Leu Gly His Gly Asn Glu Glu
385                 390                 395                 400

Cys Glu Ser Val Pro Lys Val Val Glu Ser Leu Val Asn Val Arg Ala
                    405                 410                 415

Val His Val Ala Thr Gly Asp Tyr Thr Thr Phe Val Val Ser Asp Lys
                    420                 425                 430

Gly Asp Val Tyr Ser Phe Gly Cys Gly Glu Ser Ser Ser Leu Gly His
            435                 440                 445

Asn Thr Ile Thr Glu Gly Asn Asn Arg His Thr Asn Val Leu Ser Pro
            450                 455                 460

Glu Leu Val Thr Ser Leu Lys Arg Thr Asn Glu Arg Val Ala Gln Ile
465                 470                 475                 480

Ser Leu Thr Asn Ser Ile Tyr Trp Asn Ala His Thr Phe Ala Leu Thr
                    485                 490                 495

Asp Ser Gly Lys Leu Tyr Ala Phe Gly Ala Gly Asp Lys Gly Gln Leu
                    500                 505                 510

Gly Thr Glu Leu Val Ala Gln Glu Ser Glu Arg Gly Thr Pro Glu Arg
            515                 520                 525

Val Glu Ile Asp Leu Ser
            530

<210> SEQ ID NO 6
<211> LENGTH: 334
<212> TYPE: PRT
<213> ORGANISM: Oryza sativa

<400> SEQUENCE: 6

Ile Gln Ala Ala Ala Gly Ala Gly Arg Thr Met Leu Val Ser Asp Ala
1               5                   10                  15

Gly Arg Val Tyr Ala Phe Gly Lys Asp Ser Phe Gly Glu Val Glu Tyr
            20                  25                  30

Ala Ala Gln Gly Ser Arg Val Val Thr Thr Pro Gln Leu Val Glu Ser
        35                  40                  45

Leu Lys Asp Ile Tyr Ile Val Gln Ala Ala Ile Gly Asn Phe Phe Thr
    50                  55                  60

Ala Val Leu Ser Arg Glu Gly His Val Tyr Thr Phe Ser Trp Gly Asn
65                  70                  75                  80

Asp Met Lys Leu Gly His Gln Thr Glu Pro Asn Asp Val Gln Pro His
                85                  90                  95

Leu Leu Ala Gly Pro Leu Glu Asn Ile Pro Val Val Gln Ile Ala Ala
            100                 105                 110

Gly Tyr Cys Tyr Leu Leu Ala Leu Ala Cys Gln Pro Ser Gly Met Ser
        115                 120                 125

Val Tyr Ser Val Gly Cys Gly Leu Gly Gly Lys Leu Gly His Gly Ser
    130                 135                 140

Arg Thr Asp Glu Lys Tyr Pro Arg Leu Ile Glu Gln Phe Gln Ala Leu
145                 150                 155                 160

Asn Ile Gln Pro Val Val Val Ala Ala Gly Ala Trp His Ala Ala Val
                165                 170                 175
```

```
Val Gly Lys Asp Gly Arg Val Cys Thr Trp Gly Trp Gly Arg Tyr Gly
        180                 185                 190

Cys Leu Gly His Gly Asn Glu Cys Glu Ser Val Pro Lys Val Val
        195                 200                 205

Glu Ser Leu Val Asn Val Arg Ala Val His Val Ala Thr Gly Asp Tyr
        210                 215                 220

Thr Thr Phe Val Val Ser Asp Lys Gly Asp Val Tyr Ser Phe Gly Cys
225                 230                 235                 240

Gly Glu Ser Ser Ser Leu Gly His Asn Thr Ile Thr Glu Gly Asn Asn
                245                 250                 255

Arg His Thr Asn Val Leu Ser Pro Glu Leu Val Thr Ser Leu Lys Arg
        260                 265                 270

Thr Asn Glu Arg Val Ala Gln Ile Ser Leu Thr Asn Ser Ile Tyr Trp
        275                 280                 285

Asn Ala His Thr Phe Ala Leu Thr Asp Ser Gly Lys Leu Tyr Ala Phe
        290                 295                 300

Gly Ala Gly Asp Lys Gly Gln Leu Gly Thr Glu Leu Val Ala Gln Glu
305                 310                 315                 320

Ser Glu Arg Gly Thr Pro Glu Arg Val Glu Ile Asp Leu Ser
                325                 330

<210> SEQ ID NO 7
<211> LENGTH: 537
<212> TYPE: PRT
<213> ORGANISM: Oryza sativa

<400> SEQUENCE: 7

Met Gln Cys Pro Met Asp Ala Ala Ser Gly Thr Ser Pro Val Met
1               5                   10                  15

Gln Phe His Gly Ile Val Asp Glu Pro Pro Ser His Ser Ser Pro Leu
                20                  25                  30

His Thr Ala Leu Glu Arg Ser Gln Arg His Cys Tyr Gly His Glu Thr
        35                  40                  45

Pro Gly Glu Phe Pro Leu Ala Val Ser Pro Ser Ile Val Leu His Val
50                  55                  60

Leu Ser Thr Cys Glu Leu Asp Pro Lys Asp Leu Ala Ala Leu Glu Ala
65                  70                  75                  80

Thr Cys Thr Phe Phe Ser Lys Pro Ala Asn Phe Glu Pro Asn Phe Ala
                85                  90                  95

Leu Ser Leu Pro Glu Val Ala Ala Phe Asp Met Cys His Lys Arg Pro
                100                 105                 110

Met Val Lys Leu Met Ala Gln Gln Glu Arg Glu Gln Leu Lys Gln Arg
        115                 120                 125

Cys Gly Gly Ser Trp Lys Leu Val Phe Lys Tyr Ile Val Ala Arg Glu
        130                 135                 140

Arg Asn Tyr Ser Arg Ile Val Ala Gly Pro His Ser Ile Val Val
145                 150                 155                 160

Thr Thr Lys Gly Asp Ala Tyr Ser Phe Gly Ala Asn Cys Trp Gly Gln
                165                 170                 175

Leu Gly Leu Gly Asp Thr Glu Arg Phe Lys Pro Cys Leu Ile Arg
        180                 185                 190

Ser Leu Gln Ser Ile Lys Ile Thr Gln Ala Ala Val Gly Ser Arg Gln
        195                 200                 205

Thr Met Leu Val Ser Asp Thr Gly Ser Val Tyr Ala Phe Gly Lys Gly
        210                 215                 220
```

Ser Phe Val Trp Glu Glu Leu Ser Asp Ala Ala Asp His Ile Thr Thr
225                 230                 235                 240

Pro Lys Ile Val Glu Ser Leu Lys Gly Val Phe Val Gln Ala Ala
            245                 250                 255

Ile Gly Gly Tyr Phe Ser Ala Phe Leu Ser Arg Glu Gly Gln Val Tyr
            260                 265                 270

Thr Ile Ser Trp Gly Arg Thr Glu Arg Leu Gly His Ser Ser Asp Pro
            275                 280                 285

Ser Asp Val Glu Pro Arg Leu Leu Ser Gly Pro Leu Glu Gly Val Leu
290                 295                 300

Val Ala Gln Ile Ser Ala Gly Asn Cys Tyr Leu Leu Met Leu Ala Tyr
305                 310                 315                 320

Gln Pro Thr Gly Met Ser Val Tyr Ser Val Gly Cys Gly Leu Gly Gly
            325                 330                 335

Lys Leu Gly His Gly Cys Lys Asn Asn Lys Gly Thr Pro Lys Leu Ile
            340                 345                 350

Glu His Phe Leu Thr Leu Ser Phe Asn Pro Val Ser Val Ala Ala Gly
            355                 360                 365

Thr Trp His Ala Ala Leu Gly Asp Asp Gly Arg Val Cys Thr Trp
370                 375                 380

Gly Trp Gly His Thr Gly Cys Leu Gly His Gly Asp Glu Glu Tyr Arg
385                 390                 395                 400

Val Leu Pro Thr Val Val Gln Gly Leu Ser Asn Val Lys Ala Val His
            405                 410                 415

Val Ser Thr Gly Glu Tyr Thr Thr Phe Val Val Ser Asp Asn Gly Asp
            420                 425                 430

Thr Tyr Ser Phe Gly Ser Ala Glu Ser Leu Asn Ile Gly Phe Gln Glu
            435                 440                 445

Asp Glu Glu Ala Ala Asp Asp Ala Asp Phe Ser Thr Pro Ser Leu Val
        450                 455                 460

Glu Ser Leu Lys Val Leu Asn Asp Lys Ala Val Gln Ile Ser Thr Thr
465                 470                 475                 480

Asn Ser Ser Tyr Trp Leu Asn Ser Glu Met Gly Tyr Pro His Thr Phe
            485                 490                 495

Ala Leu Met Glu Ser Gly Lys Leu Tyr Ala Phe Gly Gly Ile Lys
        500                 505                 510

Gly Gln Leu Gly Val Lys Leu Ser Glu Gly Gln Glu Arg Ala Gln Asn
            515                 520                 525

Pro Glu Arg Val Pro Ile Asp Leu Cys
        530                 535

<210> SEQ ID NO 8
<211> LENGTH: 532
<212> TYPE: PRT
<213> ORGANISM: Arabidopsis thaliana

<400> SEQUENCE: 8

Met Asp Ala Thr Ser Gly Thr Pro Ser Leu Gln Tyr Ile Asn Leu Pro
1               5                   10                  15

Glu Gln Ser Val Ser Thr Thr Ser Pro Pro Val Ser Phe Gln Arg
            20                  25                  30

Pro Lys Arg His Cys Phe Gly Asp Thr Thr Pro Gly Glu Phe Pro Leu
        35                  40                  45

Ala Ala Asn Pro Ser Ile Val Leu His Val Leu Thr Glu Cys Arg Leu
50                  55                  60

```
Asp Pro Arg Asp Leu Ala Asn Leu Glu Ala Thr Cys Ser Phe Phe Ser
 65                  70                  75                  80

Gln Pro Ala Asn Phe Ala Pro Asp Ile Asn Leu Ser Leu Ser Glu Leu
                 85                  90                  95

Ala Ala Leu Asp Met Cys Asn Lys Arg Val Ile Phe Lys Pro Met Asn
            100                 105                 110

Glu Glu Glu Arg Gln Glu Met Lys Arg Arg Cys Gly Gly Ser Trp Lys
        115                 120                 125

Leu Val Leu Arg Phe Leu Leu Ala Gly Glu Ala Cys Cys Arg Arg Glu
    130                 135                 140

Lys Ser Gln Ala Val Ala Gly Pro Gly His Ser Val Ala Val Thr Ser
145                 150                 155                 160

Lys Gly Glu Val Tyr Thr Phe Gly Tyr Asn Asn Ser Gly Gln Leu Gly
                165                 170                 175

His Gly His Thr Glu Asp Glu Ala Arg Ile Gln Pro Val Arg Ser Leu
            180                 185                 190

Gln Gly Val Arg Ile Ile Gln Ala Ala Gly Ala Ala Arg Thr Met
        195                 200                 205

Leu Ile Ser Asp Asp Gly Lys Val Tyr Ala Cys Gly Lys Glu Ser Phe
210                 215                 220

Gly Glu Ala Glu Tyr Gly Gly Gln Gly Thr Lys Pro Val Thr Thr Pro
225                 230                 235                 240

Gln Leu Val Thr Ser Leu Lys Asn Ile Phe Val Gln Ala Ala Ile
                245                 250                 255

Gly Asn Tyr Phe Thr Ala Val Leu Ser Arg Glu Gly Lys Val Tyr Thr
            260                 265                 270

Phe Ser Trp Gly Asn Asp Gly Arg Leu Gly His Gln Thr Glu Ala Ala
        275                 280                 285

Asp Val Glu Pro Arg Pro Leu Leu Gly Pro Leu Glu Asn Val Pro Val
    290                 295                 300

Val Gln Ile Ala Ala Gly Tyr Cys Tyr Leu Leu Ala Leu Ala Cys Gln
305                 310                 315                 320

Pro Asn Gly Met Ser Val Tyr Ser Val Gly Cys Gly Leu Gly Gly Lys
                325                 330                 335

Leu Gly His Gly Ser Arg Thr Asp Glu Lys Tyr Pro Arg Val Ile Glu
            340                 345                 350

Gln Phe Gln Ile Leu Asn Leu Gln Pro Arg Val Val Ala Ala Gly Ala
        355                 360                 365

Trp His Ala Ala Val Val Gly Gln Asp Gly Arg Val Cys Thr Trp Gly
    370                 375                 380

Trp Gly Arg Tyr Gly Cys Leu Gly His Gly Asn Glu Glu Cys Glu Ser
385                 390                 395                 400

Val Pro Lys Val Val Glu Gly Leu Ser His Val Lys Ala Val His Val
                405                 410                 415

Ala Thr Gly Asp Tyr Thr Thr Phe Val Val Ser Asp Asp Gly Asp Val
            420                 425                 430

Tyr Ser Phe Gly Cys Gly Glu Ser Ala Ser Leu Gly His His Pro Ser
        435                 440                 445

Phe Asp Glu Gln Gly Asn Arg His Ala Asn Val Leu Ser Pro Thr Val
    450                 455                 460

Val Thr Ser Leu Lys Gln Val Asn Glu Arg Met Val Gln Ile Ser Leu
465                 470                 475                 480

Thr Asn Ser Ile Tyr Trp Asn Ala His Thr Phe Ala Leu Thr Glu Ser
                485                 490                 495
```

```
Gly Lys Leu Phe Ala Phe Gly Ala Gly Asp Gln Gly Gln Leu Gly Thr
            500                 505                 510
Glu Leu Gly Lys Asn Gln Lys Glu Arg Cys Val Pro Glu Lys Val Asp
            515                 520                 525
Ile Asp Leu Ser
            530

<210> SEQ ID NO 9
<211> LENGTH: 432
<212> TYPE: PRT
<213> ORGANISM: Arabidopsis thaliana

<400> SEQUENCE: 9

Met Cys Asn Lys Arg Val Ile Phe Lys Pro Met Asn Glu Glu Glu Arg
1               5                   10                  15
Gln Glu Met Lys Arg Arg Cys Gly Gly Ser Trp Lys Leu Val Leu Arg
            20                  25                  30
Phe Leu Leu Ala Gly Glu Ala Cys Cys Arg Arg Glu Lys Ser Gln Ala
            35                  40                  45
Val Ala Gly Pro Gly His Ser Val Ala Val Thr Ser Lys Gly Glu Val
    50                  55                  60
Tyr Thr Phe Gly Tyr Asn Asn Ser Gly Gln Leu Gly His Gly His Thr
65                  70                  75                  80
Glu Asp Glu Ala Arg Ile Gln Pro Val Arg Ser Leu Gly Leu Val Arg
                85                  90                  95
Ile Ile Gln Ala Ala Ala Gly Ala Ala Arg Thr Met Leu Ile Ser Asp
            100                 105                 110
Asp Gly Lys Val Tyr Ala Cys Gly Lys Glu Ser Phe Gly Glu Ala Glu
        115                 120                 125
Tyr Gly Gly Gln Gly Thr Lys Pro Val Thr Thr Pro Gln Leu Val Thr
    130                 135                 140
Ser Leu Lys Asn Ile Phe Val Val Gln Ala Ala Ile Gly Asn Tyr Phe
145                 150                 155                 160
Thr Ala Val Leu Ser Arg Glu Gly Lys Val Tyr Thr Phe Ser Trp Gly
                165                 170                 175
Asn Asp Gly Arg Leu Gly His Gln Thr Glu Ala Ala Asp Val Glu Pro
            180                 185                 190
Arg Pro Leu Leu Gly Pro Leu Glu Asn Val Pro Val Val Gln Ile Ala
        195                 200                 205
Ala Gly Tyr Cys Tyr Leu Leu Ala Leu Ala Cys Gln Pro Asn Gly Met
    210                 215                 220
Ser Val Tyr Ser Val Gly Cys Gly Leu Gly Gly Lys Leu Gly His Gly
225                 230                 235                 240
Ser Arg Thr Asp Glu Lys Tyr Pro Arg Val Ile Glu Gln Phe Gln Ile
                245                 250                 255
Leu Asn Leu Gln Pro Arg Val Val Ala Ala Gly Ala Trp His Ala Ala
            260                 265                 270
Val Val Gly Gln Asp Gly Arg Val Cys Thr Trp Gly Trp Gly Arg Tyr
        275                 280                 285
Gly Cys Leu Gly His Gly Asn Glu Glu Cys Glu Ser Val Pro Lys Val
    290                 295                 300
Val Glu Gly Leu Ser His Val Lys Ala Val His Val Ala Thr Gly Asp
305                 310                 315                 320
Tyr Thr Thr Phe Val Val Ser Asp Asp Gly Asp Val Tyr Ser Phe Gly
                325                 330                 335
```

-continued

```
Cys Gly Glu Ser Ala Ser Leu Gly His His Pro Ser Phe Asp Glu Gln
            340                 345                 350

Gly Asn Arg His Ala Asn Val Leu Ser Pro Thr Val Val Thr Ser Leu
        355                 360                 365

Lys Gln Val Asn Glu Arg Met Val Gln Ile Ser Leu Thr Asn Ser Ile
    370                 375                 380

Tyr Trp Asn Ala His Thr Phe Ala Leu Thr Glu Ser Gly Lys Leu Phe
385                 390                 395                 400

Ala Phe Gly Ala Gly Asp Gln Gly Gln Leu Gly Thr Glu Leu Gly Lys
                405                 410                 415

Asn Gln Lys Glu Arg Cys Val Pro Glu Lys Val Asp Ile Asp Leu Ser
            420                 425                 430

<210> SEQ ID NO 10
<211> LENGTH: 2175
<212> TYPE: DNA
<213> ORGANISM: Lolium perenne

<400> SEQUENCE: 10
gaagcccaaa gcatcccaca caaccaagag gagagagacc ttatcaaaaa aaaagaggag      60
agagacgaca aatccgctcc ccaccccccac catcgttcct tcccagctgg tcgatcgatg    120
accttgttca tcctcatcac gctcggagct caattcgtct cctgactccg ccaagaggga    180
ggtggattat cttgagggga acggtcatgt acttcagtgc actctggtgt tgaggcctca    240
agtcaggaac accccaagtt cgagttgaaa gcatatccac tgcaagtcag agctgtcgca    300
tatggatgcc acaacgagca gcggagcttc ctcttctctt cccctccatc tcattgtgga    360
tgatacacta tccctcgttt ctccactgca gcaatcgtac caacgatcgc agcgtcattg    420
ccttggtgat tctgctcctg gggagtttcc gttggctgca aacccatcaa tagtcctcca    480
tgtcctcaca tcatgcaatc tagaacccga ggacctcgct cacttggagg caacatgcaa    540
attcttcagg aagcctgcca atttccctcc tgacttccta ttgtcaatgt cggaacttgc    600
ggctttcgac atgtgccaga tcgtgctat atttaagcct atgggtacac aagaaaaaga     660 aatgttttaag cagcgctgcg gcggtacctg gaagctagtg cttaggttca taactctagg   720
tgaagcatgt tgtcggcgag aaaaatctca ggcaattgct ggacctggcc acagcgtcgc    780
tgtgacagca agtggcgctg cttactcttt tgggtccaac aactccggcc aacttggcca    840
tgaccgttta gaagaggagt ggagaccacg tcccatcaga tcattgcagg gtattcgaat    900
tattcaggca gcagcaggag cagggcgtac tatgctcgtt agtgatgctg gtagggtgta    960
tgcatttggg aaggattcct ttggagaggt agaatatggg aatcaaggtt caagggttgt   1020
gactacgcca cagttggtgg aatcattgaa ggacatatac attgtacagg ctgcaatagg   1080
gaacttcttt actgctgtgt tatctcggga gggatgcgta tatacatttt cttggggtgg   1140
cgacatgaaa cttggtcacc aaacagagcc aaacgatgta cagcctcatc ttctcgcagg   1200
ccctcttgag gacattccag tagtgcagat agctgcaggc tactgctatc tccttcttct   1260
ggcatgccaa ccaagtggca tgtctgttta ttctgttggt tgtggtttag agggaagct    1320 tggccatggc tcgcgaagtg atgagaaata ccctaggttg attgagcagt ccagaccct    1380 gaatatacag ccagtggtgg ttgctgcggg tgcttggcat gctgctgttg tgggcaagga   1440
tgggcgagtt tgtacttggg gatgggggcg ttatggctgc ttgggcatg gtaatgagga    1500 atgtgagtct gttcccaagg tagttgagac cttgagcagt gtgaaggctg tccatgtagc   1560
aaccggagat tacaccacat ttgttgtgtc acataaaggt gatgtttact cgtttggatg   1620
```

```
tggtgaatca tcaagccttg gccacaatac tgcgattgag ggtaataaca ggcacagcaa    1680
tgtccttagc cctgagctgg tgacctcttc gcagagaacc gatgaaaggg tggtgcatgt    1740
cagcctaacg aattccatat actggaatgc acatacattt gcactgacag agtcagcaaa    1800
attgtatgca ttcggcgcag gggacaaagg acagctaggc actgaacttg tcgaacaccg    1860
aagcgagagg ggtaccccgg agcaggtcga tattgacctc aattaggttc agttgcagca    1920
caatgcctcc ctttcgccct tttgcttcag ttgcacactt ctaaccatca cttttctaac    1980
tcaccactct ttgcattgca tgctcctagt ctgtaccgcg ttgatccttg tcaatattgt    2040
tagatttgtt agccagcaaa acaaggaatt tgttttcat  atgattgatt ctctttagaa    2100
agcttgtgta tatatttgtg attgtaaata taacaagcag gtcttcttgt cagttccttc    2160
aaacatgagc cgctg                                                     2175

<210> SEQ ID NO 11
<211> LENGTH: 2237
<212> TYPE: DNA
<213> ORGANISM: Oryza sativa

<400> SEQUENCE: 11
ggcttttctc tctctcctct cctctctctc tctctctctc tctcccttct ccacgcacgc      60
acatcatcat tattgggagg ctcgtccctg tccgtcgctc gcctgctctc atcctctccc     120
tctctctctc ctcccccgtt tctcggttag attcacgcct ctccaacctc ctcccccaac     180
cccaagaatt cccgatcgat tgattgactg gccgacccgc ccgttgaatg gtcctgtact     240
taattcactc tggacttctg gagagccagg aacaccacaa gtttgagata aagcataag     300 gcagtgcaag tcgcagccgt ggcagatgga cgccacgacg agcagtggag cttcctcctc     360
tctacccctc caccttatca tagatgatgc tcttgcccct gtttctccgt tgcagcagtc     420
gtttcagagg tcacgcgcc  attgcttttgg tggctctgct cctggagaat tcccctttggc    480 tgcaaaccca tcaattgtcc tccatgtcct cacatcatgc aatctggaac ctgatgacct     540
cgctcacttg gaggcaacat gctcgttttt ccggaagcct gccaatttcc ctccgatttt    600
tcagttgtca atgtcagaac tcgcagcgtt ggatatgtgc cagaaacggg cgatatttaa     660
acctatgact caacaagaaa gagaaatgtt taagcaacgt tgcggcggga gttggaagct     720
ggttcttagg tttataatgg caggtgaagc atgttgccgg agggaaaaat ctcaggcaat     780
cgctggacct ggtcacagca tcgctgtgac aacaagcggt gcagtgtata cttttgggtc     840
caacagctct ggtcaacttg gccatggtag tttagaagag gagtggaggc cacggattat     900
cagatcattg cagggtatta gaattattca gcggcagca  ggagcaggac gcacaatgct     960
tgttagtgat gctggtaggg tctatgcatt tggaaaggat tcatttggag aagtggaata    1020
tgcagcccaa ggttctaggg ttgtcaccac accacagctg gtggaatcat tgaaggacat    1080
atacattgtc caggcagcaa tcgggaactt ctttactgca gttttatctc gggaaggtca    1140
tgtgtataca ttttcttggg ggaatgacat gaaacttggt catcagacag agccaaatga    1200
tgttcagcct catcttctag caggccctct tgagaacatt ccagttgtgc agattgccgc    1260
aggctactgc tatctcctgg ctctggcatg ccaaccaagt ggcatgtctg tttattctgt    1320
tggttgtggg ttaggtggga acttggcca  tggttctcga accgatgaga aatacccag     1380 gttaatcgag cagttccaag ctttgaatat acaaccagta gtggttgctg ctggtgcttg    1440
gcatgctgct gttgtaggca aggatgggcg tgtttgcact tggggatggg ggcggtatgg    1500
ctgcttgggt cacggtaatg aggaatgtga gtctgttcct aaggttgttg agtccttagt    1560
```

-continued

```
caatgtgagg gctgtccatg tagcaactgg agattacacc acatttgttg tatctgataa    1620
aggtgatgtt tactcgtttg gatgtggtga atcatcaagt cttggccaca acactataac    1680
tgagggtaat aataggcaca ctaatgtcct tagcccggag ttggtgactt ctttgaagag    1740
aacaaatgaa agggttgctc agatcagcct cactaactcc atttactgga atgcacatac    1800
atttgcactg acagattcag gaaaactcta tgcgtttggt gcaggggaca aagggcagct    1860
aggtaccgaa ctcgtcgcgc aggaaagcga gaggggaca ccggagcgtg ttgaaattga     1920
cctcagttag gtccaaattg caacgccact tcatctcctt ttctctccag atgcactctt    1980
ctaacgttaa ctttcaaatt gattgcattg cgcgcccttt agcttgttgg ctgttcatca    2040
gcctcatcct gctctgcagc taatccttgt gaaaatagtt accatcaatt aaacagtctg    2100
ttgttcatat gattggttcg gtttagaaac tttgtatata tgattatcat gtaaatataa    2160
cagtcaggtc tcattgccag ttcctttaaa acatgagtag ctggctttta acatcctgtg    2220
aaatttacct taactct                                                   2237

<210> SEQ ID NO 12
<211> LENGTH: 2237
<212> TYPE: DNA
<213> ORGANISM: Oryza sativa

<400> SEQUENCE: 12
ggcttttctc tctctcctct cctctctctc tctctctctc tctcccttct ccacgcacgc      60
acatcatcat tatgggagg ctcgtccctg tccgtcgctc gcctgctctc atcctctccc      120
tctctctctc ctccccgtt tctcggttag attcacgcct ctccaacctc ctcccccaac      180
cccaagaatt cccgatcgat tgattgactg gccgacccgc ccgttgaatg gtcctgtact     240
taattcactc tggacttctg gagagccagg aacaccacaa gtttgagata aaagcataag     300
gcagtgcaag tcgcagccgt ggcagatgga cgccacgacg agcagtggag cttcctcctc     360
tctacccctc caccttatca tagatgatgc tcttgcccct gtttctccgt tgcagcagtc     420
gtttcagagg tcacgcgcc attgcttttgg tggctctgct cctggagaat tccccttggc      480
tgcaaaccca tcaattgtcc tccatgtcct cacatcatgc aatctggaac ctgatgacct     540
cgctcacttg gaggcaacat gctcgttttt ccggaagcct gccaatttcc ctccgatttt     600
tcagttgtca atgtcagaac tcgcagcgtt ggatatgtgc cagaaacggg cgatatttaa     660
acctatgact caacaagaaa gagaaatgtt taagcaacgt tgcggcggga gttggaagct     720
ggttcttagg tttataatgg caggtgaagc atgttgccgg agggaaaaat ctcaggcaat     780
cgctggacct ggtcacagca tcgctgtgac aacaagcggt gcagtgtata cttttgggtc     840
caacagctct ggtcaacttg gccatggtag tttagaagag gagtggaggc cacgagttat     900
cagatcattg cagggtatta gaattattca agcggcagca ggagcaggac gcacaatgct     960
tgttagtgat gctggtaggg tctatgcatt tggaaaggat tcatttggag aagtggaata    1020
tgcagcccaa ggttctaggg ttgtcaccac accacagctg gtggaatcat tgaaggacat    1080
atacattgtc caggcagcaa tcgggaactt ctttactgca gttttatctc gggaaggtca    1140
tgtgtataca ttttcttggg ggaatgacat gaaacttggt catcagacag agccaaatga    1200
tgttcagcct catcttctag caggccctct tgagaacatt ccagttgtgc agattgccgc    1260
aggctactgc tatctcctgg ctctggcatg ccaaccaagt ggcatgtctg tttattctgt    1320
tggttgtggg ttaggtggga aacttggcca tggttctcga accgatgaga aatacctag    1380 gttaatcgag cagttccaag ctttgaatat acaaccagta gtggttgctg ctggtgcttg    1440
```

```
gcatgctgct gttgtaggca aggatgggcg tgtttgcact tggggatggg ggcggtatgg    1500
ctgcttgggt cacggtaatg aggaatgtga gtctgttcct aaggttgttg agtccttagt    1560
caatgtgagg gctgtccatg tagcaactgg agattacacc acatttgttg tatctgataa    1620
aggtgatgtt tactcgtttg gatgtggtga atcatcaagt cttggccaca acactataac    1680
tgagggtaat aataggcaca ctaatgtcct tagcccggag ttggtgactt ctttgaagag    1740
aacaaatgaa agggttgctc agatcagcct cactaactcc atttactgga atgcacatac    1800
atttgcactg acagattcag gaaaactcta tgcgtttggt gcagggggaca aagggcagct    1860 aggtaccgaa ctcgtcgcgc aggaaagcga gaggggggaca ccggagcgtg ttgaaattga    1920
cctcagttag gtccaaattg caacgccact tcatctcctt ttctctccag atgcactctt    1980
ctaacgttaa ctttcaaatt gattgcattg cgcgcccttt agcttgttgg ctgttcatca    2040
gcctcatcct gctctgcagc taatccttgt gaaaatagtt accatcaatt aaacagtctg    2100
ttgttcatat gattggttcg gtttagaaac tttgtatata tgattatcat gtaaatataa    2160
cagtcaggtc tcattgccag ttcctttaaa acatgagtag ctggctttta acatcctgtg    2220
aaatttacct taactct                                                   2237

<210> SEQ ID NO 13
<211> LENGTH: 2145
<212> TYPE: DNA
<213> ORGANISM: Oryza sativa

<400> SEQUENCE: 13
gattgattct ccgacgattt tgtccaacgc tacgagaatg gtcctgtact taattcactc      60
tggacttctg gagagccagg aacaccacaa gtttgagata aaagcataag gcagtgcaag     120
tcgcagccgt ggcagatgga cgccacgacg agcagtggag cttcctcctc tctacccctc     180
caccttatca tagatgatgc tcttgccctt gtttctccgt tgcagcagtc gtttcagagg     240
tcacagcgcc attgctttgg tggctctgct cctggagaat tccccttggc tgcaaaccca     300
tcaattgtcc tccatgtcct cacatcatgc aatctggaac ctgatgacct cgctcacttg     360
gaggcaacat gctcgttttt ccggaagcct gccaatttcc ctcccgattt tcagttgtca     420
atgtcagaac tcgcagcgtt ggatatgtgc cagaaacggg cgatatttaa acctatgact     480
caacaagaaa gagaaatgtt taagcaacgt tgcggcggga gttggaagct ggttcttagg     540
tttataatgg caggtgaagc atgttgccgg agggaaaaat ctcaggcaat cgctggacct     600
ggtcacagca tcgctgtgac aacaagcggt gcagtgtata cttttgggtc caacagctct     660
ggtcaacttg gccatggtag tttagaagag gagtggaggc cacggattat cagatcattg     720
cagggtatta gaattattca agcggcagca ggagcaggac gcacaatgct tgttagtgat     780
gctggtaggg tctatgcatt tggaaaggat tcatttggag aagtggaata tgcagcccaa     840
ggttctaggg ttgtcaccac accacagctg gtggaatcat tgaaggacat atacattgtc     900
caggcagcaa tcgggaactt ctttactgca gttttatctc gggaaggtca tgtgtataca     960
ttttcttggg ggaatgacat gaaacttggt catcagacag agccaaatga tgttcagcct    1020
catcttctag caggccctct tgagaacatt ccagttgtgc agattgccgc aggctactgc    1080
tatctcctgg ctctggcatg ccaaccaagt ggcatgtctg tttattctgt tggttgtggg    1140
ttaggtggga aacttggcca tggttctcga accgatgaga aataccctag gttaatcgag    1200
cagttccaag ctttgaatat acaaccagta gtggttgctg ctggtgcttg gcatgctgct    1260
gttgtaggca aggatgggcg tgtttgcact tggggatggg ggcggtatgg ctgcttgggt    1320
```

-continued

```
cacggtaatg aggaatgtga gtctgttcct aaggttgttg agtccttagt caatgtgagg    1380
gctgtccatg tagcaactgg agattacacc acatttgttg tatctgataa aggtgatgtt    1440
tactcgtttg gatgtggtga atcatcaagt cttggccaca acactataac tgagggtaat    1500
aataggcaca ctaatgtcct tagcccggag ttggtgactt ctttgaaaag aacaaatgaa    1560
agggttgctc agatcagcct cactaactcc atttactgga atgcacatac atttgcactg    1620
acagattcag gaaaactcta tgcgtttggt gcagggaca aagggcagct aggtaccgaa     1680
ctcgtcgcgc aggaaagcga gaggggggaca ccggagcgtg ttgaaattga cctcagttag   1740
gtccaaattg caacgccact tcatctcctt ttctctccag atgcactctt ctaacgttaa    1800
cttccaaatt gattgcattg cgcgcccttt agcttgttgg ctgttcatca gcctcatcct    1860
gctctgcagc taatccttgt gaaaatagtt accatcaatt aaacagtctg ttgttcatat    1920
gattggttcg gtttagaaac tttgtatata tgattatcat gtaaatataa cagtcaggtc    1980
tcattgccag ttccttttaaa acatgagtag ctggctttta acatcctgtg aaatttacct   2040
taactctaca tctgcaccat ttatatttct tctaaacagg ggtgtgtgtg tgtgtgagag    2100
agagatataa taatatatat ttatatattt atttctagtt gattg                    2145

<210> SEQ ID NO 14
<211> LENGTH: 2405
<212> TYPE: DNA
<213> ORGANISM: Oryza sativa

<400> SEQUENCE: 14
tctgggtttg ggggcactgt tttgagattt cagttgtttt cttcctttgt ttccttgatt     60
tttggaggtt gttttgcatc tgatttagtg tctgtttgcc atccagaaga atatggcatc    120
tctatatgtt tggtcaggt gatatgctct gtttgattgc attgactttg ggaatgcttt    180
caattattga tatgctctga ttgtttgttt acaagtgttg gatggattct ttctcatcca    240
cttttctgat tcggatgaat aatataacat attattgttt aattgtgtta aactaaggtg    300
tgctgatggg cttgttagag aagttactta acaattaatg attgtagtta catgtcttga    360
ttacattaat gcattgcaca ttacagaatg gtcctgtact taattcactc tggacttctg    420
gagagccagg aacaccacaa gtttgagata aagcataag gcagtgcaag tcgcagccgt     480
ggcagatgga cgccacgacg agcagtggag cttcctcctc tctacccctc caccttatca    540
tagatgatgc tcttgcccctt gtttctccgt tgcagcagtc gtttcagagg tcacagcgcc    600
attgctttgg tggctctgct cctggagaat tccccttggc tgcaaaccca tcaattgtcc    660
tccatgtcct cacatcatgc aatctggaac ctgatgacct cgctcacttg gaggcaagta    720
gtgttttgtt cttcctctcc aatgtagaat tgatattgcc actgatgaaa tttgtgcttg    780
cgataggcaa catgctcgtt tttccggaag cctgccaatt tccctcccga ttttcagttg    840
tcaatgtcag aactcgcagc gttggatatg tgccagaaac gggcgatatt taaacctatg    900
actcaacaag aaagagaaat gtttaagcaa cgttgcggcg ggagttggaa gctggttctt    960
aggtttataa tggcaggtga agcatgttgc cggagggaaa atctcaggc aatcgctgga     1020
cctggtcaca gcatcgctgt gacaacaagc ggtgcagtgt atacttttgg gtccaacagc    1080
tctggtcaac ttggccatgg tagtttagaa gaggagtgga ggccacggat tatcagatca    1140
ttgcagggta ttagaattat tcaagcggca gcaggagcag gacgcacaat gcttgttagt    1200
gatgctggta gggtctatgc atttggaaag gattcatttg gagaagtgga atatgcagcc    1260
caaggttcta gggttgtcac cacaccacag ctggtggaat cattgaagga catatacatt    1320
```

```
gtccaggcag caatcgggaa cttctttact gcagttttat ctcgggaagg tcatgtgtat   1380
acattttctt gggggaatga catgaaactt ggtcatcaga cagagccaaa tgatgttcag   1440
cctcatcttc tagcaggccc tcttgagaac attccagttg tgcagattgc cgcaggctac   1500
tgctatctcc tggctctggc atgccaacca agtggcgtgt ctgtttattc tgttggttgt   1560
gggttaggtg ggaaacttgg ccatggttct cgaaccgatg agaaataccc taggttaatc   1620
gagcagttcc aagctttgaa tatacaacca gtagtggttc tgctggtgc ttggcatgct   1680 gctgttgtag caaggatgg gcgtgtttgc acttgggat gggggcggta tggctgcttg   1740
ggtcacggta atgaggaatg tgagtctgtt cctaaggttg ttgagtcctt agtcaatgtg   1800
agggctgtcc atgtagcaac tggagattac accacatttg ttgtatctga taaaggtgat   1860
gtttactcgt ttgatgtgg tgaatcatca agtcttggcc acaacactat aactgagggt   1920
aataataggc acactaatgt ccttagcccg gagttggtga cttcttttgaa aagaacaaat   1980 gaaagggttg ctcagatcag cctcactaac tccatttact ggaatgcaca tacatttgca   2040
ctgacagatt caggaaaact ctatgcgttt ggtgcagggg acaaagggca gctaggtacc   2100
gaactcgtcg cgcaggaaag cgagagggggg acaccggagc gtgttgaaat tgacctcagt   2160
taggtccaaa ttgcaacgcc acttcatctc cttttctctc cagatgcact cttctaacgt   2220
taactttcaa attgattgca ttgcgcgccc tttagcttgt tggctgttca tcagcctcat   2280
cctgctctgc agctaatcct tgtgaaaata gttaccatca attaaacagt ctgttgttca   2340
tatgattggt tcggtttaga aactttgtat atatgattat catgtaaata taacagtcag   2400
gtccc                                                                2405

<210> SEQ ID NO 15
<211> LENGTH: 1313
<212> TYPE: DNA
<213> ORGANISM: Oryza sativa

<400> SEQUENCE: 15
tattcaagcg gcagcaggag caggacgcac aatgcttgtt agtgatgctg gtagggtcta     60
tgcatttgga aaggattcat ttggagaagt ggaatatgca gcccaaggtt ctagggttgt    120
caccacacca cagctggtgg aatcattgaa ggacatatac attgtccagg cagcaatcgg    180
gaacttcttt actgcagttt tatctcggga aggtcatgtg tatacatttt cttgggggaa    240
tgacatgaaa cttggtcatc agacagagcc aaatgatgtt cagcctcatc ttctagcagg    300
ccctcttgag aacattccag ttgtgcagat gccgcaggc tactgctatc tcctggctct    360
ggcatgccaa ccaagtggca tgtctgttta ttctgttggt tgtgggttag gtgggaaact    420
tggccatggt tctcgaaccg atgagaaata ccctaggtta atcgagcagt tccaagcttt    480
gaatatacaa ccagtagtgg ttgctgctgg tgcttggcat gctgctgttg taggcaagga    540
tgggcgtgtt tgcacttggg gatgggggcg tatggctgc ttgggtcacg gtaatgagga    600
atgtgagtct gttcctaagg ttgttgagtc cttagtcaat gtgagggctg tccatgtagc    660
aactggagat tacaccacat ttgttgtatc tgataaaggt gatgtttact cgtttggatg    720
tggtgaatca tcaagtcttg ccacaacac tataactgag gtaataata ggcacactaa    780 tgtccttagc ccggagttgg tgacttcttt gaaaagaaca atgaaaggg ttgctcagat    840 cagcctcact aactccattt actggaatgc acatacattt gcactgacag attcaggaaa    900
actctatgcg tttggtgcag gggacaaagg gcagctaggt accgaactcg tcgcgcagga    960
aagcgagagg gggacaccgg agcgtgttga aattgacctc agttaggtcc aaattgcaac   1020
```

-continued

| | |
|---|---|
| gccacttcat ctcctttct ctccagatgc actcttctaa cgttaacttt caaattgatt | 1080 |
| gcattgcgcg ccctttagct tgttggctgt tcatcagcct catcctgctc tgcagctaat | 1140 |
| ccttgtgaaa atagttacca tcaattaaac agtctgttgt tcatatgatt ggttcggttt | 1200 |
| agaaactttg tatatatgat tatcatgtaa atataacagt caggtctcat tgccagttcc | 1260 |
| tttaaaacat gagtagctgg ctttaacat cctgtgaaat ttaccttaac tct | 1313 |

<210> SEQ ID NO 16
<211> LENGTH: 2012
<212> TYPE: DNA
<213> ORGANISM: Oryza sativa

<400> SEQUENCE: 16

| | |
|---|---|
| ctctttctc ctccaaggtg accacctcct ccccaccgcc cccacatcc ggttccccga | 60 |
| ggttgcagcc tctgcagcct tgcgaggatc agatgaaccc atcgtcacca gacgaattct | 120 |
| ccaactgagt actctgctcc cataatccta tttatccaca cagcgagggg cactgcaaga | 180 |
| agcatgcagt gcccaatgga cgcagctgca agtggaactt cgcctgtgat gcagttccat | 240 |
| ggcattgttg atgagccacc ctcccattca tctccgctgc acacggcgct ggaacgttcg | 300 |
| cagcgccatt gctatggtca tgaaacccca ggagaattcc cccttgctgt gagcccctcc | 360 |
| attgtgctac atgtgctctc cacctgcgag ctagatccta aagatctcgc tgcactggag | 420 |
| gctacatgta cattcttcag taaacctgca aatttcgagc caaactttgc tctatcgctt | 480 |
| ccagaggttg cggcatttga tatgtgccat aaaagaccca tggttaagct aatggcacag | 540 |
| caggaacggg agcaactgaa gcagaggtgt ggtggatctt ggaagcttgt tttcaagtat | 600 |
| attgtggcta gagaaaggaa ttactctcgg attgtcgccg ggccgggcca tagtattgtt | 660 |
| gtcaccacaa agggagatgc atactcattt ggggctaatt gctggggcca gcttggcctt | 720 |
| ggggatactg aagatcggtt caagccatgc cttattaggt cttttgcaaag catcaaaatc | 780 |
| acacaggctg cagttggatc aaggcagaca atgcttgtga gtgacacagg aagtgtctat | 840 |
| gcatttggga agggtagctt tgtgtgggaa gagcttttctg atgcagctga tcacattacc | 900 |
| actcctaaga tagtggagtc gctaaagggt gtgtttgtag ttcaagcagc cattggtggt | 960 |
| tacttctctg cgtttctatc tagagagggt caggtttaca cgatctcgtg ggggcgaacc | 1020 |
| gagaggcttg gccatagttc ggatccttca gatgttgagc ctcgtcttct ctctggacca | 1080 |
| cttgagggtg ttcttgttgc acagattct gctgggaatt gctatctcct tatgttggcc | 1140 |
| taccagccaa ctggaatgtc agtgtattct gtaggctgtg gtttaggagg caagcttggt | 1200 |
| cacggatgca aaaacaataa gggcaccccc aagttgattg aacatttcct gacattgagc | 1260 |
| tttaatccgg tttcagttgc ggctggcact tggcatgctg cagctctagg tgacgatggg | 1320 |
| cgtgtctgca cctggggttg gggccatact ggttgtttgg acatggcga tgaggagtac | 1380 |
| agggttctcc ccactgtggt tcaaggattg agcaatgtga aggctgtgca tgtctccacc | 1440 |
| ggtgaataca ccacctttgt tgtctccgat aacggcgata catactcctt tggatccgct | 1500 |
| gaatccctga atataggttt ccaggaggat gaggaagcag cagatgatgc agatttttct | 1560 |
| accccaagct tggtagaatc actgaaggtg ttgaatgata aggctgtaca gattagcaca | 1620 |
| acaaattctt catattggct caactcagaa atgggatacc cgcatacgtt cgcgctcatg | 1680 |
| gaatccggta aactgtatgc ctttggggga gggatcaaag gccagcttgg tgtcaagctc | 1740 |
| tctgagggtc aagaaagagc tcagaaccca gagcgagtcc cgatcgatct ctgctaattt | 1800 |
| caaccagcat tctggtgacc atttgcaatg acatattctg tgatctgtgg ttagcatgcc | 1860 |

```
ctcctgaatt tcataggagg aactcaaatg ttagcatcga tgtaaatact aggggcactt    1920
acctttggtt cttctctgaa gtaacagtgt ggttgttggt agttcttgca ttttgaattg    1980
ttggtgcagc caagtcctga ccgagtcttc tg                                  2012
```

<210> SEQ ID NO 17
<211> LENGTH: 1599
<212> TYPE: DNA
<213> ORGANISM: Arabidopsis thaliana

<400> SEQUENCE: 17

```
atggatgcta cgagtggaac tccgagttta cagtatatta acttgccgga caatctgtt     60 tcgactactt ctcctcctgt gtcaccattt cagaggccaa acgacattg ctttggtgac    120 acaactccag gagagtttcc tttagcagct aacccttcca ttgtcctaca tgttctcact    180
gaatgtagat tggatcctcg tgacctcgct aatctcgagg caacatgctc gttctttagc    240
cagccagcaa actttgcccc ggacattaac ctatcactat cggagctcgc tgctctcgac    300
atgtgtaata aagggtgat tttcaagccg atgaatgaag aagaacgtca agagatgaaa    360
cgtaggtgcg gaggatcatg gaaattagtc cttcggtttt tgctggctgg tgaagcgtgt    420
tgtcgaagag agaaatctca agctgttgct ggtcctggtc atagtgtagc agtcacatcg    480
aaaggagaag tttatacttt cggatataat aactctggac agctaggaca tggtcatacc    540
gaggacgaag ctcgaattca acctgttaga tcattgcagg gagttcgaat catccaagca    600
gctgctggtg ctgctcggac aatgctaata agcgatgacg aaaagttta tgcgtgtgga    660 aaagaatcct tcggggaagc tgaatacgga gggcaaggga ctaaaccagt tacaactcct    720
cagcttgtaa catctttaaa aaacatattt gtagtgcaag cagctattgg gaattacttt    780
accgctgttc tctcccgaga aggaaaggtt tatacattct cgtggggcaa tgacggtaga    840
ctaggacacc aaactgaggc tgcggatgtc gagcctcgtc ctttgttagg cccactcgag    900
aatgtacccg ttgtgcagat tgctgctggt tattgctacc ttcttgcctt agcctgtcaa    960
ccaaatggca tgtctgtta ctcagttggt tgcggttttgg gaggcaaact tggtcatggg   1020
tcaagaacag atgagaagta tcctcgggtc atcgagcagt tcagatatt gaatcttcaa    1080 cctagggtag ttgcagcggg tgcttggcat gccgcggtgg taggtcagga tggaagagtg   1140
tgcacttggg gttggggaag atatggatgt ttaggtcacg taacgagga gtgtgaatca   1200 gtccctaagg ttgttgaagg tctaagccat gtcaaagcag ttcatgtcgc aacaggagac   1260
tacactactt ttgtggtctc agacgatggt gatgtttact cgtttggctg cggcgaatcc   1320
gctagtctcg gtcaccatcc atcctttgat gaacaggta atcgacatgc aaacgtgcta   1380
agtccaacgg tagtaacatc gctaaaacaa gtgaacgagc ggatggtcca gataagtcta   1440
acgaactcca tatactggaa cgctcataca tttgcgctca cggaatcggg gaagctattc   1500
gcgtttggtg caggcgatca gggtcagctt ggaacagagc ttggtaagaa ccaaaaagaa   1560
aggtgtgtac cggaaaaagt ggatatcgat ctcagctag                          1599
```

<210> SEQ ID NO 18
<211> LENGTH: 1330
<212> TYPE: DNA
<213> ORGANISM: Arabidopsis thaliana

<400> SEQUENCE: 18

```
atgtgtaata aagggtgat tttcaagccg atgaatgaag aagaacgtca agagatgaaa     60
cgtaggtgcg gaggatcatg gaaattagtc cttcggtttt tgctggctgg tgaagcgtgt    120
```

| | |
|---|---|
| tgtcgaagag agaaatctca agctgttgct ggtcctggtc atagtgtagc agtcacatcg | 180 |
| aaaggagaag tttatacttt cggatataat aactctggac agctaggaca tggtcatacc | 240 |
| gaggacgaag ctcgaattca acctgttaga tcattgcagg gagttcgaat catccaagca | 300 |
| gctgctggtg ctgctcggac aatgctaata agcgatgacg gaaaagttta tgcgtgtgga | 360 |
| aaagaatcct tcggggaagc tgaatacgga gggcaaggga ctaaaccagt tacaactcct | 420 |
| cagcttgtaa catctttaaa aaacatattt gtagtgcaag cagctattgg gaattacttt | 480 |
| accgctgttc tctcccgaga aggaaaggtt tatacattct cgtggggcaa tgacggtaga | 540 |
| ctaggacacc aaactgaggc tgcggatgtc gagcctcgtc ctttgttagg cccactcgag | 600 |
| aatgtacccg ttgtgcagat tgctgctggt tattgctacc ttcttgcctt agcctgtcaa | 660 |
| ccaaatggca tgtctgttta ctcagttggt tgcggtttgg gaggcaaact tggtcatggg | 720 |
| tcaagaacag atgagaagta cctcgggtc atcgagcagt ttcagatatt gaatcttcaa | 780 |
| cctagggtag ttgcagcggg tgcttggcat gccgcggtgg taggtcagga tggaagagtg | 840 |
| tgcacttggg gttggggaag atatggatgt ttaggtcacg gtaacgagga gtgtgaatca | 900 |
| gtccctaagg ttgttgaagg tctaagccat gtcaaagcag ttcatgtcgc aacaggagac | 960 |
| tacactactt ttgtggtctc agacgatggt gatgtttact cgtttggctg cggcgaatcc | 1020 |
| gctagtctcg gtcaccatcc atcctttgat gaacagggta atcgacatgc aaacgtgcta | 1080 |
| agtccaacgg tagtaacatc gctaaaacaa gtgaacgagc ggatggtcca gataagtcta | 1140 |
| acgaactcca tatactggaa cgctcataca tttgcgctca cggaatcggg gaagctattc | 1200 |
| gcgtttggtg caggcgatca gggtcagctt ggaacagagc ttggtaagaa ccaaaaagaa | 1260 |
| aggtgtgtac cggaaaaagt ggatatcgat ctcagctagc tagctgactt atgtggtttg | 1320 |
| gttggtaaga | 1330 |

<210> SEQ ID NO 19
<211> LENGTH: 12159
<212> TYPE: DNA
<213> ORGANISM: Artificial
<220> FEATURE:
<223> OTHER INFORMATION: Vector

<400> SEQUENCE: 19

| | |
|---|---|
| ggaattcgat atcaagcttg gcactggccg tcgttttaca acgtcgtgac tgggaaaacc | 60 |
| ctggcgttac ccaacttaat cgccttgcag cacatccccc tttcgccagc tggcgtaata | 120 |
| gcgaagaggc ccgcaccgat cgcccttccc aacagttgcg cagcctgaat ggcgaatgct | 180 |
| agagcagctt gagcttggat cagattgtcg tttcccgcct tcagtttaaa ctatcagtgt | 240 |
| ttgacaggat atattggcgg gtaaacctaa gagaaaagag cgtttattag aataacggat | 300 |
| atttaaaagg cgtgaaaag tttatccgt tcgtccattt gtatgtgcat gccaaccaca | 360 |
| gggttcccct cgggatcaaa gtactttgat ccaaccctc cgctgctata gtgcagtcgg | 420 |
| cttctgacgt tcagtgcagc cgtcttctga aaacgacatg tcgcacaagt cctaagttac | 480 |
| gcgacaggct gccgccctgc cctttttcctg gcgttttctt gtcgcgtgtt ttagtcgcat | 540 |
| aaagtagaat acttgcgact agaaccggag acattacgcc atgaacaaga gcgccgccgc | 600 |
| tggcctgctg ggctatgccc gcgtcagcac cgacgaccag gacttgacca accaacgggc | 660 |
| cgaactgcac gcggccggct gcaccaagct gttttccgag aagatcaccg gcaccaggcg | 720 |
| cgaccgcccg gagctggcca ggatgcttga ccacctacgc cctggcgacg ttgtgacagt | 780 |
| gaccaggcta gaccgcctgg cccgcagcac ccgcgaccta ctggacattg ccgagcgcat | 840 |

```
ccaggaggcc ggcgcgggcc tgcgtagcct ggcagagccg tgggccgaca ccaccacgcc    900
ggccggccgc atggtgttga ccgtgttcgc cggcattgcc gagttcgagc gttccctaat    960
catcgaccgc acccggagcg ggcgcgaggc cgccaaggcc cgaggcgtga agtttggccc   1020
ccgccctacc ctcaccccgg cacagatcgc gcacgcccgc gagctgatcg accaggaagg   1080
ccgcaccgtg aaagaggcgg ctgcactgct tggcgtgcat cgctcgaccc tgtaccgcgc   1140
acttgagcgc agcgaggaag tgacgcccac cgaggccagg cggcgcggtg ccttccgtga   1200
ggacgcattg accgaggccg acgccctggc ggccgccgag aatgaacgcc aagaggaaca   1260
agcatgaaac cgcaccagga cggccaggac gaaccgtttt tcattaccga agagatcgag   1320
gcggagatga tcgcggccgg gtacgtgttc gagccgcccg cgcacgtctc aaccgtgcgg   1380
ctgcatgaaa tcctggccgg tttgtctgat gccaagctgg cggcctggcc ggccagcttg   1440
gccgctgaag aaaccgagcg ccgccgtcta aaaggtgat gtgtatttga gtaaaacagc    1500
ttgcgtcatg cggtcgctgc gtatatgatg cgatgagtaa ataaacaaat acgcaagggg   1560
aacgcatgaa ggttatcgct gtacttaacc agaaaggcgg gtcaggcaag acgaccatcg   1620
caacccatct agcccgcgcc ctgcaactcg ccggggccga tgttctgtta gtcgattccg   1680
atccccaggg cagtgcccgc gattgggcgg ccgtgcggga agatcaaccg ctaaccgttg   1740
tcggcatcga ccgcccgacg attgaccgcg acgtgaaggc catcggccgg cgcgacttcg   1800
tagtgatcga cggagcgccc caggcggcgg acttggctgt gtccgcgatc aaggcagccg   1860
acttcgtgct gattccggtg cagccaagcc cttacgacat atgggccacc gccgacctgg   1920
tggagctggt taagcagcgc attgaggtca cggatggaag gctacaagcg gcctttgtcg   1980
tgtcgcgggc gatcaaaggc acgcgcatcg gcggtgaggt tgccgaggcg ctggccgggt   2040
acgagctgcc cattcttgag tcccgtatca cgcagcgcgt gagctaccca ggcactgccg   2100
ccgccggcac aaccgttctt gaatcagaac ccgagggcga cgctgcccgc gaggtccagg   2160
cgctggccgc tgaaattaaa tcaaaactca tttgagttaa tgaggtaaag agaaaatgag   2220
caaaagcaca aacacgctaa gtgccggccg tccgagcgca cgcagcagca aggctgcaac   2280
gttggccagc ctggcagaca cgccagccat gaagcgggtc aactttcagt tgccggcgga   2340
ggatcacacc aagctgaaga tgtacgcggt acgccaaggc aagaccatta ccgagctgct   2400
atctgaatac atcgcgcagc taccagagta aatgagcaaa tgaataaatg agtagatgaa   2460
ttttagcggc taaaggaggc ggcatggaaa atcaagaaca accaggcacc gacgccgtgg   2520
aatgccccat gtgtggagga acgggcggtt ggccaggcgt aagcggctgg gttgtctgcc   2580
ggccctgcaa tggcactgga accccaagc cgaggaatc ggcgtgacgg tcgcaaacca    2640
tccgcccgc tacaaatcgg cgcggcgctg ggtgatgacc tggtggagaa gttgaaggcc    2700
gcgcaggccg cccagcggca acgcatcgag gcagaagcac gccccggtga atcgtggcaa   2760
gcggccgctg atcgaatccg caaagaatcc cggcaaccgc cggcagccgg tgcgccgtcg   2820
attaggaagc cgcccaaggg cgacgagcaa ccagattttt tcgttccgat gctctatgac   2880
gtgggcaccc gcgatagtcg cagcatcatg gacgtggccg ttttccgtct gtcgaagcgt   2940
gaccgacgag ctggcgaggt gatccgctac gagcttccag acgggcacgt agaggtttcc   3000
gcagggccgg ccggcatggc cagtgtgtgg gattacgacc tggtactgat ggcggtttcc   3060
catctaaccg aatccatgaa ccgataccgg gaagggaagg agacaagcc cggccgcgtg    3120
ttccgtccac acgttgcgga cgtactcaag ttctgccggc gagccgatgg cggaaagcag   3180
aaagacgacc tggtagaaac ctgcattcgg ttaaacacca cgcacgttgc catgcagcgt   3240
```

```
acgaagaagg ccaagaacgg ccgcctggtg acggtatccg agggtgaagc cttgattagc   3300
cgctacaaga tcgtaaagag cgaaccgggc cggccggagt acatcgagat cgagctagct   3360
gattggatgt accgcgagat cacagaaggc aagaacccgg acgtgctgac ggttcacccc   3420 gattacttt tgatcgatcc cggcatcggc cgttttctct accgcctggc acgccgcgcc    3480
gcaggcaagg cagaagccag atggttgttc aagacgatct acgaacgcag tggcagcgcc   3540
ggagagttca agaagttctg tttcaccgtg cgcaagctga tcgggtcaaa tgacctgccg   3600
gagtacgatt tgaaggagga ggcggggcag gctggcccga tcctagtcat gcgctaccgc   3660
aacctgatcg agggcgaagc atccgccggt tcctaatgta cggagcagat gctagggcaa   3720
attgccctag caggggaaaa aggtcgaaaa ggtctctttc ctgtggatag cacgtacatt   3780
gggaacccaa agccgtacat tgggaaccgg aacccgtaca ttgggaaccc aaagccgtac   3840
attgggaacc ggtcacacat gtaagtgact gatataaaag agaaaaaagg cgatttttcc   3900
gcctaaaact ctttaaaact tattaaaact cttaaaaccc gcctggcctg tgcataactg   3960
tctggccagc gcacagccga agagctgcaa aaagcgccta cccttcggtc gctgcgctcc   4020 ctacgcccg ccgcttcgcg tcggcctatc gcggccgctg gccgctcaaa atggctggc    4080 ctacggccag gcaatctacc agggcgcgga caagccgcgc cgtcgccact cgaccgccgg   4140
cgcccacatc aaggcaccct gcctcgcgcg tttcggtgat gacggtgaaa acctctgaca   4200
catgcagctc ccggagacgg tcacagcttg tctgtaagcg gatgccggga gcagacaagc   4260
ccgtcagggc gcgtcagcgg gtgttggcgg gtgtcgggc gcagccatga cccagtcacg    4320
tagcgatagc ggagtgtata ctggcttaac tatgcggcat cagagcagat tgtactgaga   4380
gtgcaccata tgcggtgtga ataccgcac agatgcgtaa ggagaaaata ccgcatcagg    4440
cgctcttccg cttcctcgct cactgactcg ctgcgctcgg tcgttcggct gcggcgagcg   4500
gtatcagctc actcaaaggc ggtaatacgg ttatccacag aatcagggga taacgcagga   4560
aagaacatgt gagcaaaagg ccagcaaaag gccaggaacc gtaaaaaggc cgcgttgctg   4620 gcgttttcc ataggctccg ccccctgac gagcatcaca aaaatcgacg ctcaagtcag     4680
aggtggcgaa acccgacagg actataaaga taccaggcgt ttccccctgg aagctccctc   4740
gtgcgctctc ctgttccgac cctgccgctt accggatacc tgtccgcctt tctcccttcg   4800
ggaagcgtgg cgctttctca tagctcacgc tgtaggtatc tcagttcggt gtaggtcgtt   4860
cgctccaagc tgggctgtgt gcacgaaccc ccgttcagc ccgaccgctg cgccttatcc     4920
ggtaactatc gtcttgagtc aacccggta agacacgact tatcgccact ggcagcagcc    4980
actggtaaca ggattagcag agcgaggtat gtaggcggtg ctacagagtt cttgaagtgg   5040
tggcctaact acggctacac tagaaggaca gtatttggta tctgcgctct gctgaagcca   5100
gttaccttcg gaaaaagagt tggtagctct tgatccggca acaaaccac cgctggtagc    5160 ggtggttttt ttgttgcaa gcagcagatt acgcgcagaa aaaaggatc tcaagaagat    5220 cctttgatct tttctacggg gtctgacgct cagtggaacg aaaactcacg ttaagggatt   5280
ttggtcatgc attctaggta ctaaaacaat tcatccagta aaatataata ttttattttc   5340
tcccaatcag gcttgatccc cagtaagtca aaaaatagct cgacatactg ttcttccccg   5400
atatcctccc tgatcgaccg gacgcagaag gcaatgtcat accacttgtc cgccctgccg   5460
cttctcccaa gatcaataaa gccacttact ttgccatctt tcacaaagat gttgctgtct   5520
cccaggtcgc cgtgggaaaa acaagttcc tcttcgggct tttccgtctt taaaaaatca   5580
tacagctcgc gcggatcttt aaatggagtg tcttcttccc agttttcgca atccacatcg   5640
```

```
gccagatcgt tattcagtaa gtaatccaat tcggctaagc ggctgtctaa gctattcgta    5700
tagggacaat ccgatatgtc gatggagtga aagagcctga tgcactccgc atacagctcg    5760
ataatctttt cagggctttg ttcatcttca tactcttccg agcaaaggac gccatcggcc    5820
tcactcatga gcagattgct ccagccatca tgccgttcaa agtgcaggac ctttggaaca    5880
ggcagctttc cttccagcca tagcatcatg tccttttccc gttccacatc ataggtggtc    5940
cctttatacc ggctgtccgt cattttaaaa tataggtttt cattttctcc caccagctta    6000
tataccttag caggagacat tccttccgta tcttttacgc agcggtattt ttcgatcagt    6060
tttttcaatt ccggtgatat tctcattta gccatttatt atttccttcc tcttttctac    6120
agtatttaaa gatacccccaa gaagctaatt ataacaagac gaactccaat tcactgttcc    6180
ttgcattcta aaaccttaaa taccagaaaa cagcttttc aaagttgttt tcaaagttgg    6240
cgtataacat agtatcgacg gagccgattt tgaaaccgcg gtgatcacag gcagcaacgc    6300
tctgtcatcg ttacaatcaa catgctaccc tccgcgagat catccgtgtt tcaaacccgg    6360
cagcttagtt gccgttcttc cgaatagcat cggtaacatg agcaaagtct gccgccttac    6420
aacggctctc ccgctgacgc cgtcccggac tgatgggctg cctgtatcga gtggtgattt    6480
tgtgccgagc tgccggtcgg ggagctgttg gctggctggt ggcaggatat attgtggtgt    6540
aaacaaattg acgcttagac aacttaataa cacattgcgg acgtttttaa tgtactgaat    6600
taacgccgaa ttaattcggg ggatctggat tttagtactg gattttggtt ttaggaatta    6660
gaaattttat tgatagaagt attttacaaa tacaaataca tactaagggt ttcttatatg    6720
ctcaacacat gagcgaaacc ctataggaac cctaattccc ttatctggga actactcaca    6780
cattattatg gagaaactcg agcttgtcga tcgacagatc cggtcggcat ctactctatt    6840
tctttgccct cggacgagtg ctggggcgtc ggtttccact atcggcgagt acttctacac    6900
agccatcggt ccagacggcc gcgcttctgc gggcgatttg tgtacgcccg acagtcccgg    6960
ctccggatcg gacgattgcg tcgcatcgac cctgcgccca agctgcatca tcgaaattgc    7020
cgtcaaccaa gctctgatag agttggtcaa gaccaatgcg gagcatatac gcccggagtc    7080
gtggcgatcc tgcaagctcc ggatgcctcc gctcgaagta gcgcgtctgc tgctccatac    7140
aagccaacca cggcctccag aagaagatgt tggcgacctc gtattgggaa tccccgaaca    7200
tcgcctcgct ccagtcaatg accgctgtta tgcggccatt gtccgtcagg acattgttgg    7260
agccgaaatc cgcgtgcacg aggtgccgga cttcggggca gtcctcggcc caaagcatca    7320
gctcatcgag agcctgcgcg acggacgcac tgacggtgtc gtccatcaca gtttgccagt    7380
gatacacatg gggatcagca atcgcgcata tgaaatcacg ccatgtagtg tattgaccga    7440
ttccttgcgg tccgaatggg ccgaacccgc tcgtctggct aagatcggcc gcagcgatcg    7500
catccatagc ctccgcgacc ggttgtagaa cagcgggcag ttcggtttca ggcaggtctt    7560
gcaacgtgac accctgtgca cggcgggaga tgcaataggt caggctctcg ctaaactccc    7620
caatgtcaag cacttccgga atcgggagcg cggccgatgc aaagtgccga taaacataac    7680
gatctttgta gaaaccatcg gcgcagctat ttacccgcag gacatatcca cgccctccta    7740
catcgaagct gaaagcacga gattcttcgc cctccgagag ctgcatcagg tcggagacgc    7800
tgtcgaactt ttcgatcaga aacttctcga cagacgtcgc ggtgagttca ggcttttca    7860 tatctcattg cccccccgga tctgcgaaag ctcgagagag atagatttgt agagagagac    7920
tggtgatttc agcgtgtcct ctccaaatga aatgaacttc cttatataga ggaaggtctt    7980
gcgaaggata gtgggattgt gcgtcatccc ttacgtcagt ggagatatca catcaatcca    8040
```

```
cttgctttga agacgtggtt ggaacgtctt cttttccac gatgctcctc gtgggtgggg      8100
gtccatcttt gggaccactg tcggcagagg catcttgaac gatagccttt cctttatcgc      8160
aatgatggca tttgtaggtg ccaccttcct tttctactgt cctttgatg aagtgacaga       8220 tagctgggca atggaatccg aggaggtttc ccgatattac cctttgttga aaagtctcaa      8280
tagccctttg gtcttctgag actgtatctt tgatattctt ggagtagacg agagtgtcgt      8340
gctccaccat gttatcacat caatccactt gctttgaaga cgtggttgga acgtcttctt      8400
tttccacgat gctcctcgtg ggtgggggtc catctttggg accactgtcg gcagaggcat      8460
cttgaacgat agccttccct ttatcgcaat gatggcattt gtaggtgcca ccttcctttt      8520
ctactgtcct tttgatgaag tgacagatag ctgggcaatg aatccgagg aggtttcccg       8580 atattccct tgttgaaaa gtctcaatag ccctttggtc ttctgagact gtatctttga        8640
tattcttgga gtagacgaga gtgtcgtgct ccaccatgtt ggcaagctgc tctagccaat      8700
acgcaaaccg cctctccccg cgcgttggcc gattcattaa tgcagctggc acgacaggtt     8760
tcccgactgg aaagcgggca gtgagcgcaa cgcaattaat gtgagttagc tcactcatta     8820
ggcaccccag gctttacact ttatgcttcc ggctcgtatg ttgtgtggaa ttgtgagcgg      8880
ataacaattt cacacaggaa acagctatga ccatgattac gaattcccctt aattaaggcg    8940 cgccgatact gaattaacgc cgaattaatt cgggggatct ggattttagt actggatttt     9000
ggttttagga attagaaatt ttattgatag aagtatttta caaatacaaa tacatactaa      9060
gggtttctta tatgctcaac acatgagcga accctatag gaaccctaat tcccttatct       9120
gggaactact cacacattat tatggagaaa ccaggccgaa gcccaaagca tcccacacaa     9180
ccaagaggag agagacctta tcaaaaaaaa agaggagaga gacgacaaat ccgctccccca     9240 ccccaccat cgttccttcc cagctggtcg atcgatgacc ttgttcatcc tcatcacgct       9300
cggagctcaa ttcgtctcct gactccgcca gagggaggt ggattatctt gaggggaacg       9360
gtcatgtact tcagtgcact ctggtgttga ggcctcaagt caggaacacc caagttcga       9420 gttgaaagca tatccactgc aagtcagagc tgtcgcatat ggatgccaca acgagcagcg     9480
gagcttcctc ttctcttccc ctccatctca ttgtggatga tacactatcc ctcgtttctc     9540
cactgcagca atcgtaccaa cgatcgcagc gtcattgcct tggtgattct gctcctgggg    9600
agtttccgtt ggctgcaaac ccatcaatag tcctccatgt cctcacatca tgcaatctag    9660 aaccccgagga cctcgctcac ttggaggcaa catgcaaatt cttcaggaag cctgccaatt   9720
tccctcctga cttcctattg tcaatgtcgg aacttgcggc tttcgacatg tgccagaatc    9780
gtgctatatt taagcctatg ggtacacaag aaaagaaat gtttaagcag cgctgcggcg      9840
gtacctggaa gctagtgctt aggttcataa ctctaggtga agcatgttgt cggcgagaaa     9900
aatctcaggc aattgctgga cctggccaca gcgtcgctgt gacagcaagt ggcgctgctt     9960
actcttttgg gtccaacaac tccggccaac ttggccatga ccgtttagaa gaggagtgga    10020
gaccacgtcc catcagatca ttgcagggta ttcgaattat tcaggcagca gcaggagcag    10080
ggcgtactat gctcgttagt gatgctggta gggtgtatgc atttgggaag gattcctttg    10140
gagaggtaga atatgggaat caaggttcaa gggttgtgac tacgccacag ttggtggaat   10200
cattgaagga catatacatt gtacaggctg caataggaa cttctttact gctgtgttat     10260
ctcgggaggg atgcgtatat acatttttctt ggggtggcga catgaaactt ggtcaccaaa  10320
cagagccaaa cgatgtacag cctcatcttc tcgcaggccc tcttgaggac attccagtag    10380
tgcagatagc tgcaggctac tgctatctcc ttcttctggc atgccaacca agtggcatgt   10440
```

```
ctgtttattc tgttggttgt ggtttaggag ggaagcttgg ccatggctcg cgaagtgatg    10500
agaaataccc taggttgatt gagcagttcc agaccctgaa tatacagcca gtggtggttg    10560
ctgcgggtgc ttggcatgct gctgttgtgg gcaaggatgg gcgagtttgt acttggggat    10620
gggggcgtta tggctgcttg gggcatggta atgaggaatg tgagtctgtt cccaaggtag    10680
ttgagacctt gagcagtgtg aaggctgtcc atgtagcaac cggagattac accacatttg    10740
ttgtgtcaca taaaggtgat gtttactcgt ttggatgtgg tgaatcatca agccttggcc    10800
acaatactgc gattgagggt aataacaggc acagcaatgt ccttagccct gagctggtga    10860
cctcttcgca gagaaccgat gaaagggtgg tgcatgtcag cctaacgaat tccatatact    10920
ggaatgcaca tacatttgca ctgacagagt cagcaaaatt gtatgcattc ggcgcagggg    10980
acaaaggaca gctaggcact gaacttgtcg aacaccgaag cgagaggggt accccggagc    11040
aggtcgatat tgacctcaat taggttcagt tgcagcacaa tgcctcccctt tcgcccttttt   11100 gcttcagttg cacacttcta accatcactt ttctaactca ccactctttg cattgcatgc    11160
tcctagtctg taccgcgttg atccttgtca atattgttag atttgttagc cagcaaaaca    11220
aggaatttgt ttttcatatg attgattctc tttagaaagc ttgtgtatat atttgtgatt    11280
gtaaatataa caagcaggtc ttcttgtcag ttccttcaaa catgagccgc tgctaatgga    11340
gagagataga tttgtagaga gagactggtg atttcagcgt gtcctctcca aatgaaatga    11400
acttccttat ataggaaag ggtcttgcga aggatagtgg gattgtgcgt catcccttac    11460
gtcagtggag atatcacatc aatccacttg ctttgaagac gtggttggaa cgtcttcttt    11520
ttccacgatg ctcctcgtgg gtgggggtcc atctttggga ccactgtcgg cagagcatct    11580
tgaacgatag ccttttccttt atcgcaatga tggcatttgt aggtgccacc ttccttttct    11640
actgtccttt tgatgaagtg acagatagct gggcaatgga atccgaggag gtttcccgat    11700
attacccttt gttgaaaagt ctcaatagcc ctttggcctt ctgagactgt atctttgata    11760
ttcttggagt agacgagagt gtcgtgctcc accatgttca catcaatcca cttgctttga    11820
agacgtggtt ggaacgtctt cttttttccac gatgctcctc gtgggtgggg gtccatcttt    11880
gggaccactg tcggcagagg catcttgaac gatagccttt cctttatcgc aatgatggca    11940
tttgtaggtg ccaccttcct tttctactgt ccttttgatg aagtgacaga tagctgggca    12000
atggaatccg aggaggtttc ccgatattac cctttgttga aaagtctcaa tagcccttttg    12060 gtcttctgag actgtatctt tgatattctt ggagtagacg agagtgtcgt gctccaccat    12120
gttggcaagc tgctcttatt aattaaggcg cgccctgca                           12159
```

<210> SEQ ID NO 20
<211> LENGTH: 16
<212> TYPE: PRT
<213> ORGANISM: Artificial
<220> FEATURE:
<223> OTHER INFORMATION: Consensus, all plants

<400> SEQUENCE: 20

Ser Val Tyr Ser Val Gly Cys Gly Leu Gly Gly Lys Leu Gly His Gly
1               5                   10                  15

<210> SEQ ID NO 21
<211> LENGTH: 20
<212> TYPE: PRT
<213> ORGANISM: Artificial
<220> FEATURE:
<223> OTHER INFORMATION: Consensus, dicotyledonous plants

```
<400> SEQUENCE: 21

Gly Met Ser Val Tyr Ser Val Gly Cys Gly Leu Gly Gly Lys Leu Gly
1               5                   10                  15

His Gly Ser Arg
            20
```